(12) United States Patent
Howorka et al.

(10) Patent No.: US 11,485,995 B2
(45) Date of Patent: Nov. 1, 2022

(54) MEMBRANE-SPANNING NANOPORES

(71) Applicant: UCL BUSINESS LTD, London (GB)

(72) Inventors: Stefan Howorka, London (GB); Genevieve Pugh, London (GB); Jonathan Richard Burns, London (GB)

(73) Assignee: UCL BUSINESS LTD, London (GB)

( * ) Notice: Subject to any disclaimer, the term of this patent is extended or adjusted under 35 U.S.C. 154(b) by 544 days.

(21) Appl. No.: 16/317,085

(22) PCT Filed: Jul. 14, 2017

(86) PCT No.: PCT/GB2017/052089
§ 371 (c)(1),
(2) Date: Jan. 11, 2019

(87) PCT Pub. No.: WO2018/011603
PCT Pub. Date: Jan. 18, 2018

(65) Prior Publication Data
US 2019/0309350 A1 Oct. 10, 2019

(30) Foreign Application Priority Data
Jul. 14, 2016 (GB) ...................................... 1612458

(51) Int. Cl.
*C12Q 1/6825* (2018.01)
(52) U.S. Cl.
CPC .................................. *C12Q 1/6825* (2013.01)
(58) Field of Classification Search
CPC .. C12Q 1/68; C12Q 1/6825; C12Q 2565/157; C12Q 2565/631
See application file for complete search history.

(56) References Cited

U.S. PATENT DOCUMENTS

| 2007/0117109 | A1* | 5/2007 | Rothemund | C12N 15/10 |
| | | | | 435/6.12 |
| 2013/0345286 | A1* | 12/2013 | Gollob | A61K 45/06 |
| | | | | 514/44 A |
| 2014/0291153 | A1 | 10/2014 | Keyser et al. | |

FOREIGN PATENT DOCUMENTS

| EP | 2695949 | * | 10/2012 |
| EP | 2695949 | A1 | 2/2014 |

OTHER PUBLICATIONS

Burns et al. A biomimetic DNA-based channel for the ligand-controlled transport of charged molecular cargo across a biological membrane Nat Nanotechnol. Feb. 2016; vol. 11(2): p. 152-6 (Year: 2016).*
Hernandez-Ainsa DNA Origami Nanopores for Controlling DNA Translocation ACS Nano. vol. 7 No. 7 p. 6024-6030 (Year: 2013).*
Bayley et al., Functional engineered channels and pores (Review). Molecular Membrane Biology 21:209-220 (Year: 2004).*
Boccalon et al. Metal-Organic Transmembrane Nanopores. JACS 134 : 20310-20313 (Year: 2012).*
Boyd et al., Alkyl Chain Positional Isomers of Dodecyl-D-Glucoside: Thermotropic and Lyotropic Phase Behavior and Detergency. Langmuir 17 :6100-6107 (Year: 2001).*
Burns et al. Lipid-bilayer-spanning DNA nanopores with a bifunctional porphyrin anchor. Agnew. Chem. Int Ed. 52: 12069-12072 (Year: 2013).*
Burns et al., Self-assembled DNA nanopores that span lipid bilayers . . . Nan Letters 13: 2351-2356 (Year: 2013).*
Devi et al., Pd(II)-Mediated Assembly of Porphyrin Channels in Bilayer Membranes. Langmuir 27(4) :1448-1456 (Year: 2011).*
Gokel et al., Synthetic Ion Channels: From Pores to Biological Applications. Accounts of Chemical Research 46(12) : 2824-2833 (Year: 2013).*
Grilo et al., Alpha-tocopherol and gamma-tocopherol concentration in vegetable oils. Food Science and Technology 34(2) :379-385 (Year: 2014).*
Montenegro et al., Ion Channel Models Based on Self-Assembling Cyclic Peptide Nanotubes. Accounts of Chemical Research 46(12) : 2955-2965 (Year: 2013).*
Pogodaeva et al., Hydrophobicity Constants for Severalxanthones and Flavones. Chemistry of Natural Compounds 47(1) : 38 (Year: 2011).*
Sakai et al., Synthetic Ion Channels. Langmuir 29:9031-9040 (Year: 2013).*
Satake et al., Transmembrane Nanopores from Porphyrin Supramolecules. JACS 130 :6314-6315 (Year: 2008).*
Semple et al., Degradation of phenol and its methylated homologues by Ochromonas danica. FEMS Microbiology Letters 152:133-139 (Year: 1997).*
Vargas et al., Synthetic Ion Transporters that Work with Anion-π Interactions, Halogen Bonds, and Anion-Macrodipole Interactions. Account of Chemical Research 46(12) : 2791-2800 (Year: 2013).*
Zhao et al., Conformationally Controlled Oligocholate Membrane Transporters: Learning through Water Play. Account of Chemical Research 46(12) : 2763-2772 (Year: 2013).*

(Continued)

*Primary Examiner* — Ethan C Whisenant
(74) *Attorney, Agent, or Firm* — Nixon Peabody LLP; David S. Resnick; Nicole D. Kling

(57) ABSTRACT

A membrane-spanning nanopore is provided that comprises: i. at least one scaffold polynucleotide strand; ii. a plurality of staple polynucleotide strands; and iii. at least one hydrophobically-modified polynucleotide strand, wherein the at least one hydrophobically-modified polynucleotide strand comprises a polynucleotide strand and a hydrophobic moiety; wherein each of the plurality of staple polynucleotide strands hybridises to the at least one scaffold polynucleotide strand to form the three-dimensional structure of the membrane-spanning nanopore, and wherein the at least one hydrophobically-modified polynucleotide strand hybridises to a portion of the at least one scaffold polynucleotide strand, the membrane-spanning nanopore defining a central channel with a minimum internal width of at least about 5 nm. Membranes comprising the membrane-spanning nanopore and applications of those membranes are also provided.

17 Claims, 14 Drawing Sheets
Specification includes a Sequence Listing.

(56) References Cited

OTHER PUBLICATIONS

Xu et al.Formation, characterization and stability of oil nanodroplets on immersed substrates Adv. In Colloid and Interface Science (Year: 2015).*
Burns et al., "A biomimetic DNA-based channel for the ligand-controlled transport of charged molecular cargo across ] biological membrane." Nature Nanotechnology 11 (2): 152-156 (Year: 2016).*
Bell et al., DNA Origami Nanopores. Nano Letters 12:512-517 (Online Pub. date Dec. 2011) (Year: 2012).*
Sanderson et al., Nature 464 :158-159 (2010) (Year: 2010).*
Wei et al., DNA Origami Gatekeepers for Solid-State Nanopores Agnew. Chem. Int. Ed. 51:4864-4867 (May 2012). (Year: 2012).*
Burns et al., "A biomimetic DNA-based channel for the ligand-controlled transport of charged molecular cargo across a biological membrane." Nature Nanotechnology 11(2):152-156 (2016).
Burns et al., "Membrane-spanning DNA nanopores with cytotoxic effect." Angewandte Chemie 126(46):12674-12678 (2014).
Hernandez-Ainsa et al., "DNA origami nanopores for controlling DNA translocation." ACS Nano 7(7):6024-6030 (2013).
Langecker et al., "Supplementary Materials for Synthetic lipid membrane channels formed by designed DNA nanostructures." Science 338(6109):932-936 (2012).
Langecker et al., "Synthetic lipid membrane channels formed by designed DNA nanostructures." Science 338(6109):932-936 (2012).
Seifert et al., "Bilayer-Spinning DNA Nanopores with Voltage-Switching Between Open and Closed State" ACS nano 9(2): 1117-1126 (2015).

* cited by examiner

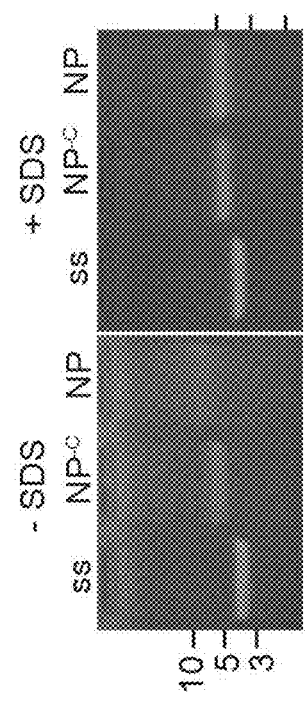
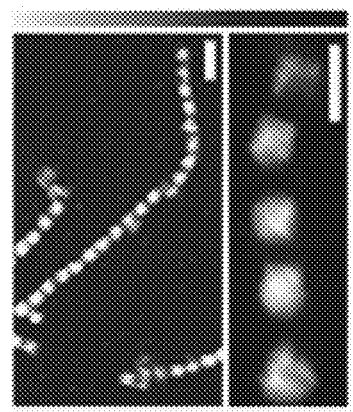
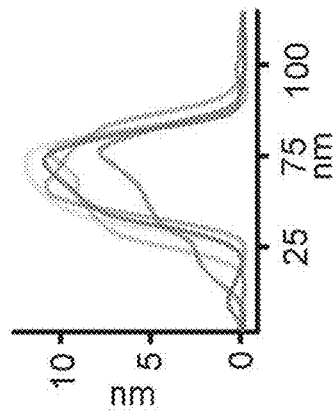
Figure 3A
Figure 3B
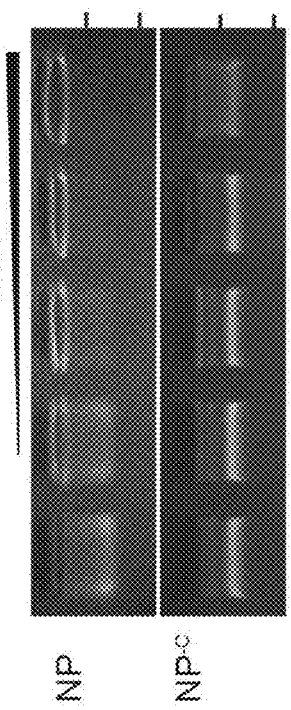
Figure 3C

SEQUENCE LISTING

<160> NUMBER OF SEQ ID NOS: 243

<210> SEQ ID NO 1
<211> LENGTH: 7249
<212> TYPE: DNA
<213> ORGANISM: Artificial Sequence
<220> FEATURE:
<223> OTHER INFORMATION: Scaffold

<400> SEQUENCE: 1

```
aatgctacta ctattagtag aattgatgcc accttttcag ctcgcgcccc aaatgaaaat      60
atagctaaac aggttattga ccatttgcga aatgtatcta atggtcaaac taaatctact     120
cgttcgcaga attgggaatc aactgttaca tggaatgaaa cttccagaca ccgtacttta     180
gttgcatatt taaaacatgt tgagctacag caccagattc agcaattaag ctctaagcca     240
tccgcaaaaa tgacctctta tcaaaaggag caattaaagg tactctctaa tcctgacctg     300
ttggagtttg cttccggtct ggttcgcttt gaagctcgaa ttaaaacgcg atatttgaag     360
tctttcgggc ttcctcttaa tctttttgat gcaatccgct ttgcttctga ctataatagt     420
cagggtaaag acctgatttt tgatttatgg tcattctcgt tttctgaact gtttaaagca     480
tttgaggggg attcaatgaa tatttatgac gattccgcag tattggacgc tatccagtct     540
aaacatttta ctattacccc ctctggcaaa acttcttttg caaaagcctc tcgctatttt     600
ggtttttatc gtcgtctggt aaacgagggt tatgatagtg ttgctcttac tatgcctcgt     660
aattcctttt ggcgttatgt atctgcatta gttgaatgtg gtattcctaa atctcaactg     720
atgaatcttt ctacctgtaa taatgttgtt ccgttagttc gttttattaa cgtagatttt     780
tcttcccaac gtcctgactg gtataatgag ccagttctta aaatcgcata aggtaattca     840
caatgattaa agttgaaatt aaaccatctc aagcccaatt tactactcgt tctggtgttc     900
```

```
tcgtcagggc aagccttatt cactgaatga gcagctttgt tacgttgatt tgggtaatga      960
atatccggtt cttgtcaaga ttactcttga tgaaggtcag ccagcctatg cgcctggtct     1020
gtacaccgtt catctgtcct ctttcaaagt tggtcagttc ggttccctta tgattgaccg     1080
tctgcgcctc gttccggcta agtaacatgg agcaggtcgc ggatttcgac acaatttatc     1140
aggcgatgat acaaatctcc gttgtacttt gtttcgcgct tggtataatc gctggggtc      1200 aaagatgagt gttttagtgt attctttcgc ctctttcgtt ttaggttggt gccttcgtag     1260
tggcattacg tattttaccc gtttaatgga aacttcctca tgaaaaagtc tttagtcctc     1320
aaagcctctg tagccgttgc taccctcgtt ccgatgctgt ctttcgctgc tgagggtgac     1380
gatcccgcaa aagcggcctt taactccctg caagcctcag cgaccgaata tatcggttat     1440
gcgtgggcga tggttgttgt cattgtcggc gcaactatcg gtatcaagct gtttaagaaa     1500
ttcacctcga aagcaagctg ataaaccgat acaattaaag gctccttttg gagccttttt     1560
ttttggagat tttcaacgtg aaaaaattat tattcgcaat tcctttagtt gttcctttct     1620
attctcactc cgctgaaact gttgaaagtt gtttagcaaa accccataca gaaaattcat     1680
ttactaacgt ctggaaagac gacaaaactt tagatcgtta cgctaactat gagggttgtc     1740
tgtggaatgc tacaggcgtt gtagtttgta ctggtgacga aactcagtgt tacggtacat     1800
gggttcctat tgggcttgct atccctgaaa atgagggtgg tggctctgag ggtggcggtt     1860
ctgagggtgg cggttctgag gtggcggta ctaaacctcc tgagtacggt gatacaccta      1920
ttccgggcta tacttatatc aaccctctcg acggcactta tccgcctggt actgagcaaa     1980
accccgctaa tcctaatcct tctcttgagg agtctcagcc tcttaatact ttcatgtttc     2040
agaataatag gttccgaaat aggcaggggg cattaactgt ttatacgggc actgttactc     2100
aaggcactga ccccgttaaa acttattacc agtacactcc tgtatcatca aaagccatgt     2160
atgacgctta ctggaacggt aaattcagag actgcgcttt ccattctggc tttaatgaag     2220
atccattcgt ttgtgaatat caaggccaat cgtctgacct gcctcaacct cctgtcaatg     2280
ctggcggcgg ctctggtggt ggttctggtg cggctctga gggtggtggc tctgagggtg      2340
gcggttctga gggtggcggc tctgaggag gcggttccgg tggtggctct ggttccggtg      2400
attttgatta tgaaaagatg gcaaacgcta ataagggggc tatgaccgaa atgccgatg      2460 aaaacgcgct acagtctgac gctaaaggca aacttgattc tgtcgctact gattacggtg     2520
ctgctatcga tggtttcatt ggtgacgttt ccggccttgc taatggtaat ggtgctactg     2580
gtgattttgc tggctctaat tcccaaatgg ctcaagtcgg tgacggtgat aattcacctt     2640
taatgaataa tttccgtcaa tatttacctt ccctccctca atcggttgaa tgtcgccctt     2700
ttgtctttag cgctggtaaa ccatatgaat tttctattga ttgtgacaaa ataaacttat     2760
tccgtggtgt ctttgcgttt cttttatatg ttgccacctt tatgtatgta ttttctacgt     2820
ttgctaacat actgcgtaat aaggagtctt aatcatgcca gttcttttgg gtattccgtt     2880
attattgcgt ttcctcggtt tccttctggt aactttgttc ggctatctgc ttacttttct     2940
taaaaagggc ttcggtaaga tagctattgc tatttcattg tttcttgctc ttattattgg     3000
gcttaactca attcttgtgg gttatctctc tgatattagc gctcaattac cctctgactt     3060
tgttcagggt gttcagttaa ttctcccgtc taatgcgctt ccctgttttt atgttattct     3120
ctctgtaaag gctgctattt tcatttttga cgttaaacaa aaaatcgttt cttatttgga     3180
ttgggataaa taatatggct gtttattttg taactggcaa attaggctct ggaaagacgc     3240
tcgttagcgt tggtaagatt caggataaaa ttgtagctgg gtgcaaaata gcaactaatc     3300
```

```
ttgatttaag gcttcaaaac ctcccgcaag tcgggaggtt cgctaaaacg cctcgcgttc   3360
ttagaatacc ggataagcct tctatatctg atttgcttgc tattgggcgc ggtaatgatt   3420
cctacgatga aaataaaaac ggcttgcttg ttctcgatga gtgcggtact tggtttaata   3480
cccgttcttg aatgataag gaaagacagc cgattattga ttggtttcta catgctcgta    3540
aattaggatg ggatattatt tttcttgttc aggacttatc tattgttgat aaacaggcgc   3600
gttctgcatt agctgaacat gttgtttatt gtcgtcgtct ggacagaatt actttacctt   3660
ttgtcggtac tttatattct cttattactg gctcgaaaat gcctctgcct aaattacatg   3720
ttggcgttgt taaatatggc gattctcaat taagccctac tgttgagcgt ggctttata    3780 ctggtaagaa tttgtataac gcatatgata ctaaacaggc ttttctagt aattatgatt     3840 ccggtgttta ttcttattta acgccttatt tatcacacgg tcggtatttc aaaccattaa   3900
atttaggtca gaagatgaaa ttaactaaaa tatatttgaa aaagttttct cgcgttcttt   3960
gtcttgcgat tggatttgca tcagcattta catatagtta tataacccaa cctaagccgg   4020
aggttaaaaa ggtagtctct cagacctatg attttgataa attcactatt gactcttctc   4080
agcgtcttaa tctaagctat cgctatgttt tcaaggattc taagggaaaa ttaattaata   4140
gcgacgattt acagaagcaa ggttattcac tcacatatat tgatttatgt actgtttcca   4200
ttaaaaaagg taattcaaat gaaattgtta aatgtaatta attttgtttt cttgatgttt   4260
gtttcatcat cttcttttgc tcaggtaatt gaaatgaata attcgcctct gcgcgatttt   4320
gtaacttggt attcaaagca atcaggcgaa tccgttattg tttctcccga tgtaaaaggt   4380
actgttactg tatattcatc tgacgttaaa cctgaaaatc tacgcaattt ctttatttct   4440
gttttacgtg ctaataattt tgatatggtt ggttcaattc cttccataat tcagaagtat   4500
aatccaaaca atcaggatta tattgatgaa ttgccatcat ctgataatca ggaatatgat   4560
gataattccg ctccttctgg tggtttcttt gttccgcaaa atgataatgt tactcaaact   4620
tttaaaatta ataacgttcg ggcaaaggat ttaatacgag ttgtcgaatt gtttgtaaag   4680
tctaatactt ctaaatcctc aaatgtatta tctattgacg gctctaatct attagttgtt   4740
agtgcaccta aagatatttt agataacctt cctcaattcc tttctactgt tgatttgcca   4800
actgaccaga tattgattga gggtttgata tttgaggttc agcaaggtga tgctttagat   4860
ttttcatttg ctgctggctc tcagcgtggc actgttgcag gcggtgttaa tactgaccgc   4920
ctcacctctg ttttatcttc tgctggtggt tcgttcggta ttttaatgg cgatgtttta   4980 gggctatcag ttcgcgcatt aaagactaat agccattcaa aaatattgtc tgtgccacgt   5040
attcttacgc tttcaggtca gaagggttct atctctgttg gccagaatgt ccctttatt    5100 actggtcgtg tgactggtga atctgccaat gtaaataatc catttcagac gattgagcgt   5160
caaaatgtag gtatttccat gagcgttttt cctgttgcaa tggctggcgg taatattgtt   5220
ctggatatta ccagcaaggc cgatagtttg agttcttcta ctcaggcaag tgatgttatt   5280
actaatcaaa gaagtattgc tacaacggtt aatttgcgtg atggacagac tcttttactc   5340
ggtggcctca ctgattataa aaacacttct caagattctg gcgtaccgtt cctgtctaaa   5400 atcccttta tcggcctcct gtttagctcc cgctctgatt ccaacgagga aagcacgtta    5460
tacgtgctcg tcaaagcaac catagtacgc gccctgtagc ggcgcattaa gcgcggcggg   5520
tgtggtggtt acgcgcagcg tgaccgctac acttgccagc gccctagcgc ccgctccttt   5580
cgctttcttc ccttcctttc tcgccacgtt cgccggcttt cccgtcaag ctctaaatcg    5640
```

-continued

```
ggggctccct  ttagggttcc  gatttagtgc  tttacggcac  ctcgacccca  aaaaacttga      5700
tttgggtgat  ggttcacgta  gtgggccatc  gccctgatag  acggttttc   gcccttgac      5760 gttggagtcc  acgttcttta  atagtggact  cttgttccaa  actggaacaa  cactcaaccc     5820
tatctcgggc  tattcttttg  atttataagg  gattttgccg  atttcggaac  caccatcaaa     5880
caggattttc  gcctgctggg  gcaaaccagc  gtggaccgct  tgctgcaact  ctctcagggc     5940
caggcggtga  agggcaatca  gctgttgccc  gtctcgctgg  tgaaaagaaa  aaccaccctg     6000
gcgcccaata  cgcaaaccgc  ctctccccgc  gcgttggccg  attcattaat  gcagctggca     6060
cgacaggttt  cccgactgga  aagcgggcag  tgagcgcaac  gcaattaatg  tgagttagct     6120
cactcattag  gcaccccagg  ctttacactt  tatgcttccg  gctcgtatgt  tgtgtggaat     6180
tgtgagcgga  taacaatttc  acacaggaaa  cagctatgac  catgattacg  aattcgagct     6240
cggtacccgg  ggatcctcta  gagtcgacct  gcaggcatgc  aagcttggca  ctggccgtcg     6300
ttttacaacg  tcgtgactgg  gaaaaccctg  gcgttaccca  acttaatcgc  cttgcagcac     6360
atcccccttt  cgccagctgg  cgtaatagcg  aagaggcccg  caccgatcgc  ccttcccaac     6420
agttgcgcag  cctgaatggc  gaatggcgct  ttgcctggtt  tccggcacca  gaagcggtgc     6480
cggaaagctg  gctggagtgc  gatcttcctg  aggccgatac  ggtcgtcgtc  ccctcaaact     6540
ggcagatgca  cggttacgat  gcgcccatct  acaccaacgt  aacctatccc  attacggtca     6600
atccgccgtt  tgttcccacg  gagaatccga  cgggttgtta  ctcgctcaca  tttaatgttg     6660
atgaaagctg  gctacaggaa  ggccagacgc  gaattatttt  tgatggcgtt  cctattggtt     6720
aaaaaatgag  ctgatttaac  aaaaatttaa  cgcgaatttt  aacaaaatat  taacgtttac     6780
aatttaaata  tttgcttata  caatcttcct  gttttgggg   cttttctgat  tatcaaccgg     6840
ggtacatatg  attgacatgc  tagttttacg  attaccgttc  atcgattctc  ttgtttgctc     6900
cagactctca  ggcaatgacc  tgatagcctt  tgtagatctc  tcaaaaatag  ctaccctctc     6960
cggcattaat  ttatcagcta  gaacggttga  atatcatatt  gatggtgatt  tgactgtctc     7020
cggcctttct  cacccttttg  aatctttacc  tacacattac  tcaggcattg  catttaaaat     7080
atatgagggt  tctaaaaatt  tttatccttg  cgttgaaata  aaggcttctc  cgcaaaagt      7140 attacagggt  cataatgttt  ttggtacaac  cgatttagct  ttatgctctg  aggctttatt    7200
gcttaatttt  gctaattctt  tgccttgcct  gtatgattta  ttggatgtt                 7249
```

<210> SEQ ID NO 2
<211> LENGTH: 48
<212> TYPE: DNA
<213> ORGANISM: Artificial Sequence
<220> FEATURE:
<223> OTHER INFORMATION: Staple

<400> SEQUENCE: 2

```
ggaacaaatc atatatccca caagcttacc gaagcttgat ttcggtcg              48
```

<210> SEQ ID NO 3
<211> LENGTH: 23
<212> TYPE: DNA
<213> ORGANISM: Artificial Sequence
<220> FEATURE:
<223> OTHER INFORMATION: staple

<400> SEQUENCE: 3

```
aaatgttaca aaatcgcgca aaa                                         23
```

```
<210> SEQ ID NO 4
<211> LENGTH: 19
<212> TYPE: DNA
<213> ORGANISM: Artificial Sequence
<220> FEATURE:
<223> OTHER INFORMATION: staple

<400> SEQUENCE: 4
taacaccacc agagccacc                                                    19

<210> SEQ ID NO 5
<211> LENGTH: 30
<212> TYPE: DNA
<213> ORGANISM: Artificial Sequence
<220> FEATURE:
<223> OTHER INFORMATION: staple

<400> SEQUENCE: 5
gaagggttag aaccttatac ttctgaataa                                        30

<210> SEQ ID NO 6
<211> LENGTH: 34
<212> TYPE: DNA
<213> ORGANISM: Artificial Sequence
<220> FEATURE:
<223> OTHER INFORMATION: Staple

<400> SEQUENCE: 6
cattaagtaa gcatgagcgc tccctgaact ctgg                                   34

<210> SEQ ID NO 7
<211> LENGTH: 27
<212> TYPE: DNA
<213> ORGANISM: Artificial Sequence
<220> FEATURE:
<223> OTHER INFORMATION: Staple

<400> SEQUENCE: 7
ccaagcgttg agccaaggtg aatgtca                                           27

<210> SEQ ID NO 8
<211> LENGTH: 28
<212> TYPE: DNA
<213> ORGANISM: Artificial Sequence
<220> FEATURE:
<223> OTHER INFORMATION: staple

<400> SEQUENCE: 8
gtgcattaat tagctcgaat tcgtaatc                                          28

<210> SEQ ID NO 9
<211> LENGTH: 33
<212> TYPE: DNA
<213> ORGANISM: Artificial Sequence
<220> FEATURE:
<223> OTHER INFORMATION: staple

<400> SEQUENCE: 9
aaaattcgaa ccaatactcc cgacaaagca ctc                                    33

<210> SEQ ID NO 10
<211> LENGTH: 35
<212> TYPE: DNA
<213> ORGANISM: Artificial Sequence
<220> FEATURE:
<223> OTHER INFORMATION: staple
```

<400> SEQUENCE: 10
acggccagta gctgtttcct gtgtgaaatt gttat                      35

<210> SEQ ID NO 11
<211> LENGTH: 35
<212> TYPE: DNA
<213> ORGANISM: Artificial Sequence
<220> FEATURE:
<223> OTHER INFORMATION: staple

<400> SEQUENCE: 11
ctcaagtgta agaatcataa ccgagtaaaa gaacg                      35

<210> SEQ ID NO 12
<211> LENGTH: 39
<212> TYPE: DNA
<213> ORGANISM: Artificial Sequence
<220> FEATURE:
<223> OTHER INFORMATION: staple

<400> SEQUENCE: 12
taagaagaaa atctacaaag ccggagacag tcaaatcac                  39

<210> SEQ ID NO 13
<211> LENGTH: 20
<212> TYPE: DNA
<213> ORGANISM: Artificial Sequence
<220> FEATURE:
<223> OTHER INFORMATION: staple

<400> SEQUENCE: 13
ggctccatta attgtcgaac                                       20

<210> SEQ ID NO 14
<211> LENGTH: 34
<212> TYPE: DNA
<213> ORGANISM: Artificial Sequence
<220> FEATURE:
<223> OTHER INFORMATION: staple

<400> SEQUENCE: 14
tatttcagag cggatggttg ctttgacgaa cgct                       34

<210> SEQ ID NO 15
<211> LENGTH: 20
<212> TYPE: DNA
<213> ORGANISM: Artificial Sequence
<220> FEATURE:
<223> OTHER INFORMATION: staple

<400> SEQUENCE: 15
ggctgaattt agccttgagt                                       20

<210> SEQ ID NO 16
<211> LENGTH: 36
<212> TYPE: DNA
<213> ORGANISM: Artificial Sequence
<220> FEATURE:
<223> OTHER INFORMATION: staple

<400> SEQUENCE: 16
aaagttacca gataaaagag gactaaagcg attata                     36

<210> SEQ ID NO 17
<211> LENGTH: 40

```
<212> TYPE: DNA
<213> ORGANISM: Artificial Sequence
<220> FEATURE:
<223> OTHER INFORMATION: staple

<400> SEQUENCE: 17
tgagtcagaa ggagcggaat tatcatcata tataatcagc                      40

<210> SEQ ID NO 18
<211> LENGTH: 38
<212> TYPE: DNA
<213> ORGANISM: Artificial Sequence
<220> FEATURE:
<223> OTHER INFORMATION: staple

<400> SEQUENCE: 18
cgcacttcca agaagataag tgtatagccg gattagga                        38

<210> SEQ ID NO 19
<211> LENGTH: 28
<212> TYPE: DNA
<213> ORGANISM: Artificial Sequence
<220> FEATURE:
<223> OTHER INFORMATION: staple

<400> SEQUENCE: 19
aacaacatgt tcaagagaac ggaatagg                                   28

<210> SEQ ID NO 20
<211> LENGTH: 28
<212> TYPE: DNA
<213> ORGANISM: Artificial Sequence
<220> FEATURE:
<223> OTHER INFORMATION: staple

<400> SEQUENCE: 20
gataatttgc cttgctaaag cgaataat                                   28

<210> SEQ ID NO 21
<211> LENGTH: 22
<212> TYPE: DNA
<213> ORGANISM: Artificial Sequence
<220> FEATURE:
<223> OTHER INFORMATION: staple

<400> SEQUENCE: 21
aactagcaac ggctacagag tc                                         22

<210> SEQ ID NO 22
<211> LENGTH: 35
<212> TYPE: DNA
<213> ORGANISM: Artificial Sequence
<220> FEATURE:
<223> OTHER INFORMATION: staple

<400> SEQUENCE: 22
aacagtgaga ctcctcagct aatgcagata aggct                           35

<210> SEQ ID NO 23
<211> LENGTH: 28
<212> TYPE: DNA
<213> ORGANISM: Artificial Sequence
<220> FEATURE:
<223> OTHER INFORMATION: staple

<400> SEQUENCE: 23
```
agaaccccca gtcacaccaa tcaatcct                                          28

<210> SEQ ID NO 24
<211> LENGTH: 38
<212> TYPE: DNA
<213> ORGANISM: Artificial Sequence
<220> FEATURE:
<223> OTHER INFORMATION: staple

<400> SEQUENCE: 24
agaacgtgga catcaagttt tcaattattg ctcctgct                               38

<210> SEQ ID NO 25
<211> LENGTH: 21
<212> TYPE: DNA
<213> ORGANISM: Artificial Sequence
<220> FEATURE:
<223> OTHER INFORMATION: staple

<400> SEQUENCE: 25
accggaacca gtagcgtaat t                                                 21

<210> SEQ ID NO 26
<211> LENGTH: 35
<212> TYPE: DNA
<213> ORGANISM: Artificial Sequence
<220> FEATURE:
<223> OTHER INFORMATION: staple

<400> SEQUENCE: 26
atttaacaag ctggcgaact gttgggaagg gccgg                                  35

<210> SEQ ID NO 27
<211> LENGTH: 26
<212> TYPE: DNA
<213> ORGANISM: Artificial Sequence
<220> FEATURE:
<223> OTHER INFORMATION: staple

<400> SEQUENCE: 27
agaactgata aagctaaagg gtgaga                                            26

<210> SEQ ID NO 28
<211> LENGTH: 35
<212> TYPE: DNA
<213> ORGANISM: Artificial Sequence
<220> FEATURE:
<223> OTHER INFORMATION: staple

<400> SEQUENCE: 28
aaccatcgcc ccactacgac ttattacacc agcgc                                  35

<210> SEQ ID NO 29
<211> LENGTH: 32
<212> TYPE: DNA
<213> ORGANISM: Artificial Sequence
<220> FEATURE:
<223> OTHER INFORMATION: staple

<400> SEQUENCE: 29
tttatttcgc aatcaatagg agggagggca cc                                     32

<210> SEQ ID NO 30
<211> LENGTH: 35
<212> TYPE: DNA
<213> ORGANISM: Artificial Sequence

```
<220> FEATURE:
<223> OTHER INFORMATION: staple

<400> SEQUENCE: 30
atcgagaaga tgggcggaac aaacggcgga ttgac                              35

<210> SEQ ID NO 31
<211> LENGTH: 27
<212> TYPE: DNA
<213> ORGANISM: Artificial Sequence
<220> FEATURE:
<223> OTHER INFORMATION: staple

<400> SEQUENCE: 31
tatttcggat aatcttgaca attatat                                       27

<210> SEQ ID NO 32
<211> LENGTH: 32
<212> TYPE: DNA
<213> ORGANISM: Artificial Sequence
<220> FEATURE:
<223> OTHER INFORMATION: staple

<400> SEQUENCE: 32
tgcgggtttt cccagtcaca ttacgccacg cc                                 32

<210> SEQ ID NO 33
<211> LENGTH: 21
<212> TYPE: DNA
<213> ORGANISM: Artificial Sequence
<220> FEATURE:
<223> OTHER INFORMATION: staple

<400> SEQUENCE: 33
ccaccctcaa gacaaagagt c                                             21

<210> SEQ ID NO 34
<211> LENGTH: 32
<212> TYPE: DNA
<213> ORGANISM: Artificial Sequence
<220> FEATURE:
<223> OTHER INFORMATION: staple

<400> SEQUENCE: 34
caaataagaa aatcgtaaaa aacaagagaa tc                                 32

<210> SEQ ID NO 35
<211> LENGTH: 48
<212> TYPE: DNA
<213> ORGANISM: Artificial Sequence
<220> FEATURE:
<223> OTHER INFORMATION: staple

<400> SEQUENCE: 35
ctaaagcatc acaatatctg gtcagttgca ctaacgcagc ctttacag                48

<210> SEQ ID NO 36
<211> LENGTH: 28
<212> TYPE: DNA
<213> ORGANISM: Artificial Sequence
<220> FEATURE:
<223> OTHER INFORMATION: staple

<400> SEQUENCE: 36
gaacgtagaa attaaacggg aatacact                                      28
```

```
<210> SEQ ID NO 37
<211> LENGTH: 20
<212> TYPE: DNA
<213> ORGANISM: Artificial Sequence
<220> FEATURE:
<223> OTHER INFORMATION: staple

<400> SEQUENCE: 37
ccacgctgag aaaggaattg                                               20

<210> SEQ ID NO 38
<211> LENGTH: 35
<212> TYPE: DNA
<213> ORGANISM: Artificial Sequence
<220> FEATURE:
<223> OTHER INFORMATION: staple

<400> SEQUENCE: 38
atgtagaaac gaccagaata cctacatttt gatta                              35

<210> SEQ ID NO 39
<211> LENGTH: 21
<212> TYPE: DNA
<213> ORGANISM: Artificial Sequence
<220> FEATURE:
<223> OTHER INFORMATION: staple

<400> SEQUENCE: 39
catgaggatg cagggacgag g                                             21

<210> SEQ ID NO 40
<211> LENGTH: 34
<212> TYPE: DNA
<213> ORGANISM: Artificial Sequence
<220> FEATURE:
<223> OTHER INFORMATION: staple

<400> SEQUENCE: 40
aacgcgcggg gaggcaacag cctacctttg tcgc                               34

<210> SEQ ID NO 41
<211> LENGTH: 20
<212> TYPE: DNA
<213> ORGANISM: Artificial Sequence
<220> FEATURE:
<223> OTHER INFORMATION: staple

<400> SEQUENCE: 41
aacggaacgc cgccagcttt                                               20

<210> SEQ ID NO 42
<211> LENGTH: 18
<212> TYPE: DNA
<213> ORGANISM: Artificial Sequence
<220> FEATURE:
<223> OTHER INFORMATION: staple

<400> SEQUENCE: 42
cattctggcc tctttaat                                                 18

<210> SEQ ID NO 43
<211> LENGTH: 22
<212> TYPE: DNA
<213> ORGANISM: Artificial Sequence
<220> FEATURE:
<223> OTHER INFORMATION: staple
```

<400> SEQUENCE: 43
gatagccgat cagcttccgc tt                                        22

<210> SEQ ID NO 44
<211> LENGTH: 32
<212> TYPE: DNA
<213> ORGANISM: Artificial Sequence
<220> FEATURE:
<223> OTHER INFORMATION: staple

<400> SEQUENCE: 44
cgcagagcca cgccaccctc agaaccgacc aa                             32

<210> SEQ ID NO 45
<211> LENGTH: 30
<212> TYPE: DNA
<213> ORGANISM: Artificial Sequence
<220> FEATURE:
<223> OTHER INFORMATION: staple

<400> SEQUENCE: 45
ccctcatagg taaatgctga acaatcggcc                                30

<210> SEQ ID NO 46
<211> LENGTH: 35
<212> TYPE: DNA
<213> ORGANISM: Artificial Sequence
<220> FEATURE:
<223> OTHER INFORMATION: staple

<400> SEQUENCE: 46
aacctcaacc accagcgtat tctatatttt cacct                          35

<210> SEQ ID NO 47
<211> LENGTH: 23
<212> TYPE: DNA
<213> ORGANISM: Artificial Sequence
<220> FEATURE:
<223> OTHER INFORMATION: staple

<400> SEQUENCE: 47
tgcctcatta aatgcccect gcc                                       23

<210> SEQ ID NO 48
<211> LENGTH: 24
<212> TYPE: DNA
<213> ORGANISM: Artificial Sequence
<220> FEATURE:
<223> OTHER INFORMATION: staple

<400> SEQUENCE: 48
aaattaagaa atgaccctgt aata                                      24

<210> SEQ ID NO 49
<211> LENGTH: 37
<212> TYPE: DNA
<213> ORGANISM: Artificial Sequence
<220> FEATURE:
<223> OTHER INFORMATION: staple

<400> SEQUENCE: 49
gtagcggaaa ttaacggaat agaccccag acttttt                         37

<210> SEQ ID NO 50

<210> SEQ ID NO 50
<211> LENGTH: 34
<212> TYPE: DNA
<213> ORGANISM: Artificial Sequence
<220> FEATURE:
<223> OTHER INFORMATION: staple

<400> SEQUENCE: 50
agccggaagc atagttagaa ttagttaatc caat                               34

<210> SEQ ID NO 51
<211> LENGTH: 25
<212> TYPE: DNA
<213> ORGANISM: Artificial Sequence
<220> FEATURE:
<223> OTHER INFORMATION: staple

<400> SEQUENCE: 51
gacagccgga aaccaggcaa agcgc                                         25

<210> SEQ ID NO 52
<211> LENGTH: 32
<212> TYPE: DNA
<213> ORGANISM: Artificial Sequence
<220> FEATURE:
<223> OTHER INFORMATION: staple

<400> SEQUENCE: 52
gcaatattga ctcaacatgt tttaaatatg ca                                 32

<210> SEQ ID NO 53
<211> LENGTH: 27
<212> TYPE: DNA
<213> ORGANISM: Artificial Sequence
<220> FEATURE:
<223> OTHER INFORMATION: staple

<400> SEQUENCE: 53
ggcggtcagt attaacaccg gcgcgaa                                       27

<210> SEQ ID NO 54
<211> LENGTH: 30
<212> TYPE: DNA
<213> ORGANISM: Artificial Sequence
<220> FEATURE:
<223> OTHER INFORMATION: staple

<400> SEQUENCE: 54
gaatcgtcga ctggataaac atgatagtac                                    30

<210> SEQ ID NO 55
<211> LENGTH: 35
<212> TYPE: DNA
<213> ORGANISM: Artificial Sequence
<220> FEATURE:
<223> OTHER INFORMATION: staple

<400> SEQUENCE: 55
ctagtcaaaa acgtctttcc cctcaatcct tgctg                              35

<210> SEQ ID NO 56
<211> LENGTH: 22
<212> TYPE: DNA
<213> ORGANISM: Artificial Sequence
<220> FEATURE:
<223> OTHER INFORMATION: staple

<400> SEQUENCE: 56
atgaacggtg tacagacttt ga                                              22

<210> SEQ ID NO 57
<211> LENGTH: 18
<212> TYPE: DNA
<213> ORGANISM: Artificial Sequence
<220> FEATURE:
<223> OTHER INFORMATION: staple

<400> SEQUENCE: 57
aattcaatat aaaatcgg                                                   18

<210> SEQ ID NO 58
<211> LENGTH: 40
<212> TYPE: DNA
<213> ORGANISM: Artificial Sequence
<220> FEATURE:
<223> OTHER INFORMATION: staple

<400> SEQUENCE: 58
aatgcacgca taaagaactg gaaatagcat atttcaaaaa                            40

<210> SEQ ID NO 59
<211> LENGTH: 35
<212> TYPE: DNA
<213> ORGANISM: Artificial Sequence
<220> FEATURE:
<223> OTHER INFORMATION: staple

<400> SEQUENCE: 59
acaaatatca gtaatgccga ttcaaccgtt ctagc                                 35

<210> SEQ ID NO 60
<211> LENGTH: 38
<212> TYPE: DNA
<213> ORGANISM: Artificial Sequence
<220> FEATURE:
<223> OTHER INFORMATION: staple

<400> SEQUENCE: 60
cgacggctgg taatatccag aacaatacgc tcaataat                              38

<210> SEQ ID NO 61
<211> LENGTH: 36
<212> TYPE: DNA
<213> ORGANISM: Artificial Sequence
<220> FEATURE:
<223> OTHER INFORMATION: staple

<400> SEQUENCE: 61
catcaactct ccgtggcatc gtaaccgtgc atctgc                                36

<210> SEQ ID NO 62
<211> LENGTH: 47
<212> TYPE: DNA
<213> ORGANISM: Artificial Sequence
<220> FEATURE:
<223> OTHER INFORMATION: staple

<400> SEQUENCE: 62
tgatagcgat aaattacctt agcccgaagt gttgttccag tttcact                    47

<210> SEQ ID NO 63
<211> LENGTH: 26
<212> TYPE: DNA

<210> SEQ ID NO 63
<211> LENGTH: 26
<212> TYPE: DNA
<213> ORGANISM: Artificial Sequence
<220> FEATURE:
<223> OTHER INFORMATION: staple

<400> SEQUENCE: 63
tgagtaatga atatgatgag agggta 26

<210> SEQ ID NO 64
<211> LENGTH: 35
<212> TYPE: DNA
<213> ORGANISM: Artificial Sequence
<220> FEATURE:
<223> OTHER INFORMATION: staple

<400> SEQUENCE: 64
ctgaggctag tttccaatac atacttgtca caaat 35

<210> SEQ ID NO 65
<211> LENGTH: 24
<212> TYPE: DNA
<213> ORGANISM: Artificial Sequence
<220> FEATURE:
<223> OTHER INFORMATION: staple

<400> SEQUENCE: 65
agaggctgcc cgtatatcag ccat 24

<210> SEQ ID NO 66
<211> LENGTH: 24
<212> TYPE: DNA
<213> ORGANISM: Artificial Sequence
<220> FEATURE:
<223> OTHER INFORMATION: staple

<400> SEQUENCE: 66
cttttgcggg aaataaagat aacg 24

<210> SEQ ID NO 67
<211> LENGTH: 47
<212> TYPE: DNA
<213> ORGANISM: Artificial Sequence
<220> FEATURE:
<223> OTHER INFORMATION: staple

<400> SEQUENCE: 67
cgccaccctc agaacaggcg cataggttca tcaagagacc tattatt 47

<210> SEQ ID NO 68
<211> LENGTH: 29
<212> TYPE: DNA
<213> ORGANISM: Artificial Sequence
<220> FEATURE:
<223> OTHER INFORMATION: staple

<400> SEQUENCE: 68
cattttttca ttaaataaag gaatgagat 29

<210> SEQ ID NO 69
<211> LENGTH: 35
<212> TYPE: DNA
<213> ORGANISM: Artificial Sequence
<220> FEATURE:
<223> OTHER INFORMATION: staple

<400> SEQUENCE: 69
ttgcaatcca aaataaacag aagattgatt ttgtt 35

<210> SEQ ID NO 70
<211> LENGTH: 24
<212> TYPE: DNA
<213> ORGANISM: Artificial Sequence
<220> FEATURE:
<223> OTHER INFORMATION: staple

<400> SEQUENCE: 70
ctaaaacacg cgcccaaatc agat                                          24

<210> SEQ ID NO 71
<211> LENGTH: 30
<212> TYPE: DNA
<213> ORGANISM: Artificial Sequence
<220> FEATURE:
<223> OTHER INFORMATION: staple

<400> SEQUENCE: 71
gagacccaat tctgcagtac cttttacatc                                    30

<210> SEQ ID NO 72
<211> LENGTH: 34
<212> TYPE: DNA
<213> ORGANISM: Artificial Sequence
<220> FEATURE:
<223> OTHER INFORMATION: staple

<400> SEQUENCE: 72
cgattaagtt gggaatcccc ctgaccataa atca                               34

<210> SEQ ID NO 73
<211> LENGTH: 20
<212> TYPE: DNA
<213> ORGANISM: Artificial Sequence
<220> FEATURE:
<223> OTHER INFORMATION: staple

<400> SEQUENCE: 73
catctgtagg taagggtaat                                               20

<210> SEQ ID NO 74
<211> LENGTH: 19
<212> TYPE: DNA
<213> ORGANISM: Artificial Sequence
<220> FEATURE:
<223> OTHER INFORMATION: staple

<400> SEQUENCE: 74
caccaaccta agaaacgtc                                                19

<210> SEQ ID NO 75
<211> LENGTH: 38
<212> TYPE: DNA
<213> ORGANISM: Artificial Sequence
<220> FEATURE:
<223> OTHER INFORMATION: staple

<400> SEQUENCE: 75
atgagcaata cagtgttttt ataatcacac aattcacg                           38

<210> SEQ ID NO 76
<211> LENGTH: 34
<212> TYPE: DNA
<213> ORGANISM: Artificial Sequence
<220> FEATURE:

<223> OTHER INFORMATION: staple

<400> SEQUENCE: 76
cggtacgatt tttgagaatt atcttaaaca gccc                              34

<210> SEQ ID NO 77
<211> LENGTH: 50
<212> TYPE: DNA
<213> ORGANISM: Artificial Sequence
<220> FEATURE:
<223> OTHER INFORMATION: staple

<400> SEQUENCE: 77
ccagcattgg aaagccgtaa aatcaggtct tgcccgcttg ggcgccaggg              50

<210> SEQ ID NO 78
<211> LENGTH: 23
<212> TYPE: DNA
<213> ORGANISM: Artificial Sequence
<220> FEATURE:
<223> OTHER INFORMATION: staple

<400> SEQUENCE: 78
aatttcattt ggcttagatg aaa                                          23

<210> SEQ ID NO 79
<211> LENGTH: 20
<212> TYPE: DNA
<213> ORGANISM: Artificial Sequence
<220> FEATURE:
<223> OTHER INFORMATION: staple

<400> SEQUENCE: 79
ttccggtcca cttcaccagt                                              20

<210> SEQ ID NO 80
<211> LENGTH: 34
<212> TYPE: DNA
<213> ORGANISM: Artificial Sequence
<220> FEATURE:
<223> OTHER INFORMATION: staple

<400> SEQUENCE: 80
caggagtgta ctggtaataa gggttttgct ctgt                              34

<210> SEQ ID NO 81
<211> LENGTH: 35
<212> TYPE: DNA
<213> ORGANISM: Artificial Sequence
<220> FEATURE:
<223> OTHER INFORMATION: staple

<400> SEQUENCE: 81
actctagacg cgcctgttta cttctggtgt atcgg                             35

<210> SEQ ID NO 82
<211> LENGTH: 31
<212> TYPE: DNA
<213> ORGANISM: Artificial Sequence
<220> FEATURE:
<223> OTHER INFORMATION: staple

<400> SEQUENCE: 82
atttacataa atttcccttc aaccgcctgg c                                 31

<210> SEQ ID NO 83
<211> LENGTH: 28
<212> TYPE: DNA
<213> ORGANISM: Artificial Sequence
<220> FEATURE:
<223> OTHER INFORMATION: staple

<400> SEQUENCE: 83
gcgaccacac ccgccgcgct ctacaggg                                    28

<210> SEQ ID NO 84
<211> LENGTH: 31
<212> TYPE: DNA
<213> ORGANISM: Artificial Sequence
<220> FEATURE:
<223> OTHER INFORMATION: staple

<400> SEQUENCE: 84
attttgcggg actcatagtc caccaccccg t                                31

<210> SEQ ID NO 85
<211> LENGTH: 28
<212> TYPE: DNA
<213> ORGANISM: Artificial Sequence
<220> FEATURE:
<223> OTHER INFORMATION: staple

<400> SEQUENCE: 85
aaatatctag cgcgttcacc gaccgaaa                                    28

<210> SEQ ID NO 86
<211> LENGTH: 34
<212> TYPE: DNA
<213> ORGANISM: Artificial Sequence
<220> FEATURE:
<223> OTHER INFORMATION: staple

<400> SEQUENCE: 86
atcccataat cggccgtaac aatagaaggc ccag                             34

<210> SEQ ID NO 87
<211> LENGTH: 24
<212> TYPE: DNA
<213> ORGANISM: Artificial Sequence
<220> FEATURE:
<223> OTHER INFORMATION: staple

<400> SEQUENCE: 87
agacaaaagg gaaaattaaa atac                                        24

<210> SEQ ID NO 88
<211> LENGTH: 35
<212> TYPE: DNA
<213> ORGANISM: Artificial Sequence
<220> FEATURE:
<223> OTHER INFORMATION: staple

<400> SEQUENCE: 88
gcctaatgag tgaggtcgtg ccggtttgaa ttata                            35

<210> SEQ ID NO 89
<211> LENGTH: 20
<212> TYPE: DNA
<213> ORGANISM: Artificial Sequence
<220> FEATURE:
<223> OTHER INFORMATION: staple

<400> SEQUENCE: 89
ttagacgtta gcaaaaaaaa                                                     20

<210> SEQ ID NO 90
<211> LENGTH: 35
<212> TYPE: DNA
<213> ORGANISM: Artificial Sequence
<220> FEATURE:
<223> OTHER INFORMATION: staple

<400> SEQUENCE: 90
gagtagaaac cgttgtcgtt atacaaaaag ccata                                    35

<210> SEQ ID NO 91
<211> LENGTH: 19
<212> TYPE: DNA
<213> ORGANISM: Artificial Sequence
<220> FEATURE:
<223> OTHER INFORMATION: staple

<400> SEQUENCE: 91
caccggcaaa aagattaag                                                      19

<210> SEQ ID NO 92
<211> LENGTH: 32
<212> TYPE: DNA
<213> ORGANISM: Artificial Sequence
<220> FEATURE:
<223> OTHER INFORMATION: staple

<400> SEQUENCE: 92
attataaagg tacatccaat aaattgcgta ga                                       32

<210> SEQ ID NO 93
<211> LENGTH: 45
<212> TYPE: DNA
<213> ORGANISM: Artificial Sequence
<220> FEATURE:
<223> OTHER INFORMATION: staple

<400> SEQUENCE: 93
tgctcattca gtgaataagt ttcatcggca ttttcggtca caacg                         45

<210> SEQ ID NO 94
<211> LENGTH: 18
<212> TYPE: DNA
<213> ORGANISM: Artificial Sequence
<220> FEATURE:
<223> OTHER INFORMATION: staple

<400> SEQUENCE: 94
taaatccttt ttatcaga                                                       18

<210> SEQ ID NO 95
<211> LENGTH: 23
<212> TYPE: DNA
<213> ORGANISM: Artificial Sequence
<220> FEATURE:
<223> OTHER INFORMATION: staple

<400> SEQUENCE: 95
agcattccac atgggattag tta                                                 23

<210> SEQ ID NO 96
<211> LENGTH: 34

```
<212> TYPE: DNA
<213> ORGANISM: Artificial Sequence
<220> FEATURE:
<223> OTHER INFORMATION: staple

<400> SEQUENCE: 96
gcaaataccc aaaccgatat aaccgataga acaa                               34

<210> SEQ ID NO 97
<211> LENGTH: 35
<212> TYPE: DNA
<213> ORGANISM: Artificial Sequence
<220> FEATURE:
<223> OTHER INFORMATION: staple

<400> SEQUENCE: 97
gagacggagg cggttaggtt gggataccga cgcag                              35

<210> SEQ ID NO 98
<211> LENGTH: 28
<212> TYPE: DNA
<213> ORGANISM: Artificial Sequence
<220> FEATURE:
<223> OTHER INFORMATION: staple

<400> SEQUENCE: 98
gctatttcct gagagaaagt cagattta                                      28

<210> SEQ ID NO 99
<211> LENGTH: 37
<212> TYPE: DNA
<213> ORGANISM: Artificial Sequence
<220> FEATURE:
<223> OTHER INFORMATION: staple

<400> SEQUENCE: 99
taatattaga cggtgtttaa caaggaattc aactttc                            37

<210> SEQ ID NO 100
<211> LENGTH: 21
<212> TYPE: DNA
<213> ORGANISM: Artificial Sequence
<220> FEATURE:
<223> OTHER INFORMATION: staple

<400> SEQUENCE: 100
cagacgattg gccttgcatt a                                             21

<210> SEQ ID NO 101
<211> LENGTH: 39
<212> TYPE: DNA
<213> ORGANISM: Artificial Sequence
<220> FEATURE:
<223> OTHER INFORMATION: staple

<400> SEQUENCE: 101
aaaacaccac cagtagaagg taaaagaag attattcat                           39

<210> SEQ ID NO 102
<211> LENGTH: 35
<212> TYPE: DNA
<213> ORGANISM: Artificial Sequence
<220> FEATURE:
<223> OTHER INFORMATION: staple

<400> SEQUENCE: 102
```
gatctaatct ttccaggaat accgaaagat tccgg            35

<210> SEQ ID NO 103
<211> LENGTH: 49
<212> TYPE: DNA
<213> ORGANISM: Artificial Sequence
<220> FEATURE:
<223> OTHER INFORMATION: staple

<400> SEQUENCE: 103
cattcgccat tcaaatgttt aataaatata acagttaagc cagaatgac     49

<210> SEQ ID NO 104
<211> LENGTH: 32
<212> TYPE: DNA
<213> ORGANISM: Artificial Sequence
<220> FEATURE:
<223> OTHER INFORMATION: staple

<400> SEQUENCE: 104
taaaatatct ttaggaggca aatcaacagt tg               32

<210> SEQ ID NO 105
<211> LENGTH: 20
<212> TYPE: DNA
<213> ORGANISM: Artificial Sequence
<220> FEATURE:
<223> OTHER INFORMATION: staple

<400> SEQUENCE: 105
gggcgatggt tttgcggatg                             20

<210> SEQ ID NO 106
<211> LENGTH: 38
<212> TYPE: DNA
<213> ORGANISM: Artificial Sequence
<220> FEATURE:
<223> OTHER INFORMATION: staple

<400> SEQUENCE: 106
gaatagaaag gttgcgccga aaacaggtaa gcccagtt         38

<210> SEQ ID NO 107
<211> LENGTH: 22
<212> TYPE: DNA
<213> ORGANISM: Artificial Sequence
<220> FEATURE:
<223> OTHER INFORMATION: staple

<400> SEQUENCE: 107
tggtggcatc ataaagcctc ag                          22

<210> SEQ ID NO 108
<211> LENGTH: 30
<212> TYPE: DNA
<213> ORGANISM: Artificial Sequence
<220> FEATURE:
<223> OTHER INFORMATION: staple

<400> SEQUENCE: 108
aacggattcg cctgaaacag ttgattaaca                  30

<210> SEQ ID NO 109
<211> LENGTH: 28
<212> TYPE: DNA
<213> ORGANISM: Artificial Sequence

```
<220> FEATURE:
<223> OTHER INFORMATION: staple

<400> SEQUENCE: 109
ccttatcaaa atcagagccc accctcag                                              28

<210> SEQ ID NO 110
<211> LENGTH: 30
<212> TYPE: DNA
<213> ORGANISM: Artificial Sequence
<220> FEATURE:
<223> OTHER INFORMATION: staple

<400> SEQUENCE: 110
caaaatccct tataaatggc gctggagaat                                            30

<210> SEQ ID NO 111
<211> LENGTH: 40
<212> TYPE: DNA
<213> ORGANISM: Artificial Sequence
<220> FEATURE:
<223> OTHER INFORMATION: staple

<400> SEQUENCE: 111
agccagcagc aaatgaaaaa tctacaattt tataccaacg                                 40

<210> SEQ ID NO 112
<211> LENGTH: 32
<212> TYPE: DNA
<213> ORGANISM: Artificial Sequence
<220> FEATURE:
<223> OTHER INFORMATION: staple

<400> SEQUENCE: 112
cagttgcacg taaaacagag aagccttata gc                                         32

<210> SEQ ID NO 113
<211> LENGTH: 35
<212> TYPE: DNA
<213> ORGANISM: Artificial Sequence
<220> FEATURE:
<223> OTHER INFORMATION: staple

<400> SEQUENCE: 113
ccgtcaatat atcaaacaga gccttagttg ctact                                      35

<210> SEQ ID NO 114
<211> LENGTH: 35
<212> TYPE: DNA
<213> ORGANISM: Artificial Sequence
<220> FEATURE:
<223> OTHER INFORMATION: staple

<400> SEQUENCE: 114
aatttacgag cagtaccgaa gccattgact tgcct                                      35

<210> SEQ ID NO 115
<211> LENGTH: 24
<212> TYPE: DNA
<213> ORGANISM: Artificial Sequence
<220> FEATURE:
<223> OTHER INFORMATION: staple

<400> SEQUENCE: 115
cagaaagtaa ttcagtacca ggcg                                                  24
```

<210> SEQ ID NO 116
<211> LENGTH: 25
<212> TYPE: DNA
<213> ORGANISM: Artificial Sequence
<220> FEATURE:
<223> OTHER INFORMATION: staple

<400> SEQUENCE: 116
gcgcaaaggg ggatgtgctg caagg                                         25

<210> SEQ ID NO 117
<211> LENGTH: 31
<212> TYPE: DNA
<213> ORGANISM: Artificial Sequence
<220> FEATURE:
<223> OTHER INFORMATION: staple

<400> SEQUENCE: 117
caaattagcc cccttattag cgtttgcagg t                                  31

<210> SEQ ID NO 118
<211> LENGTH: 18
<212> TYPE: DNA
<213> ORGANISM: Artificial Sequence
<220> FEATURE:
<223> OTHER INFORMATION: staple

<400> SEQUENCE: 118
agacaatatt tttgaatg                                                 18

<210> SEQ ID NO 119
<211> LENGTH: 24
<212> TYPE: DNA
<213> ORGANISM: Artificial Sequence
<220> FEATURE:
<223> OTHER INFORMATION: staple

<400> SEQUENCE: 119
ggatgaggtc atcccactac gtga                                          24

<210> SEQ ID NO 120
<211> LENGTH: 38
<212> TYPE: DNA
<213> ORGANISM: Artificial Sequence
<220> FEATURE:
<223> OTHER INFORMATION: staple

<400> SEQUENCE: 120
tttcgcaata aaatcataca ggcaaggcaa agaataaa                           38

<210> SEQ ID NO 121
<211> LENGTH: 33
<212> TYPE: DNA
<213> ORGANISM: Artificial Sequence
<220> FEATURE:
<223> OTHER INFORMATION: staple

<400> SEQUENCE: 121
ttgaggctat caggtcattg ttgagagaat cta                                33

<210> SEQ ID NO 122
<211> LENGTH: 35
<212> TYPE: DNA
<213> ORGANISM: Artificial Sequence
<220> FEATURE:
<223> OTHER INFORMATION: staple

<400> SEQUENCE: 122
ttgccagacg agaggcaccg ccacatagta agtaa                              35

<210> SEQ ID NO 123
<211> LENGTH: 35
<212> TYPE: DNA
<213> ORGANISM: Artificial Sequence
<220> FEATURE:
<223> OTHER INFORMATION: staple

<400> SEQUENCE: 123
gcgctagcaa aagaattttt aataagaaaa ccgac                              35

<210> SEQ ID NO 124
<211> LENGTH: 22
<212> TYPE: DNA
<213> ORGANISM: Artificial Sequence
<220> FEATURE:
<223> OTHER INFORMATION: staple

<400> SEQUENCE: 124
gaggccctca gagtagcgta ac                                            22

<210> SEQ ID NO 125
<211> LENGTH: 40
<212> TYPE: DNA
<213> ORGANISM: Artificial Sequence
<220> FEATURE:
<223> OTHER INFORMATION: staple

<400> SEQUENCE: 125
gtacgaaccg attaaaattc aaggcaaaag taaaatacgt                         40

<210> SEQ ID NO 126
<211> LENGTH: 40
<212> TYPE: DNA
<213> ORGANISM: Artificial Sequence
<220> FEATURE:
<223> OTHER INFORMATION: staple

<400> SEQUENCE: 126
atttttagaa cccgaaacca caacattatc attttgcaga                         40

<210> SEQ ID NO 127
<211> LENGTH: 43
<212> TYPE: DNA
<213> ORGANISM: Artificial Sequence
<220> FEATURE:
<223> OTHER INFORMATION: staple

<400> SEQUENCE: 127
ataaactaat agatttagaa gtattagttt taaaaataat aag                     43

<210> SEQ ID NO 128
<211> LENGTH: 38
<212> TYPE: DNA
<213> ORGANISM: Artificial Sequence
<220> FEATURE:
<223> OTHER INFORMATION: staple

<400> SEQUENCE: 128
ccaagaaaaa tcgtctgaaa tggaagccag ctttcgat                           38

<210> SEQ ID NO 129

```
<211> LENGTH: 34
<212> TYPE: DNA
<213> ORGANISM: Artificial Sequence
<220> FEATURE:
<223> OTHER INFORMATION: staple

<400> SEQUENCE: 129
agaataattt aatagctgca ttaatggtgc tttc                                 34

<210> SEQ ID NO 130
<211> LENGTH: 28
<212> TYPE: DNA
<213> ORGANISM: Artificial Sequence
<220> FEATURE:
<223> OTHER INFORMATION: staple

<400> SEQUENCE: 130
cttatgcgaa attaagcaaa ttctacta                                        28

<210> SEQ ID NO 131
<211> LENGTH: 24
<212> TYPE: DNA
<213> ORGANISM: Artificial Sequence
<220> FEATURE:
<223> OTHER INFORMATION: staple

<400> SEQUENCE: 131
gttattaaac tttacaaaca attc                                            24

<210> SEQ ID NO 132
<211> LENGTH: 21
<212> TYPE: DNA
<213> ORGANISM: Artificial Sequence
<220> FEATURE:
<223> OTHER INFORMATION: staple

<400> SEQUENCE: 132
ctaaaacacc gagcctgggg t                                               21

<210> SEQ ID NO 133
<211> LENGTH: 24
<212> TYPE: DNA
<213> ORGANISM: Artificial Sequence
<220> FEATURE:
<223> OTHER INFORMATION: staple

<400> SEQUENCE: 133
gacgctgaga agaacgcgac gcgt                                            24

<210> SEQ ID NO 134
<211> LENGTH: 19
<212> TYPE: DNA
<213> ORGANISM: Artificial Sequence
<220> FEATURE:
<223> OTHER INFORMATION: staple

<400> SEQUENCE: 134
taaaggaggt taagtatta                                                  19

<210> SEQ ID NO 135
<211> LENGTH: 34
<212> TYPE: DNA
<213> ORGANISM: Artificial Sequence
<220> FEATURE:
<223> OTHER INFORMATION: staple

<400> SEQUENCE: 135
```
gattgataaa tagagataat ttaaatgcaa tgcc 34

<210> SEQ ID NO 136
<211> LENGTH: 27
<212> TYPE: DNA
<213> ORGANISM: Artificial Sequence
<220> FEATURE:
<223> OTHER INFORMATION: staple

<400> SEQUENCE: 136
ttggatagcc ggcgaacgtg aagggaa 27

<210> SEQ ID NO 137
<211> LENGTH: 34
<212> TYPE: DNA
<213> ORGANISM: Artificial Sequence
<220> FEATURE:
<223> OTHER INFORMATION: staple

<400> SEQUENCE: 137
ggtcaataac ctgtttagct atagcattag gcaa 34

<210> SEQ ID NO 138
<211> LENGTH: 32
<212> TYPE: DNA
<213> ORGANISM: Artificial Sequence
<220> FEATURE:
<223> OTHER INFORMATION: staple

<400> SEQUENCE: 138
gcgagtgaat ttgaaaacaa accatcgcaa gg 32

<210> SEQ ID NO 139
<211> LENGTH: 49
<212> TYPE: DNA
<213> ORGANISM: Artificial Sequence
<220> FEATURE:
<223> OTHER INFORMATION: staple

<400> SEQUENCE: 139
tctcttaatt gagaatcttg taacgccact gcaggtcgac tctagagga 49

<210> SEQ ID NO 140
<211> LENGTH: 19
<212> TYPE: DNA
<213> ORGANISM: Artificial Sequence
<220> FEATURE:
<223> OTHER INFORMATION: staple

<400> SEQUENCE: 140
tccaaaatct ctaaatgaa 19

<210> SEQ ID NO 141
<211> LENGTH: 35
<212> TYPE: DNA
<213> ORGANISM: Artificial Sequence
<220> FEATURE:
<223> OTHER INFORMATION: staple

<400> SEQUENCE: 141
aggaaagcgg attgcatctt tgcgtatttc cagtc 35

<210> SEQ ID NO 142
<211> LENGTH: 40
<212> TYPE: DNA

<213> ORGANISM: Artificial Sequence
<220> FEATURE:
<223> OTHER INFORMATION: staple

<400> SEQUENCE: 142
ttgtgtcgaa atccgcaaag acagcatata aagcctgcgg					40

<210> SEQ ID NO 143
<211> LENGTH: 20
<212> TYPE: DNA
<213> ORGANISM: Artificial Sequence
<220> FEATURE:
<223> OTHER INFORMATION: staple

<400> SEQUENCE: 143
aatcgtaacc aaaggagcgg					20

<210> SEQ ID NO 144
<211> LENGTH: 34
<212> TYPE: DNA
<213> ORGANISM: Artificial Sequence
<220> FEATURE:
<223> OTHER INFORMATION: staple

<400> SEQUENCE: 144
caccgtcaac aatacgggta tcagggataa ggcg					34

<210> SEQ ID NO 145
<211> LENGTH: 28
<212> TYPE: DNA
<213> ORGANISM: Artificial Sequence
<220> FEATURE:
<223> OTHER INFORMATION: staple

<400> SEQUENCE: 145
atggtcatgc caagcggcgt taaagtag					28

<210> SEQ ID NO 146
<211> LENGTH: 26
<212> TYPE: DNA
<213> ORGANISM: Artificial Sequence
<220> FEATURE:
<223> OTHER INFORMATION: staple

<400> SEQUENCE: 146
accctcagca gcggacagcc taaagg					26

<210> SEQ ID NO 147
<211> LENGTH: 33
<212> TYPE: DNA
<213> ORGANISM: Artificial Sequence
<220> FEATURE:
<223> OTHER INFORMATION: staple

<400> SEQUENCE: 147
accatcaccc aatccaacgt acctttaaaa taa					33

<210> SEQ ID NO 148
<211> LENGTH: 19
<212> TYPE: DNA
<213> ORGANISM: Artificial Sequence
<220> FEATURE:
<223> OTHER INFORMATION: staple

<400> SEQUENCE: 148
tttttcttgc tggtttgcc					19

<210> SEQ ID NO 149
<211> LENGTH: 35
<212> TYPE: DNA
<213> ORGANISM: Artificial Sequence
<220> FEATURE:
<223> OTHER INFORMATION: staple

<400> SEQUENCE: 149
atagtagtat tttcaaagac accttcatta atttg                       35

<210> SEQ ID NO 150
<211> LENGTH: 34
<212> TYPE: DNA
<213> ORGANISM: Artificial Sequence
<220> FEATURE:
<223> OTHER INFORMATION: staple

<400> SEQUENCE: 150
gataagtgcc gtcgagaggg tcccatgtac tgtc                        34

<210> SEQ ID NO 151
<211> LENGTH: 26
<212> TYPE: DNA
<213> ORGANISM: Artificial Sequence
<220> FEATURE:
<223> OTHER INFORMATION: staple

<400> SEQUENCE: 151
cagtttgagg ggacaaaata gggggg                                 26

<210> SEQ ID NO 152
<211> LENGTH: 39
<212> TYPE: DNA
<213> ORGANISM: Artificial Sequence
<220> FEATURE:
<223> OTHER INFORMATION: staple

<400> SEQUENCE: 152
attcgtgtct ggtttgacca ttagatactc aggttttta                   39

<210> SEQ ID NO 153
<211> LENGTH: 35
<212> TYPE: DNA
<213> ORGANISM: Artificial Sequence
<220> FEATURE:
<223> OTHER INFORMATION: staple

<400> SEQUENCE: 153
aaaattatat gaatatacag taacgaacga gtcaa                       35

<210> SEQ ID NO 154
<211> LENGTH: 31
<212> TYPE: DNA
<213> ORGANISM: Artificial Sequence
<220> FEATURE:
<223> OTHER INFORMATION: staple

<400> SEQUENCE: 154
gatggcaatt catcaattcc tgagcccgaa c                           31

<210> SEQ ID NO 155
<211> LENGTH: 29
<212> TYPE: DNA
<213> ORGANISM: Artificial Sequence
<220> FEATURE:

<223> OTHER INFORMATION: staple

<400> SEQUENCE: 155
aacgaggggg agatttgtat catcaaagc                                    29

<210> SEQ ID NO 156
<211> LENGTH: 32
<212> TYPE: DNA
<213> ORGANISM: Artificial Sequence
<220> FEATURE:
<223> OTHER INFORMATION: staple

<400> SEQUENCE: 156
cataaggaaa cgttaaaggg ctttcgatca cg                                32

<210> SEQ ID NO 157
<211> LENGTH: 20
<212> TYPE: DNA
<213> ORGANISM: Artificial Sequence
<220> FEATURE:
<223> OTHER INFORMATION: staple

<400> SEQUENCE: 157
agatttagaa gtttcattcc                                              20

<210> SEQ ID NO 158
<211> LENGTH: 35
<212> TYPE: DNA
<213> ORGANISM: Artificial Sequence
<220> FEATURE:
<223> OTHER INFORMATION: staple

<400> SEQUENCE: 158
ccaaccagaa cctatatgtc tgagagatga ttgcc                             35

<210> SEQ ID NO 159
<211> LENGTH: 35
<212> TYPE: DNA
<213> ORGANISM: Artificial Sequence
<220> FEATURE:
<223> OTHER INFORMATION: staple

<400> SEQUENCE: 159
caacggaacc ctaaagggag cccccgagac gggga                             35

<210> SEQ ID NO 160
<211> LENGTH: 32
<212> TYPE: DNA
<213> ORGANISM: Artificial Sequence
<220> FEATURE:
<223> OTHER INFORMATION: staple

<400> SEQUENCE: 160
gtaatcaaaa ataattcgca attgtaaatc aa                                32

<210> SEQ ID NO 161
<211> LENGTH: 35
<212> TYPE: DNA
<213> ORGANISM: Artificial Sequence
<220> FEATURE:
<223> OTHER INFORMATION: staple

<400> SEQUENCE: 161
caacgagtag taaattgcat ttggggcaat tgctg                             35

```
<210> SEQ ID NO 162
<211> LENGTH: 35
<212> TYPE: DNA
<213> ORGANISM: Artificial Sequence
<220> FEATURE:
<223> OTHER INFORMATION: staple

<400> SEQUENCE: 162
tgtatcactc atttttaaac caagtaccaa ccgac                              35

<210> SEQ ID NO 163
<211> LENGTH: 20
<212> TYPE: DNA
<213> ORGANISM: Artificial Sequence
<220> FEATURE:
<223> OTHER INFORMATION: staple

<400> SEQUENCE: 163
gaaggttatc gacaactcgt                                              20

<210> SEQ ID NO 164
<211> LENGTH: 34
<212> TYPE: DNA
<213> ORGANISM: Artificial Sequence
<220> FEATURE:
<223> OTHER INFORMATION: staple

<400> SEQUENCE: 164
acaacaatag gaatgatata acctgaacag acga                              34

<210> SEQ ID NO 165
<211> LENGTH: 33
<212> TYPE: DNA
<213> ORGANISM: Artificial Sequence
<220> FEATURE:
<223> OTHER INFORMATION: staple

<400> SEQUENCE: 165
cctgagagag tttggttccg tgtgagtgcc tga                               33

<210> SEQ ID NO 166
<211> LENGTH: 44
<212> TYPE: DNA
<213> ORGANISM: Artificial Sequence
<220> FEATURE:
<223> OTHER INFORMATION: staple

<400> SEQUENCE: 166
ggaatgcagc ttcaaagcga gcaggcgaga aaaaccgtct atca                   44

<210> SEQ ID NO 167
<211> LENGTH: 20
<212> TYPE: DNA
<213> ORGANISM: Artificial Sequence
<220> FEATURE:
<223> OTHER INFORMATION: staple

<400> SEQUENCE: 167
aatttttggt gaattactga                                              20

<210> SEQ ID NO 168
<211> LENGTH: 29
<212> TYPE: DNA
<213> ORGANISM: Artificial Sequence
<220> FEATURE:
<223> OTHER INFORMATION: staple
```

<400> SEQUENCE: 168
ttttctgtag acagccggtt ttgatagcg                                29

<210> SEQ ID NO 169
<211> LENGTH: 32
<212> TYPE: DNA
<213> ORGANISM: Artificial Sequence
<220> FEATURE:
<223> OTHER INFORMATION: staple

<400> SEQUENCE: 169
ccgaacgaaa gtatggtttg cagtatgaac gt                            32

<210> SEQ ID NO 170
<211> LENGTH: 42
<212> TYPE: DNA
<213> ORGANISM: Artificial Sequence
<220> FEATURE:
<223> OTHER INFORMATION: staple

<400> SEQUENCE: 170
cgtagtctgg ccgccgtttt agaacgcggc aagcccgcct gt                 42

<210> SEQ ID NO 171
<211> LENGTH: 42
<212> TYPE: DNA
<213> ORGANISM: Artificial Sequence
<220> FEATURE:
<223> OTHER INFORMATION: staple

<400> SEQUENCE: 171
ccgctgtgag gccattacta gaaattcttg cttttgatga ta                 42

<210> SEQ ID NO 172
<211> LENGTH: 25
<212> TYPE: DNA
<213> ORGANISM: Artificial Sequence
<220> FEATURE:
<223> OTHER INFORMATION: staple

<400> SEQUENCE: 172
atatttgctt tgttacattt aaggg                                    25

<210> SEQ ID NO 173
<211> LENGTH: 32
<212> TYPE: DNA
<213> ORGANISM: Artificial Sequence
<220> FEATURE:
<223> OTHER INFORMATION: staple

<400> SEQUENCE: 173
cgtaagattc aaaatcggtt gtaccaatag ca                            32

<210> SEQ ID NO 174
<211> LENGTH: 45
<212> TYPE: DNA
<213> ORGANISM: Artificial Sequence
<220> FEATURE:
<223> OTHER INFORMATION: staple

<400> SEQUENCE: 174
ttttggggtc gaggtgccgt aaagggaaca agcaaacatc ggaaa              45

<210> SEQ ID NO 175
<211> LENGTH: 35

```
<212> TYPE: DNA
<213> ORGANISM: Artificial Sequence
<220> FEATURE:
<223> OTHER INFORMATION: staple

<400> SEQUENCE: 175
aacagtttca gtacaaattt tgcacttatc cgaga                                  35

<210> SEQ ID NO 176
<211> LENGTH: 30
<212> TYPE: DNA
<213> ORGANISM: Artificial Sequence
<220> FEATURE:
<223> OTHER INFORMATION: staple

<400> SEQUENCE: 176
cctcaggaag ttggtgtaca agcaattcct                                        30

<210> SEQ ID NO 177
<211> LENGTH: 34
<212> TYPE: DNA
<213> ORGANISM: Artificial Sequence
<220> FEATURE:
<223> OTHER INFORMATION: staple

<400> SEQUENCE: 177
ccgcccaaaa ggttaataag agaatataaa tcat                                   34

<210> SEQ ID NO 178
<211> LENGTH: 35
<212> TYPE: DNA
<213> ORGANISM: Artificial Sequence
<220> FEATURE:
<223> OTHER INFORMATION: staple

<400> SEQUENCE: 178
tataattgag tgaagcgcac atttgaggat tagag                                  35

<210> SEQ ID NO 179
<211> LENGTH: 35
<212> TYPE: DNA
<213> ORGANISM: Artificial Sequence
<220> FEATURE:
<223> OTHER INFORMATION: staple

<400> SEQUENCE: 179
ctgggatacg caaattgttt ggataccata tcaga                                  35

<210> SEQ ID NO 180
<211> LENGTH: 20
<212> TYPE: DNA
<213> ORGANISM: Artificial Sequence
<220> FEATURE:
<223> OTHER INFORMATION: staple

<400> SEQUENCE: 180
taataacatc caacaggaaa                                                   20

<210> SEQ ID NO 181
<211> LENGTH: 31
<212> TYPE: DNA
<213> ORGANISM: Artificial Sequence
<220> FEATURE:
<223> OTHER INFORMATION: staple

<400> SEQUENCE: 181
```
accatcatta ctcgccatta aacagaggtg a        31

<210> SEQ ID NO 182
<211> LENGTH: 37
<212> TYPE: DNA
<213> ORGANISM: Artificial Sequence
<220> FEATURE:
<223> OTHER INFORMATION: staple

<400> SEQUENCE: 182
agagaataac ataacaatga caaacaatgc atgatta        37

<210> SEQ ID NO 183
<211> LENGTH: 33
<212> TYPE: DNA
<213> ORGANISM: Artificial Sequence
<220> FEATURE:
<223> OTHER INFORMATION: staple

<400> SEQUENCE: 183
tctgtccatc acgcaaatta gaactcaacg agc        33

<210> SEQ ID NO 184
<211> LENGTH: 32
<212> TYPE: DNA
<213> ORGANISM: Artificial Sequence
<220> FEATURE:
<223> OTHER INFORMATION: staple

<400> SEQUENCE: 184
tatacagaat cagcaaaatt catctttagt tt        32

<210> SEQ ID NO 185
<211> LENGTH: 41
<212> TYPE: DNA
<213> ORGANISM: Artificial Sequence
<220> FEATURE:
<223> OTHER INFORMATION: staple

<400> SEQUENCE: 185
aatataattt tgataataga gagtcaaagg gcaaatcctg t        41

<210> SEQ ID NO 186
<211> LENGTH: 20
<212> TYPE: DNA
<213> ORGANISM: Artificial Sequence
<220> FEATURE:
<223> OTHER INFORMATION: staple

<400> SEQUENCE: 186
aatcctgaga ttctttgatt        20

<210> SEQ ID NO 187
<211> LENGTH: 35
<212> TYPE: DNA
<213> ORGANISM: Artificial Sequence
<220> FEATURE:
<223> OTHER INFORMATION: staple

<400> SEQUENCE: 187
atcttcatac atgaccagta tggcatttta ctatc        35

<210> SEQ ID NO 188
<211> LENGTH: 35
<212> TYPE: DNA
<213> ORGANISM: Artificial Sequence
<220> FEATURE:
<223> OTHER INFORMATION: staple

<400> SEQUENCE: 188
cttcagtgta gcggtcgcac gtatatgcaa atttc                                35

<210> SEQ ID NO 189
<211> LENGTH: 45
<212> TYPE: DNA
<213> ORGANISM: Artificial Sequence
<220> FEATURE:
<223> OTHER INFORMATION: staple

<400> SEQUENCE: 189 aacttttca atgtttagta caaacatcac acggaacggt acgcc                      45

<210> SEQ ID NO 190
<211> LENGTH: 37
<212> TYPE: DNA
<213> ORGANISM: Artificial Sequence
<220> FEATURE:
<223> OTHER INFORMATION: staple

<400> SEQUENCE: 190
ggccttggcc tcttcgctga cgttgtcgct caacata                              37

<210> SEQ ID NO 191
<211> LENGTH: 27
<212> TYPE: DNA
<213> ORGANISM: Artificial Sequence
<220> FEATURE:
<223> OTHER INFORMATION: staple

<400> SEQUENCE: 191
actgagctaa acaggaggcg attttag                                         27

<210> SEQ ID NO 192
<211> LENGTH: 35
<212> TYPE: DNA
<213> ORGANISM: Artificial Sequence
<220> FEATURE:
<223> OTHER INFORMATION: staple

<400> SEQUENCE: 192
agataaaaaa taccgaacga aatgatacgt ggcac                                35

<210> SEQ ID NO 193
<211> LENGTH: 24
<212> TYPE: DNA
<213> ORGANISM: Artificial Sequence
<220> FEATURE:
<223> OTHER INFORMATION: staple

<400> SEQUENCE: 193
tccccgggta ccggcgttgc gctc                                            24

<210> SEQ ID NO 194
<211> LENGTH: 32
<212> TYPE: DNA
<213> ORGANISM: Artificial Sequence
<220> FEATURE:
<223> OTHER INFORMATION: staple

<400> SEQUENCE: 194
cctttagagc caagtttgcc tttagcgaaa at                                   32

<210> SEQ ID NO 195
<211> LENGTH: 38
<212> TYPE: DNA
<213> ORGANISM: Artificial Sequence
<220> FEATURE:
<223> OTHER INFORMATION: staple

<400> SEQUENCE: 195
ttttcgtagg atgaaagcgt aagaggatag gtcacgat         38

<210> SEQ ID NO 196
<211> LENGTH: 19
<212> TYPE: DNA
<213> ORGANISM: Artificial Sequence
<220> FEATURE:
<223> OTHER INFORMATION: staple

<400> SEQUENCE: 196
cagtgagcga gaatcagct                             19

<210> SEQ ID NO 197
<211> LENGTH: 34
<212> TYPE: DNA
<213> ORGANISM: Artificial Sequence
<220> FEATURE:
<223> OTHER INFORMATION: staple

<400> SEQUENCE: 197
tatcatcctt atttacattg gcagattcat tctg             34

<210> SEQ ID NO 198
<211> LENGTH: 26
<212> TYPE: DNA
<213> ORGANISM: Artificial Sequence
<220> FEATURE:
<223> OTHER INFORMATION: staple

<400> SEQUENCE: 198
ctgatagccg ctattagaac agagat                      26

<210> SEQ ID NO 199
<211> LENGTH: 30
<212> TYPE: DNA
<213> ORGANISM: Artificial Sequence
<220> FEATURE:
<223> OTHER INFORMATION: staple

<400> SEQUENCE: 199
gggaaacctc taactcaata aataattgca                  30

<210> SEQ ID NO 200
<211> LENGTH: 36
<212> TYPE: DNA
<213> ORGANISM: Artificial Sequence
<220> FEATURE:
<223> OTHER INFORMATION: staple

<400> SEQUENCE: 200
acccatcagt ttaataaaaa tcggtttaac atttta            36

<210> SEQ ID NO 201
<211> LENGTH: 32
<212> TYPE: DNA
<213> ORGANISM: Artificial Sequence
<220> FEATURE:
<223> OTHER INFORMATION: staple

<400> SEQUENCE: 201
agtttcgtca ccagcggagc taacgagtga aa                             32

<210> SEQ ID NO 202
<211> LENGTH: 29
<212> TYPE: DNA
<213> ORGANISM: Artificial Sequence
<220> FEATURE:
<223> OTHER INFORMATION: staple

<400> SEQUENCE: 202
tcataatctc agactggcgt tttaattcg                                 29

<210> SEQ ID NO 203
<211> LENGTH: 38
<212> TYPE: DNA
<213> ORGANISM: Artificial Sequence
<220> FEATURE:
<223> OTHER INFORMATION: staple

<400> SEQUENCE: 203
tttagcctta aacgttaatt ataagcaaat atttagaa                       38

<210> SEQ ID NO 204
<211> LENGTH: 32
<212> TYPE: DNA
<213> ORGANISM: Artificial Sequence
<220> FEATURE:
<223> OTHER INFORMATION: staple

<400> SEQUENCE: 204
actgaggcga atgatgaaaa gtccactatt aa                             32

<210> SEQ ID NO 205
<211> LENGTH: 41
<212> TYPE: DNA
<213> ORGANISM: Artificial Sequence
<220> FEATURE:
<223> OTHER INFORMATION: staple

<400> SEQUENCE: 205
aagaggacag gcgcagacgg tcaattactt agccggaacg a                   41

<210> SEQ ID NO 206
<211> LENGTH: 20
<212> TYPE: DNA
<213> ORGANISM: Artificial Sequence
<220> FEATURE:
<223> OTHER INFORMATION: staple

<400> SEQUENCE: 206
agccgccgta agcgtctgac                                           20

<210> SEQ ID NO 207
<211> LENGTH: 35
<212> TYPE: DNA
<213> ORGANISM: Artificial Sequence
<220> FEATURE:
<223> OTHER INFORMATION: staple

<400> SEQUENCE: 207
taacaacccg tcggatatta aatgacgacg attac                          35

<210> SEQ ID NO 208

```
<211> LENGTH: 19
<212> TYPE: DNA
<213> ORGANISM: Artificial Sequence
<220> FEATURE:
<223> OTHER INFORMATION: staple

<400> SEQUENCE: 208
aactgtcgag tttcgacag                                                  19

<210> SEQ ID NO 209
<211> LENGTH: 32
<212> TYPE: DNA
<213> ORGANISM: Artificial Sequence
<220> FEATURE:
<223> OTHER INFORMATION: staple

<400> SEQUENCE: 209
agcactagca tgtcaatcaa aaaacaggcc at                                   32

<210> SEQ ID NO 210
<211> LENGTH: 20
<212> TYPE: DNA
<213> ORGANISM: Artificial Sequence
<220> FEATURE:
<223> OTHER INFORMATION: staple

<400> SEQUENCE: 210
cgctcatgga taataaaagg                                                 20

<210> SEQ ID NO 211
<211> LENGTH: 34
<212> TYPE: DNA
<213> ORGANISM: Artificial Sequence
<220> FEATURE:
<223> OTHER INFORMATION: staple

<400> SEQUENCE: 211
cggtgcaata aacatgtaat tgggtcagtc cgtt                                 34

<210> SEQ ID NO 212
<211> LENGTH: 22
<212> TYPE: DNA
<213> ORGANISM: Artificial Sequence
<220> FEATURE:
<223> OTHER INFORMATION: staple

<400> SEQUENCE: 212
ccgtagagct tgcgagctga aa                                              22

<210> SEQ ID NO 213
<211> LENGTH: 35
<212> TYPE: DNA
<213> ORGANISM: Artificial Sequence
<220> FEATURE:
<223> OTHER INFORMATION: staple

<400> SEQUENCE: 213
ttagcggttt taacgtaggc agaaaagcca aaaag                                35

<210> SEQ ID NO 214
<211> LENGTH: 28
<212> TYPE: DNA
<213> ORGANISM: Artificial Sequence
<220> FEATURE:
<223> OTHER INFORMATION: staple

<400> SEQUENCE: 214
```

```
ttgatgggca gcaagtgtaa atcttaac                                    28
```

<210> SEQ ID NO 215
<211> LENGTH: 32
<212> TYPE: DNA
<213> ORGANISM: Artificial Sequence
<220> FEATURE:
<223> OTHER INFORMATION: staple

<400> SEQUENCE: 215

```
cagaccatta gatagcagca ccgtaatcgc ct                               32
```

<210> SEQ ID NO 216
<211> LENGTH: 34
<212> TYPE: DNA
<213> ORGANISM: Artificial Sequence
<220> FEATURE:
<223> OTHER INFORMATION: staple

<400> SEQUENCE: 216

```
cgccattttg ttataatcag aaaagcccct atgt                             34
```

<210> SEQ ID NO 217
<211> LENGTH: 31
<212> TYPE: DNA
<213> ORGANISM: Artificial Sequence
<220> FEATURE:
<223> OTHER INFORMATION: staple

<400> SEQUENCE: 217

```
ttgcgggatc ggctttgaaa cgggcttgag a                                31
```

<210> SEQ ID NO 218
<211> LENGTH: 20
<212> TYPE: DNA
<213> ORGANISM: Artificial Sequence
<220> FEATURE:
<223> OTHER INFORMATION: staple

<400> SEQUENCE: 218

```
ctccggaacc agagccgccg                                             20
```

<210> SEQ ID NO 219
<211> LENGTH: 37
<212> TYPE: DNA
<213> ORGANISM: Artificial Sequence
<220> FEATURE:
<223> OTHER INFORMATION: Adaptor

<400> SEQUENCE: 219

```
ctccgtctat cttttgttc agaaaacgag aatcaaa                           37
```

<210> SEQ ID NO 220
<211> LENGTH: 37
<212> TYPE: DNA
<213> ORGANISM: Artificial Sequence
<220> FEATURE:
<223> OTHER INFORMATION: Adaptor

<400> SEQUENCE: 220

```
ctccgtctat ctttttttc aaactccaac agtatca                           37
```

<210> SEQ ID NO 221
<211> LENGTH: 32
<212> TYPE: DNA

<213> ORGANISM: Artificial Sequence
<220> FEATURE:
<223> OTHER INFORMATION: Adaptor

<400> SEQUENCE: 221
ctccgtctat cttatgactg accaacccgc ca                          32

<210> SEQ ID NO 222
<211> LENGTH: 29
<212> TYPE: DNA
<213> ORGANISM: Artificial Sequence
<220> FEATURE:
<223> OTHER INFORMATION: Adaptor

<400> SEQUENCE: 222
ctccgtctat cttcataacc ctcgtttac                              29

<210> SEQ ID NO 223
<211> LENGTH: 24
<212> TYPE: DNA
<213> ORGANISM: Artificial Sequence
<220> FEATURE:
<223> OTHER INFORMATION: Adaptor

<400> SEQUENCE: 223
ctccgtctat cttttatac tgcg                                    24

<210> SEQ ID NO 224
<211> LENGTH: 29
<212> TYPE: DNA
<213> ORGANISM: Artificial Sequence
<220> FEATURE:
<223> OTHER INFORMATION: Adaptor

<400> SEQUENCE: 224
ctccgtctat cagaaacacc agaaagtac                              29

<210> SEQ ID NO 225
<211> LENGTH: 29
<212> TYPE: DNA
<213> ORGANISM: Artificial Sequence
<220> FEATURE:
<223> OTHER INFORMATION: Adaptor

<400> SEQUENCE: 225
ctccgtctat cttaatcatt gtgaattac                              29

<210> SEQ ID NO 226
<211> LENGTH: 24
<212> TYPE: DNA
<213> ORGANISM: Artificial Sequence
<220> FEATURE:
<223> OTHER INFORMATION: Adaptor

<400> SEQUENCE: 226
ctccgtctat cttttaaga agtt                                    24

<210> SEQ ID NO 227
<211> LENGTH: 25
<212> TYPE: DNA
<213> ORGANISM: Artificial Sequence
<220> FEATURE:
<223> OTHER INFORMATION: Adaptor

<400> SEQUENCE: 227
ctccgtctat cttttttttg acttc                                  25

<210> SEQ ID NO 228
<211> LENGTH: 48
<212> TYPE: DNA
<213> ORGANISM: Artificial Sequence
<220> FEATURE:
<223> OTHER INFORMATION: Adaptor

<400> SEQUENCE: 228
ctccgtctat cttttttta tagtcagaag caggttgagg ccatcttt         48

<210> SEQ ID NO 229
<211> LENGTH: 32
<212> TYPE: DNA
<213> ORGANISM: Artificial Sequence
<220> FEATURE:
<223> OTHER INFORMATION: Adaptor

<400> SEQUENCE: 229
ctccgtctat ctttatctcc atgtcataag gg                         32

<210> SEQ ID NO 230
<211> LENGTH: 48
<212> TYPE: DNA
<213> ORGANISM: Artificial Sequence
<220> FEATURE:
<223> OTHER INFORMATION: Adaptor

<400> SEQUENCE: 230
ctccgtctat cgtcaggacg ttggcggaac aacatttgct acgtcagc         48

<210> SEQ ID NO 231
<211> LENGTH: 35
<212> TYPE: DNA
<213> ORGANISM: Artificial Sequence
<220> FEATURE:
<223> OTHER INFORMATION: Adaptor

<400> SEQUENCE: 231
acttaccctg actatttttt ttttgctacg tcagc                      35

<210> SEQ ID NO 232
<211> LENGTH: 35
<212> TYPE: DNA
<213> ORGANISM: Artificial Sequence
<220> FEATURE:
<223> OTHER INFORMATION: Adaptor

<400> SEQUENCE: 232
ctgtacaggt aacattcaac tattgctacg tcagc                      35

<210> SEQ ID NO 233
<211> LENGTH: 27
<212> TYPE: DNA
<213> ORGANISM: Artificial Sequence
<220> FEATURE:
<223> OTHER INFORMATION: Adaptor

<400> SEQUENCE: 233
aggtttaatt tcaactgcta cgtcagc                               27

<210> SEQ ID NO 234
<211> LENGTH: 27
<212> TYPE: DNA
<213> ORGANISM: Artificial Sequence
<220> FEATURE:

```
<223> OTHER INFORMATION: Adaptor

<400> SEQUENCE: 234
agcgctcatt ataccagcta cgtcagc                                          27

<210> SEQ ID NO 235
<211> LENGTH: 27
<212> TYPE: DNA
<213> ORGANISM: Artificial Sequence
<220> FEATURE:
<223> OTHER INFORMATION: Adaptor

<400> SEQUENCE: 235
gctgcttgcc ctgacggcta cgtcagc                                          27

<210> SEQ ID NO 236
<211> LENGTH: 27
<212> TYPE: DNA
<213> ORGANISM: Artificial Sequence
<220> FEATURE:
<223> OTHER INFORMATION: Adaptor

<400> SEQUENCE: 236
ctgagcgtcc atttttgcta cgtcagc                                          27

<210> SEQ ID NO 237
<211> LENGTH: 32
<212> TYPE: DNA
<213> ORGANISM: Artificial Sequence
<220> FEATURE:
<223> OTHER INFORMATION: Adaptor

<400> SEQUENCE: 237
ccctcagatt ttgcaatttt tgctacgtca gc                                    32

<210> SEQ ID NO 238
<211> LENGTH: 41
<212> TYPE: DNA
<213> ORGANISM: Artificial Sequence
<220> FEATURE:
<223> OTHER INFORMATION: Adaptor

<400> SEQUENCE: 238
tcacaaacaa ataaatcttt aaacattttt gctacgtcag c                          41

<210> SEQ ID NO 239
<211> LENGTH: 29
<212> TYPE: DNA
<213> ORGANISM: Artificial Sequence
<220> FEATURE:
<223> OTHER INFORMATION: Adaptor

<400> SEQUENCE: 239
atacaagcaa cactatttgc tacgtcagc                                        29

<210> SEQ ID NO 240
<211> LENGTH: 35
<212> TYPE: DNA
<213> ORGANISM: Artificial Sequence
<220> FEATURE:
<223> OTHER INFORMATION: Adaptor

<400> SEQUENCE: 240
tggaggaagc ccgaaatttt ttttgctacg tcagc                                 35
```

```
<210> SEQ ID NO 241
<211> LENGTH: 35
<212> TYPE: DNA
<213> ORGANISM: Artificial Sequence
<220> FEATURE:
<223> OTHER INFORMATION: Adaptor

<400> SEQUENCE: 241
ccaaccagac cggaagtttt ttttgctacg tcagc                              35

<210> SEQ ID NO 242
<211> LENGTH: 11
<212> TYPE: DNA
<213> ORGANISM: Artificial Sequence
<220> FEATURE:
<223> OTHER INFORMATION: Anchor
<220> FEATURE:
<221> NAME/KEY: misc_binding
<222> LOCATION: 11
<223> OTHER INFORMATION: /note="triethylene glycol moiety linked to
      cholesterol"

<400> SEQUENCE: 242
gatagacgga g                                                        11

<210> SEQ ID NO 243
<211> LENGTH: 11
<212> TYPE: DNA
<213> ORGANISM: Artificial Sequence
<220> FEATURE:
<223> OTHER INFORMATION: Anchor
<220> FEATURE:
<221> NAME/KEY: misc_binding
<222> LOCATION: 1
<223> OTHER INFORMATION: /note="triethylene glycol moiety linked to
      cholesterol"

<400> SEQUENCE: 243
gctgacgtag c                                                        11
```

MEMBRANE-SPANNING NANOPORES

CROSS-REFERENCE TO RELATED APPLICATIONS

This application is a 35 U.S.C. § 371 National Phase Entry Application of International Application No. PCT/GB2017/052089 filed Jul. 14, 2017, which designates the U.S. and claims benefit of foreign priority under 35 U.S.C. § 119(a) of GB provisional application No. 1612458.8 filed Jul. 14, 2016, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jan. 10, 2019, is named 2019-01-11-Sequence-Listing-051039-094250USPX.txt and is 52,263 bytes in size.

TECHNICAL FIELD

The present invention relates to novel membrane nanostructures and their uses. In particular it relates to wide-channel membrane nanopores in the applications of protein sensing and molecular gate creation.

BACKGROUND

Nanopores are membrane spanning polymers and complexes that form a channel in a membrane through which ions and certain molecules may pass. The minimum diameter of the channel is typically in the nanometre ($10^{-9}$ metre) range hence giving certain of these polypeptides the name 'nanopores'.

Nanopores bound in membranes have many potential uses. One example is the use of nanopores as sensors to analyse biomolecules in a label-free and portable fashion. In an embodiment of this approach, an electrical potential is applied across a membrane-bound nanopore causing ions to flow through the channel. This flow of ions can be measured as an electrical current. Suitable electrical measurement techniques using single channel recording have been described, for example, in WO 2000/28312 and D. Stoddart et al., Proc. Natl. Acad. Sci., 2010, 106, 7702-7. Multichannel recording techniques have also been described, for example, in WO 2009/077734 and International Application WO-2011/067559. Optical measurements may be combined with electrical measurements (Soni G V et al., Rev Sci Instrum. 2010 January; 81(1):014301). Alternatively flow of ions through the membrane-bound nanopore may be achieved by providing an ionic gradient across the membrane.

Other potential uses are in the provision of functional interconnected networks of droplets joined by droplet interface bilayers containing nanopores that exploit a variety of membrane pumps, channels and pores to act as light sensors, batteries, and electrical devices (see for example Holden, M, A, et al, J. Am, Chem, Soc. 129, 8650-8655 (2007); 25 Maglia, G. et al. Nat. Nanotechnol, 4, 437-440 (2009)). Another use is the provision of droplet encapsulates and multisomes for use as drug delivery vehicles, such as disclosed by International Application PCT/GB2012/052736.

Individual molecules passing, binding or lodging inside a nanopore reduces the ion flow through the channel to yield an ion current read-out (see, for example, Liu X., Mihovilovic Skanata M., Stein D. Nat. Commun. 6, 6222 (2015); Lindsay S. Nat. Nanotechnol. 11, 109-111 (2016); Howorka S., Siwy Z. Chem. Soc. Rev. 38, 2360-2384 (2009); Wang Y., Zheng D., Tan Q., Wang M. X., Gu L. Q. Nat. Nanotechnol. 6, 668-674 (2011); and Wei R. S., Gatterdam V., Wieneke R., Tampe R., Rant U. Nat. Nanotechnol. 7, 257-263 (2012)). The degree of reduction in ion flow, as measured by the reduction in electrical current, is indicative of the size of the obstruction within, or in the vicinity of, the pore. The measured electrical current can therefore be used as a measure of the size or degree of obstruction to the channel. The changes in electrical current can be used to identify that a molecule, or part of a molecule, has bound at or near the pore (molecular sensing), or in certain systems, it can be used to determine the identity of a molecule that is present within the pore based on its size. This principle is used in nanopore based nucleic acid sequencing.

Adapting the sensing approach to specific analytes relies on nanopores of tailored structure. Prominent examples are the membrane pores MspA and α-hemolysin which have a protein structure and whose narrow lumen matches the size of DNA nucleotides and thus allow electrical sequencing of individual translocating DNA strands (Cherf G. M., Lieberman K. R., Rashid H., Lam C. E., Karplus K., Akeson M. Nat. Biotechnol. 30, 344-348 (2012); Manrao E. A., et al. Nat. Biotechnol. 30, 349-353 (2012); and Quick J., et al. Nature 530, 228-232 (2016)), or nucleotides (Clarke J., Wu H. C., Jayasinghe L., Patel A., Reid S., Bayley H. Nat. Nanotechnol. 4, 265-270 (2009)).

Expanding the powerful sensing principle to protein analytes of diagnostic or environmental importance that remain in their native folded state requires a different set of nanopores.

To be useful as a sensor for folded proteins or other large biomolecules, suitable membrane channels formed by a nanopore should meet certain criteria, namely:

1) the channel lumen should be at least about 5 nm wide to accommodate the large biomolecule molecules inside the channel lumen; binding of the large biomolecule within the channel results in higher read-out sensitivity than when analytes bind at the pore entrance;
2) the pores should be structurally defined to attain a constant base level in the electrical read-out (i.e. reduce background noise); and
3) the pore dimensions should be easily tunable to adapt them to different biomolecule sizes.

To date none of the existing biological or engineered pores fulfill all of these criteria.

In terms of potential protein pores, the narrow α-hemolysin pore can be tailored to achieve binding of selected proteins at the pore entrance (Movileanu L., Howorka S., Braha O., Bayley H. Nat. Biotechnol. 18, 1091-1095 (2000); Rotem D., Jayasinghe L., Salichou M., Bayley H. J. Am. Chem. Soc. 134, 2781-2787 (2012)) but this approach is not generic. Furthermore, perfringolysin and related pores have a diameter of at least 20 nm yet their size is heterogeneous (Dang T. X., Hotze E. M., Rouiller I., Tweten R. K., Wilson-Kubalek E. M. J. Struct Biol. 150, 100-108 (2005)). By comparison, ClyA has a defined width of 4.5 nm; its diameter is not easily tunable (Maglia G., Henricus M., Wyss R., Li Q., Cheley S., Bayley H. Nano Lett. 9, 3831-3836 (2009); Soskine M., Biesemans A., Maglia G. J. Am. Chem. Soc. 137, 5793-5797 (2015). Engineering protein pores de novo (Dang et al, ibid.) is not an option due to the difficulty of predicting the final outcome of folding polypeptides.

Sufficiently wide nanopores can also be fabricated from inorganic materials (see, for example, Wei R. S., Gatterdam V., Wieneke R., Tampe R., Rant U. *Nat. Nanotechnol.* 7, 257-263 (2012); Dekker C. *Nat. Nanotechnol.* 2, 209-215 (2007); Miles B. N., Ivanov A. P., Wilson K. A., Dogan F., Japrung D., Edel J. B. *Chem. Soc. Rev.* 42, 15-28 (2013); and Yusko E. C., et al. *Nat. Nanotechnol.* 6, 253-260 (2011)) but they are not compatible with hydrophobic membrane format that is standard for portable analytical nanopore devices (Quick J., et al. *Nature* 530, 228-232 (2016)).

Pores composed of nucleic acid duplexes, in particular DNA duplexes, represent another possibility for sensing nanopores. DNA nanopores have recently been obtained from a structural core of six hexagonally arranged, interlinked DNA duplexes that enclose a hollow channel (see, for example, Douglas S. M., Marblestone A. H., Teerapittayanon S., Vazquez A., Church G. M., Shih W. M. *Nucleic Acids Res.* 37, 5001-5006 (2009); Zheng J., et al. *Nature* 461, 74-77 (2009); Rothemund P. W. *Nature* 440, 297-302 (2006); Fu J., et al. *Nat. Nanotechnol.* 9, 531-536 (2014); Burns J. R., et al. *Angew. Chem. Int. Ed.* 52, 12069-12072 (2013); and Seifert A., Göpfrich K., Burns J. R., Fertig N., Keyser U. F., Howorka S. *ACS Nano* 9, 1117-1126 (2015)). Membrane insertion was achieved through equipping the pores exterior with hydrophobic lipid anchors. However, these pores have a narrow lumen of no more than 2 nm in diameter. Another drawback was structural instability leading to an 80% channel closure at standard experimental conditions of high transmembrane voltages (Zheng et al, ibid.).

The modular construction principle for DNA nanopores has enabled customized pore diameter (Göpfrich et al, *Nano. Lett.,* 15(5), 3134-3138 (2015); WO 2013/083983) and installation of a controllable gate to regulate transport (Burns J. R., Seifert A., Fertig N., Howorka S. A., *Nat. Nanotechnol.* 11, 152-156 (2016)).

A general challenge remains to insert the negatively charged polynucleotide, suitably DNA, nanostructures into hydrophobic layers, for example phospholipid bilayers, and this issue is expected to increase for nanopores of larger diameter.

There is therefore a need in the field for the provision of membrane-spanning nanopores that fulfil the above criteria of minimum diameter, structural definition and adaptability.

It is also desirable that such pores may be usable not only in biological phospholipid bilayers but also within the membranes which make up synthetic polymer vesicles, membranes or solid state substrates.

SUMMARY OF THE INVENTION

It is an object of the present invention to overcome or alleviate at least one of the above noted drawbacks of prior art systems or to at least provide a useful alternative to related art systems.

In a first aspect the invention relates to a membrane-spanning nanopore, comprising:
  i. at least one scaffold polynucleotide strand;
  ii. a plurality of staple polynucleotide strands; and
  iii. at least one hydrophobically-modified polynucleotide strand, wherein the hydrophobically-modified polynucleotide strand comprises a polynucleotide strand and a hydrophobic moiety;

wherein each of the plurality of staple polynucleotide strands hybridises to the at least one scaffold polynucleotide strand to form the three-dimensional structure of the membrane-spanning nanopore, and wherein the at least one hydrophobically-modified polynucleotide strand hybridises to a portion of the at least one scaffold polynucleotide strand,
  the membrane-spanning nanopore defining a central channel with a minimum internal width of at least about 5 nm.

Typically, the polynucleotide in the at least one scaffold strand, each of the plurality of staple polynucleotide strands, and the hydrophobically-modified polynucleotide strand comprises DNA. Suitably, the membrane-spanning nanopore of claim 2, wherein the assembly of the nanopore is via DNA origami techniques.

In an embodiment, the minimum internal width of the central channel of the nanopore is from about 5 nm to about 20 nm. Suitably, the minimum internal width of the central channel of the nanopore is from about 5 nm to about 10 nm. In an embodiment, the minimum internal width of the central channel of the nanopore is 7.5 nm.

In an embodiment, the nanopore comprises a membrane-spanning region and at least one cap region. Suitably, the membrane-spanning region is arranged to abut the at least one cap region. In embodiments wherein one cap region is present, the membrane-spanning region is located at one end of the nanopore.

In an embodiment, the membrane-spanning region has a dimension co-axial with the channel of about 1 nm to about 7 nm. Suitably, the membrane-spanning region has a dimension co-axial with the channel of about 3 nm to about 5 nm. In further embodiments, the cap region has a dimension co-axial with the channel of about 20 nm to about 70 nm. Suitably, the cap region has a dimension co-axial with the channel of about 40 nm to about 50 nm.

In an embodiment, the nanopore of the first aspect further comprises one or more adaptor polynucleotide strands, wherein the at least one hydrophobically-modified polynucleotide strand is hybridised to the nanopore via the one or more adaptor polynucleotide strands, the one of more adaptor polynucleotide strands each having a first end and a second end, wherein the first end of the adaptor polynucleotide strand hybridises with the at least one scaffold polynucleotide strand, and the second end of the adaptor polynucleotide strand hybridises with the at least one hydrophobically-modified polynucleotide strand. Suitably, the polynucleotide in the adaptor polynucleotide strands is DNA.

In an embodiment, the at least one hydrophobic moiety comprises a lipid. Suitably, the lipid is selected from the group consisting of: sterols; alkylated phenols; flavones; saturated and unsaturated fatty acids; and synthetic lipid molecules (including dodecyl-beta-D-glucoside. Typically, the sterols are selected from the group consisting of: cholesterol; derivatives of cholesterol; phytosterol; ergosterol; and bile acid; the alkylated phenols are selected from the group consisting of: methylated phenols; and tocopherols; the flavones are selected from the group consisting of: flavanone containing compounds; and 6-hydroxyflavone; the saturated and unsaturated fatty acids are selected from the group consisting of: derivatives of lauric acid; oleic acid; linoleic acid; and palmitic acids; and/or the synthetic lipid molecule is dodecyl-beta-D-glucoside.

In an embodiment, the nucleotide sequence of the scaffold strand comprises the DNA sequence of M13mp18 DNA (SEQ ID NO. 1). In further embodiments, the nucleotide sequences of the plurality of staple strands is selected from the group comprising SEQ ID Nos. 2 to 218. In still further embodiments, the nucleotide sequence of the one or more adaptor strands is selected from the group comprising SEQ ID Nos. 219 to 241, and in other embodiments, the sequence of the at least one hydrophobically-modified nucleotide strand is selected from the group comprising SEQ ID No. 242 or 243.

In an embodiment, the nanopore has a cross-section perpendicular to a longitudinal axis of the channel that is quadrilateral in shape. Suitably, the quadrilateral is a square. In another embodiment, the membrane-spanning nanopore is modified, wherein the central channel comprises one or more constrictions.

In a second aspect, the invention provides a membrane comprising one or more of the membrane-spanning nanopores of the first aspect of the invention.

In an embodiment of the second aspect, the membrane comprises a bilayer. The bilayer may be a lipid bilayer. Alternatively, the membrane comprises a semi-fluid membrane formed of polymers. Suitably, the polymer forming the semi-fluid membrane is composed of amphiphilic synthetic block copolymers. Typically, the amphiphilic synthetic block copolymers are composed of hydrophilic copolymer blocks and hydrophobic copolymer blocks. In embodiments, the hydrophilic copolymer blocks are selected from the group consisting of: poly(ethylene glycol) (PEG/PEO); and poly(2-methyloxazoline); and the hydrophobic copolymer blocks are selected from the group consisting of: polydimethylsiloxane (PDMS); poly(caprolactone (PCL); poly(lactide) (PLA); and poly(methyl methacrylate) (PMMA). Suitably, the polymer membrane is composed of the amphiphilic block copolymer poly 2-(methacryloyloxy) ethyl phosphorylcholine-b-disisopropylamino) ethyl methacrylate (PMPC-b-PDPA).

In an embodiment of the second aspect of the invention, the membrane is in the form of a vesicle, a micelle, a planar membrane or a droplet. The membrane may form a droplet interface bilayer or a droplet-droplet bilayer. In a further embodiment, the membrane comprises a solid state substrate.

In a third aspect of the invention, a biological sensor is provided, wherein the biological sensor comprises a membrane of the second aspect of the invention and apparatus for measuring an ion flow through or an electron flow across one or more membrane-spanning nanopores.

In a fourth aspect, the invention provides a biological sensing device comprising one or more biological sensors of the third aspect of the invention.

In a fifth aspect of the invention, there is provided a method for molecular sensing comprising:
  i. Providing the membrane according to the second aspect of the invention;
  ii. Contacting the nanopore with a test substrate and establishing a flow of ions through the nanopore or an electron flow across the nanopore; and
  iii. Measuring the ion flow through the nanopore or electron flow across one or more of the membrane-spanning nanopores.

In an embodiment of the fifth aspect, the flow of ions is from a first side of the membrane to a second side of the membrane. In a further embodiment, the molecular sensing is analyte detection or characterisation, wherein the change in ion flow or electron flow is indicative of the analyte.

In a further embodiment of the fifth aspect of the invention, the method comprises after step (iii) the further step of determining the presence of the test substrate by a change in ion flow or electron flow through or across the membrane compared to the ion flow or electron flow through or across the membrane when the test substrate is absent.

In an embodiment, the test substrate is a globular protein, a polynucleotide-protein construct, a labelled polynucleotide or a labelled protein.

The sensing apparatus suitable for use in the fifth aspect (and other aspects as appropriate) of the present invention, may comprise a measurement system arranged as disclosed in any of WO 2008/102210, WO 2009/07734, WO 2010/122293, WO 2011/067559 or WO 2014/04443. The sensing apparatus may comprise electrodes arranged on each side of the membrane in order to measure an ion current through an aperture under a potential difference. The electrodes may be connected to an electrical circuit which includes a control circuit arranged to supply a voltage to the electrodes and a measurement circuit arranged to measure the ion flow. A common electrode may be provided to measure ion flow through the apertures between the common electrode and electrodes provided on the opposite side of the membrane.

Fluid chambers provided on either side of the nanopore array may be referred to as the cis and trans chambers. The molecular entity to be determined by the array of nanopores is typically added to the cis chamber comprising the common electrode. Separate trans chambers may be provided on the opposite side of the array, each trans chamber comprising an electrode wherein ion flow through each aperture is measured between an electrode of the trans chamber and the common electrode.

Alternative or additional measurements associated with movement of the molecular entity with respect to the aperture may be carried out, such as measurement of a tunnelling current across the aperture (Ivanov A P et al., Nano Lett. 2011 Jan. 12; 11(1):279-85), or a field effect transistor (FET) device, such as disclosed by WO 2005/124888, U.S. Pat. No. 8,828,138, WO 2009/035647, or Xie et al, Nat Nanotechnol. 2011 Dec. 11; 7(2): 119-125. The measurement device may be an FET nanopore device comprising source and drain electrodes to determine the presence or passage of a molecular entity in the apertures. An advantage of employing an FET nanopore device, namely one employing FET measurements across the apertures to measure a local potential or capacitance, or one employing measurement of a tunnelling current across the aperture, is that the measurement signal is very local to a particular aperture and therefore a device comprising a shared trans chamber may be employed. This greatly simplifies the construction of the device without the need to provide separate trans chambers for each aperture, such as one for the measurement of ion flow through the apertures, as described above. As a result, very high densities of apertures in the array may be conveniently provided, for example an array comprising apertures having a pitch of less than 10 nm and a density of 106 apertures/cm$^2$.

In a sixth aspect of the invention, a method for molecular gating is provided, the method comprising:
  i. Providing the membrane according to the second aspect of the invention;
  ii. Providing at least one biomolecule with a diameter of less than the minimum internal width of a channel in the nanopore; and
  iii. Incubating until the at least one biomolecule has passed through the nanopore.

In an embodiment of the sixth aspect of the invention, when at least one biomolecule has passed through the nanopore, it is subjected to a physical change that prevents it returning through the nanopore.

In embodiments, the at least one biomolecule is a globular protein, a polynucleotide-protein construct, a labelled polynucleotide or a labelled protein.

A seventh aspect of the invention provides a membrane-spanning nanopore, comprising:
  i. at least one scaffold nucleotide strand comprising at least one hydrophobic anchor, wherein the hydrophobic anchor comprises a polynucleotide strand and a hydrophobic moiety; and
  ii. a plurality of staple polynucleotide strands;
  wherein each of the plurality of staple polynucleotide strands hybridises to the at least one scaffold polynucleotide strand to form the three-dimensional structure of the membrane-spanning nanopore,
  the membrane-spanning nanopore defining a central channel with a minimum internal width of at least about 5 nm.

In an embodiment of the seventh aspect, the polynucleotide in the at least one scaffold strand, each of the plurality of staple polynucleotide strands, and the hydrophobic anchor comprises DNA.

BRIEF DESCRIPTION OF THE DRAWINGS

FIG. 3 shows results of confirming the assembly, purity, dimensions and membrane-interaction properties of DNA nanopores. (A) Gel electrophoretic analysis of scaffold strand (ss) and nanopores $NP^{-C}$, and NP without and with detergent SDS. The position and bp length of the dsDNA markers in kbp is given at the sides of the electropherograms. (B) AFM micrographs (top) and elevation profiles (bottom) of $NP^{-C}$ that assembled on mica into chains. In the micrographs, pores appear as squares due to the compression of the hollow DNA nanostructure by the AFM cantilever. The scale bar for micrographs is 250 and 100 nm for top and bottom images, respectively, and the vertical scale is from 0 to 14 nm for both images. The AFM elevation profiles show the dimensions of the five DNA nanopores in the bottom AFM image. (C) Gel electropherogram of NP and $NP^{-C}$ incubated with no (leftmost lane) or increasing amounts of SUV membrane vesicles ranging from 6.9 to 12.5 nM. The upshifted bands of lipid anchor-bearing NP indicate interaction with bilayer membranes. The interaction does not occur for anchor-free $NP^{-C}$. The right-most band is weaker as half the amount of DNA was loaded. The position of the two dsDNA markers with a length of 10 and 1 kbp are given at the right of the gels.

FIG. 3 shows size exclusion chromatography trace of an assembly mixture containing the folded DNA nanopore (elution volume of 7.88 mL) and excess staple strands (elution volume of 16.13 mL). Absorption was determined at 260 nm.

DETAILED DESCRIPTION

Figure 1A:
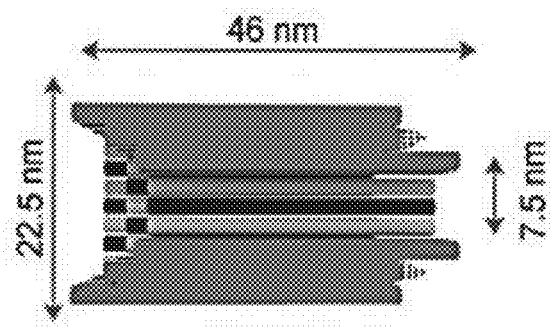
FIG. 1 shows a design of a large membrane-spanning DNA nanopore designated as NP. (A) The membrane-embedded pore is composed of squarely arranged DNA duplexes which are illustrated as light grey and dark grey cylinders. The latter carry cholesterol lipid anchors (hatched shading) for membrane insertion. Protein trypsin (not shown) can pass via the pore from the cis to the trans side of the membrane. (B) Top-down and side view of the nanopore. (C) Cross-sectional side view to show the geometry of the pore lumen with the dimensions annotated.

Prior to setting forth the invention, a number of definitions are provided that will assist in the understanding of the invention. All references cited herein are incorporated by reference in their entirety. Unless otherwise defined, all technical and scientific terms used herein have the same meaning as commonly understood by one of ordinary skill in the art to which this invention belongs.

Unless otherwise indicated, the practice of the present invention employs conventional techniques of chemistry, molecular biology, microbiology, recombinant DNA technology, and chemical methods, which are within the capabilities of a person of ordinary skill in the art. Such techniques are also explained in the literature, for example, M. R. Green, J. Sambrook, 2012, Molecular Cloning: A Laboratory Manual, Fourth Edition, Books 1-3, Cold Spring Harbor Laboratory Press, Cold Spring Harbor, N.Y.; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridisation: Principles and Practice, Oxford University Press; M. J. Gait (Editor), 1984, Oligonucleotide Synthesis: A Practical Approach, IRL Press; and D. M. J. Lilley and J. E. Dahlberg, 1992, Methods of Enzymology: DNA Structure Part A: Synthesis and Physical Analysis of DNA Methods in Enzymology, Academic Press. Each of these general texts is herein incorporated by reference.

As used herein, the term 'comprising' means any of the recited elements are necessarily included and other elements may optionally be included as well. 'Consisting essentially of' means any recited elements are necessarily included, elements that would materially affect the basic and novel characteristics of the listed elements are excluded, and other elements may optionally be included. 'Consisting of' means that all elements other than those listed are excluded. Embodiments defined by each of these terms are within the scope of this invention.

The term 'membrane' as used herein is an enclosing or separating selectively-permeable boundary, partition, barrier or film. The membrane has two sides or surfaces which may be named the cis and trans side respectively. The membrane is thin (i.e. has a thickness substantially less than its width and length) allowing it to be spanned by the nanopore. In the context of the present invention, the membrane thickness is the typically in the nanometre ($10^{-9}$ metre) range. The arrangement of the membrane is not limited and may in any form, for example, a liposome, vesicle or as a planar or a non-planar sheet. Specific examples of membranes useful in the present invention include lipid bilayers, polymeric films, or solid state substrates.

The term 'solid state membrane' or 'solid state substrate' as used herein refers to a membrane formed from a solid state substance in which one or more apertures are provided. One or more nanopores may be positioned within the respective one or more apertures disclosed for example in U.S. Pat. No. 8,828,211, hereby incorporated by reference. The solid state membrane may comprise either or both of organic and inorganic materials, including, but not limited to, microelectronic materials, whether electrically conducting, electrically semiconducting, or electrically insulating, including materials such as II-IV and III-V materials, oxides and nitrides, such as silicon nitride, $Al_2O_3$, and $SiO_2$, Si, $MoS_2$, solid state organic and inorganic polymers such as polyamide, plastics such as Teflon®, or elastomers such as two-component addition-cure silicone rubber, and glasses. A membrane may be formed from monatomic layers, such as graphene, or layers that are only a few atoms thick such as those disclosed in U.S. Pat. No. 8,698,481, and U.S. Patent Application Publication 2014/174927, both hereby incorporated by reference. More than one layer of material can be included, such as more than one graphene layer, as disclosed in US Patent Application Publication 2013/309776, incorporated herein by reference. Suitable silicon nitride membranes are disclosed in U.S. Pat. No. 6,627,067, and the membrane may be chemically functionalized, such as disclosed in U.S. Patent Application Publication 2011/053284, both hereby incorporated by reference. Such a structure is disclosed for example in U.S. Pat. No. 8,828,211, hereby incorporated by reference. The internal walls of the apertures may be coated with a functionalised coating, such as disclosed in published application WO 2009/020682. The one or more apertures may be hydrophobic or provided with a hydrophobic coating to assist the provision of the one or more nanopores in the respective one or more apertures. Suitable methods for providing apertures in solid state substrates are disclosed in published applications WO 03003446 and WO 2016/187519.

The term 'nucleic acid' as used herein, is a single or double stranded covalently-linked sequence of nucleotides in which the 3' and 5' ends on each nucleotide are joined by phosphodiester bonds. The polynucleotide may be made up of deoxyribonucleotide bases or ribonucleotide bases. Nucleic acids may include DNA and RNA, and are typically manufactured synthetically, but may also be isolated from natural sources. Nucleic acids may further include modified DNA or RNA, for example DNA or RNA that has been methylated or that has been subject to chemical modification, for example 5'-capping with 7-methylguanosine, 3'-processing such as cleavage and polyadenylation, and splicing, or labelling with fluorophores or other compounds.

Nucleic acids may also include synthetic nucleic acids (XNA), such as hexitol nucleic acid (HNA), cyclohexene nucleic acid (CeNA), threose nucleic acid (TNA), glycerol nucleic acid (GNA), locked nucleic acid (LNA) and peptide nucleic acid (PNA). Hence, where the terms 'DNA' and 'RNA' are used herein it should be understood that these terms are not limited to only include naturally occurring nucleotides. Sizes of nucleic acids, also referred to herein as 'polynucleotides' are typically expressed as the number of base pairs (bp) for double stranded polynucleotides, or in the case of single stranded polynucleotides as the number of nucleotides (nt). One thousand bp or nt equal a kilobase (kb). Polynucleotides of less than around 100 nucleotides in length are typically called 'oligonucleotides'.

As used herein, the terms '3" ('3 prime') and '5" ('5 prime') take their usual meanings in the art, i.e. to distinguish the ends of polynucleotides. A polynucleotide has a 5' and a 3' end and polynucleotide sequences are conventionally written in a 5' to 3' direction. The term 'complements of a polynucleotide molecule' denotes a polynucleotide molecule having a complementary base sequence and reverse orientation as compared to a reference sequence.

The term 'duplex' is used herein refers to double-stranded DNA, meaning that the nucleotides of two complimentary DNA sequences have bonded together and then coiled to form a double helix.

According to the present invention, homology to the nucleic acid sequences described herein is not limited simply to 100% sequence identity. Many nucleic acid sequences can demonstrate biochemical equivalence to each other despite having apparently low sequence identity. In the present invention homologous nucleic acid sequences are considered to be those that will hybridise to each other under conditions of low stringency (Sambrook J. et al, supra).

As used herein, the term 'nanostructure' refers to a predesigned two or three dimensional molecular structure typically comprised from a biopolymer, suitably a naturally or non-naturally occurring nucleic acid, which structure has at least one dimension or an aspect of its geometry that is within the nanoscale (i.e. $10^{-9}$ metres). Nanoscale structures suitably have dimensions or geometry of less than around 100 nm, typically less than 50 nm, and most suitably less than 20 nm. Nanoscale structures suitably possess dimensions or geometry greater than around 0.1 nm, typically greater than around 1 nm, and optionally greater than around 2 nm. Assembly of nucleic acid nanostructures may occur spontaneously in solution, or may require presence of additional co-factors including, but not limited to, nucleic acid scaffolds, nucleic acid aptamers, nucleic acid staples, co-enzymes, and molecular chaperones. Where desired nanostructures result from one or more predesigned spontaneously self-folding nucleic acid molecules, such as DNA, this is typically referred to as nucleic acid 'origami'. Exemplary three dimensional DNA nanostructures may comprise nanobarrels; nanorafts, which are typically rectangular, polygonal, circular, or ellipsoid substantially planar nanostructures; nanospheres and regular or irregular polyhedral nanostructures, including stellated polyhedral nanostructures. Exemplary two dimensional DNA nanostructures may comprise nanodiscs or nanoplates. Rational design and folding of DNA to create two dimensional or three dimensional nanoscale structures and shapes is known in the art (e.g. Rothemund (2006) Nature 440, 297-302).

The nucleic acid sequences that form the nanostructures will typically be manufactured synthetically, although they may also be obtained by conventional recombinant nucleic acid techniques. DNA constructs comprising the required sequences may be comprised within vectors grown within a microbial host organism (such as *E. coli*). This would allow for large quantities of the DNA to be prepared within a bioreactor and then harvested using conventional techniques. The vectors may be isolated, purified to remove extraneous material, with the desired DNA sequences excised by restriction endonucleases and isolated, such as by using chromatographic or electrophoretic separation.

The term 'amino acid' in the context of the present invention is used in its broadest sense and is meant to include naturally occurring L α-amino acids or residues. The commonly used one and three letter abbreviations for naturally occurring amino acids are used herein: A=Ala; C=Cys; D=Asp; E=Glu; F=Phe; G=Gly; H=His; 1=Ile; K=Lys; L=Leu; M=Met; N=Asn; P=Pro; Q=Gln; R=Arg; S=Ser; T=Thr; V=Val; W=Trp; and Y=Tyr (Lehninger, A. L., (1975) Biochemistry, 2d ed., pp. 71-92, Worth Publishers, New York). The general term 'amino acid' further includes D-amino acids, retro-inverso amino acids as well as chemically modified amino acids such as amino acid analogues, naturally occurring amino acids that are not usually incorporated into proteins such as norleucine, and chemically synthesised compounds having properties known in the art to be characteristic of an amino acid, such as β-amino acids. For example, analogues or mimetics of phenylalanine or proline, which allow the same conformational restriction of the peptide compounds as do natural Phe or Pro, are included within the definition of amino acid. Such analogues and mimetics are referred to herein as 'functional equivalents' of the respective amino acid. Other examples of amino acids are listed by Roberts and Vellaccio, The Peptides: Analysis, Synthesis, Biology, Gross and Meiehofer, eds., Vol. 5 p. 341, Academic Press, Inc., N.Y. 1983, which is incorporated herein by reference.

A 'polypeptide' is a polymer of amino acid residues joined by peptide bonds, whether produced naturally or in vitro by synthetic means. Polypeptides of less than around 12 amino acid residues in length are typically referred to as 'peptides' and those between about 12 and about 30 amino acid residues in length may be referred to as 'oligopeptides'. The term 'polypeptide' as used herein denotes the product of a naturally occurring polypeptide, precursor form or proprotein. Polypeptides can also undergo maturation or post-translational modification processes that may include, but are not limited to: glycosylation, proteolytic cleavage, lipidization, signal peptide cleavage, propeptide cleavage, phosphorylation, and such like. The term 'protein' is used herein to refer to a macromolecule comprising one or more polypeptide chains.

The term 'folded protein' as used herein refers to a protein that has acquired some three-dimensional shape after translation of the polypeptide chain from which it is formed (the primary structure). The term may refer to the secondary structure of the protein which is typically the first stage of the folding process where local three-dimensional structures are formed, for example, alpha helices or beta sheets. The term may more typically refer to the tertiary structure of a protein where the secondary structures of the protein have folded to stabilise the structure through hydrophobic or covalent interactions. The term also encompasses proteins having a quaternary structure where one or more protein subunits are assembled. As appropriate, the folded protein may also be termed the 'native' protein structure, and may be the form of the protein that exhibits its biological function.

The term 'interior width' when used herein refers to the straight distance spanning the interior of the channel from an interior face of one wall to an interior face of an opposing wall in a plane perpendicular to the longitudinal axis of the channel. The interior width of the channel may be constant along its longitudinal axis or it may vary. The 'minimum interior width' is the minimum interior width along the longitudinal axis of the channel between an entrance and an exit of the channel. The minimum interior width of a channel defines the maximum size of an object that may pass through the channel.

As used herein the term 'hydrophobic' refers to a molecule having a polar character including organic molecules and polymers. Examples are saturated or unsaturated hydrocarbons. The molecule may have amphipathic properties.

As used herein, the term 'hydrophobically-modified' relates to the modification (joining, bonding or otherwise linking) of a polynucleotide strand with one or more hydrophobic moieties. A 'hydrophobic moiety' as defined herein is a hydrophobic organic molecule. The hydrophobic moiety may be any moiety comprising non-polar or low polarity aliphatic, aliphatic-aromatic or aromatic chains. Suitably, the hydrophobic moieties utilised in the present invention encompass molecules such as long chain carbocyclic molecules, polymers, block co-polymers, and lipids. The term 'lipids' as defined herein relates to fatty acids and their derivatives (including tri-, di-, monoglycerides, and phospholipids), as well as sterol-containing metabolites such as cholesterol. The hydrophobic moieties comprised within the embodiments of the present invention are capable of forming non-covalent attractive interactions with phospholipid bilayers, such as the lipid-based membranes of cells and act as membrane anchors for the nanopore. According to certain embodiments of the present invention suitable hydrophobic moieties, such as lipid molecules, possessing membrane anchoring properties may include sterols (including cholesterol, derivatives of cholesterol, phytosterol, ergosterol and bile acid), alkylated phenols (including methylated phenols and tocopherols), flavones (including flavanone containing compounds such as 6-hydroxyflavone), saturated and unsaturated fatty acids (including derivatives such as lauric, oleic, linoleic and palmitic acids), and synthetic lipid molecules (including dodecyl-beta-D-glucoside). The anchors for the polymer membrane may be the same as for lipid bilayers or they may be different. The specific hydrophobic moiety anchor may be selected based on the binding performance of the membrane chosen.

The inventors have identified a structurally-defined wide-channel organic nanopore. The structure of the nanopore renders it suitable for a number of uses. One such use is biomolecule sensing applications, in particular protein sensing applications where the folded protein may pass, bind or lodge within the pore. Modified versions of the nanopore may serve to further enhance the suitability of the channel for a particular folded protein or other biomolecule. Biomolecule sensing may be enhanced by the installation of a molecular receptor within the pore lumen or channel.

The wide channel DNA nanopore according to the present invention offers an advantage over existing protein pores such as ClyA or alpha-hemolysin, and known DNA nanopores. The nanostructure provides a wide, stable membrane-spanning channel that allows folded proteins, typically proteins that have a three-dimensional tertiary or quaternary structure, to pass, bind or lodge within. Passing or binding a folded protein in the channel of a nanopore leads to an improved read-out signal through more effective blockade of the ion flow through the open channel, as compared to binding of the protein at the mouth of the channel.

While DNA pores are, by their nature, more negatively charged than usual protein pores. Potential electrostatic repulsion of cargo, if it were to occur, could be compensated by higher ionic strength or charge-neutralized DNA (Burns J., Stulz E., Howorka S. Self-assembled DNA nanopores that span lipid bilayers. Nano Lett. 13, 2351-2356 (2013)).

The wide opening of the channel of the nanopore also facilitates the translocation of folded proteins and large biomolecules through a polymer membrane leading to potential applications of the nanopores in molecular gating of biomolecules. Recently developed synthetic membrane-spanning DNA nanopores provide a new and potentially generic route for controlled transport across membranes (see, for example, Douglas S. M., Marblestone A. H., Teerapittayanon S., Vazquez A., Church G. M., Shih W. M. Nucleic Acids Res. 37, 5001-5006 (2009); Zheng J., et al. Nature 461, 74-77 (2009); Fu J., et al. Nat. Nanotechnol. 9, 531-536 (2014); Burns J. R., et al. Angew. Chem. Int. Ed. 52, 12069-12072 (2013); and Seifert A., Gopfrich K., Burns J. R., Fertig N., Keyser U. F., Howorka S. ACS Nano 9, 1117-1126 (2015)).

The ability to create nanopores with controlled pore sizes and insert them into natural or synthetic membranes allows the construction of customised selectively-permeable membranes where control over the lumen dimensions, and optionally, other features of the pores enables control over which biomolecules are able to pass through these membranes. Of particular utility in the present invention is the increased size of the nanopores of the present invention that allows large biomolecules, including large globular proteins, to pass through such membranes which has not been possible to date. This has potential utility in medicine alongside other uses in the field of biology. For example, there are several large i.e. 10-30 nm diameter membrane pores that are either produced by immune cells to kill bacteria, such as in the 'complement system' (a part of the innate immune system that enhances (complements) the ability of antibodies and phagocytic cells to clear microbes and damaged cells from an organism, promotes inflammation, and attacks the pathogen's plasma membrane). In particular to the C9 protein forms a large pore that together with other accessory proteins forms the membrane attack complex. Membrane poration is also used by pathogenic bacteria to attack and kill eukaryotic host cells. Examples of these bacterial pores are Cholesterol-dependent Cytolysin which includes perfrinoglysin or listeriolysin O.

As an example, vesicles formed of natural or synthetic polymers comprising nanopores according to the present invention may be used as nanoreactors. It is envisaged that substrate proteins or biomolecules may enter the vesicle interior through the nanopore where encapsulated enzymes in the interior of the vesicle enable a desired reaction to take place within the vesicle. As an example, encapsulated protease enzymes, such as trypsin may be retained inside a vesicle where the relatively large and controllable size of the nanopores could allow some substrate proteins but not others to enter for degradation, thereby protecting particular proteins from indiscriminate digestion. Similarly, control over the release of cargo contained within similar vesicles, such as protein or peptide based pharmaceutical agents would be possible with membranes with nanopores which allow passage of the cargo.

According to an embodiment of the present invention, there is provided novel nucleic acid nanopores that have a central channel or lumen with a relatively large minimum diameter (for example, greater than about 5 nm) surrounded and defined by a generally elongate cylindrical pore wall. As described herein, the nanopores are structurally defined and are tunable to permit adaption to different pore channel sizes. The pores may be composed of any suitable nucleic acids. Nanopores formed from one or more DNA duplexes are particularly suitable as they are an excellent construction material for rationally designing nanoscale architectures of defined size (Langecker M., et al. *Science* 338, 932-936 (2012); Burns J., Stulz E., Howorka S. *Nano Lett.* 13, 2351-2356 (2013); Burns J. R., Al-Juffali N., Janes S. M., Howorka S. *Angew. Chem. Int. Ed.* 53, 12466-12470 (2014); Burns J. R., Seifert A., Fertig N., Howorka S. *Nat. Nanotechnol.* 11, 152-156 (2016)).

The nanopore may be designed to have any suitable shape, although generally it has an elongated cylindrical shape. The dimensions of the nanopore are determined to a degree by the length of the scaffold strand used, the number of layers of nucleic acid duplex used to line the pore and the height of the pore. For example, for a three-layer square nanopore design based on the use of the scaffold strand M13mp18 that is 7249 bases long, a pore may be designed with a minimum internal width or opening of approximately 40 nm, and a diagonal width of 57 nm. In an alternative possible design, using the same scaffold strand M13mp18, a nanopore having a maximum length of 310 nm although the minimum internal width in only 2.5 nm, and therefore outside the scope of this invention.

The nanopore according to an embodiment of the present invention comprises two regions: a cap region and a membrane-spanning region. The membrane-spanning region is defined as the portion of the nanopore located within the plane of the membrane, and the cap region being the portion of the nanopore attached to the membrane-spanning region and extending away from the surface of the membrane. The nanopore may have a cap region on one side of the membrane only, or alternatively, have two cap regions, one on each side of the membrane. When there is more than one cap region, these may be the same as each other or they may be different. Suitably, the nanopore has one cap region on one side of the membrane forming an entrance to the nanopore.

The cap region may have dimensions of any suitable size. While it is possible for the cap region to extend only negligibly from the membrane surface, typically, the cap region has a height extending from the membrane of at least 5 nm as measured by the perpendicular distance from the membrane surface to the top of the pore wall. Suitably, the cap region may have a height of at least 10 nm, 15 nm, 20 nm, 25 nm, 30 nm, 35 nm, 40 nm, 45 nm or 50 nm or above. Suitably, the height of the cap region is at most 100 nm, 90 nm, 80 nm, 70 nm, 60 nm, or 50 nm or below. The height of the cap region may be determined by the length of the scaffold polynucleotide used, and the number of layers of polynucleotide duplexes that form the pore. For example, according to calculations using computer software (CaDNAno software, available at http://www.cadnano.org), for a square cross-section DNA pore using M13mp18 scaffold strand and with a minimum interior width of the pore of 20 nm, the maximum height of the pore is around 37 nm when the pore wall is two duplexes thick; 20 nm when the pore wall is three duplexes thick; and 13 nm when the pore is four duplexes thick.

The membrane-spanning region may have dimensions of any suitable size. Typically, the membrane-spanning region has a height that approximately matches the thickness of the membrane in which it resides. The thickness of biological lipid bilayer membranes can range from around 3.5 to 10 nm. The thickness of membrane composed of amphiphilic synthetic block copolymers shows a wider range from 5 to 50 nm (C. LoPresti, H. Lomas, M. Massignani, T. Smart, G. Battaglia, J. Mater. Chem. 2009, 19, 3576-3590). Therefore suitably, the membrane-spanning region may have a height of at least around 3.5 nm, although it may be possible to have a membrane-spanning region with a height as low as 3 nm, 2.5 nm, 2 nm 1.5 nm or 1.0 nm or less. Suitably, the membrane-spanning region may have a height of at least 5 nm. The membrane-spanning region may have a height of at most 100 nm, 90 nm, 80 nm, 70 nm, 60 nm, 50 nm, 40 nm, 30 nm, 20 nm or 10 nm or less. Suitably the membrane-spanning region has a maximum height of 50 nm for synthetic polymer layers, and a maximum height of 10 nm for lipid bilayers.

The channel or lumen that passes through the nanopore has a cross-sectional profile parallel to the membrane and perpendicular to a longitudinal axis of the channel. This cross-sectional profile may be of any shape and dimensions. The shape and dimensions of the channel may be consistent for its entire length or may vary. Suitably, the channel has a consistent cross-sectional profile and size for its entire length. Suitably, the cross-sectional profile of the channel is a quadrilateral, typically a square, or at least generally circular. The minimum opening or width of the channel in this cross-section is suitable to allow access for a folded protein. Typically, the minimum opening or width of the channel is at least 5 nm, 6 nm, 6.5 nm, 7 nm, 7.5 nm, 8 nm, 8.5 nm, 9 nm, 9.5 nm, 10 nm, 11 nm, 12 nm, 13 nm, 14 nm, 15 nm, 16 nm, 17 nm, 18 nm, 19 nm, 20 nm, 25 nm or more. Suitably the opening is between around 5 nm and around 20 nm. Typically the opening is around 5 nm and around 10 nm. The maximum opening of the channel is limited only by the need to maintain structural integrity of the pore and to obtain an electrical read-out when a molecule of interest passes through. Suitably, the maximum width or opening of the channel is 50 nm, 45 nm, 40 nm, 35 nm, 30 nm, 25 nm, 20 nm, 18 nm, 15 nm, 12 nm, or 10 nm. Suitably, the cross-sectional area of the minimum opening of the channel is at least 20 $nm^2$, 25 $nm^2$, 30 $nm^2$, 35 $nm^2$, 40 $nm^2$, 45 $nm^2$, 50 $nm^2$, 60 $nm^2$, 70 $nm^2$, 80 $nm^2$, 90 $nm^2$ or 100 $nm^2$ or more. Suitably, the cross-sectional area of the minimum opening of the channel is at most 200 $nm^2$, 180 $nm^2$, 160 $nm^2$, 140 $nm^2$, 120 $nm^2$, 100 $nm^2$, 90 $nm^2$, 80 $nm^2$, 70 $nm^2$, 60 $nm^2$, 50 $nm^2$, 40 $nm^2$, 30 $nm^2$, 20 $nm^2$ or 15 $nm^2$ or less.

To achieve optimum performance, the variation in the channel size should be minimized from pore to pore. Even small variation in surface area can lead to a significant discrepancy in ion flow through a given pore, both in the open state (devoid of any target analyte), or in the bound state (with target analyte present in, or proximate to, the channel). Such variation in ion flow leads to a lower signal to noise ratio in the electrical read-out thereby reducing the sensitivity of detection. The nanopores according to the present invention have low variability in pore size (see FIGS. 12 to 14).

The nanopore may be modified in order to provide one or more constrictions. The constriction may restrict the channel width. The constriction may restrict the channel width from between about 0.5 nm up to the width of the channel. A constriction is a narrowing of the channel width and more than one constriction may be provided along the length of the channel. The channel may be provided for example with two such constrictions. The constrictions may be spaced apart. The constrictions may be spaced apart from each other by 1 nm or more, for example spaced apart by a value between 1 nm and 20 nm, more particularly 5 and 10 nm. The modification may be chemical. A modification may be made after assembly of the nanopore. Alternatively modification may be made to the scaffold and/or staple strands prior to assembly of the nanopore. Examples of chemical modifications to protein nanopores in order to narrow the channel diameter are described in PCT/GB2017/050961.

Suitably, the nanopores of the present invention are assembled via the 'scaffold-and-staple' approach. In this important route to nucleic acid nanostructure, in particular, DNA nanostructures, DNA is utilized as a building material in order to make nanoscale three dimensional shapes. Assembly of these complex nanostructures from a plurality of un-hybridized linear molecules is typically referred to as 'DNA origami', although the technique is equally applicable to other nucleic acids.

The DNA origami process generally involves the folding of the one or more elongate, 'scaffold' DNA strands into a particular shape using a plurality of rationally designed 'staple' DNA strands. The scaffold strand can have any sufficiently non-repetitive sequence. There are many DNA sequences that are suitable for use as a scaffold sequences. Commercially available examples include single stranded scaffold DNA sequences named according to their base length, for example, P7249 (base sequence as in M13mp18; 7249 bases); type p7560 (7560 bases); p8064 (8064 bases) available from, for example, Eurofins Genomics (https://www.eurofinsgenomics.eu/en/dna-rna-oligonucleotides/oligo-design-more/dna-origami/scaffold-dna.aspx; accessed 13 Jul. 2017). The sequences of the staple strands are designed such that they hybridize to particular defined portions of the scaffold strands and, in doing so, force the scaffold strands to assume a particular configuration. Methods useful in the making of DNA origami structures can be found, for example, in Rothemund, P. W., Nature 440:297-302 (2006); Douglas et al, Nature 459:414-418 (2009); Dietz et al, Science 325:725-730 (2009); and U.S. Pat. App. Pub. Nos. 2007/0117109, 2008/0287668, 2010/0069621 and 2010/0216978, each of which is incorporated by reference in its entirety. Staple sequence design can be facilitated using, for example, CaDNAno software, available at http://www.cadnano.org.

In the context of the present invention, the sequences of the staple strands are selected such that the polynucleotide, suitably DNA, nanostructure assumes a shape or configuration that corresponds to a membrane-spanning nanostructure. In some embodiments, the staple strands of the DNA nanostructure are selected such that the DNA nanostructure is substantially channel- or tube-shaped.

In such embodiments, the inner surface of the DNA nanostructure is the surface on the inside of the tube—i.e. within the interior of the membrane spanning channel—while the outer surface of the DNA nanostructure is the outside of the tube.

In some embodiments, the scaffold strands of the DNA nanostructure are selected such that the membrane-spanning nanostructure has a first DNA duplex domain and second or further DNA duplex domains, wherein a first end of a first domain is attached to a first end of a second or further domain by one or more single-stranded DNA hinges or cross-over sequences, or simply 'cross-overs'. (Burns J. R., et al. *Angew. Chem. Int. Ed.* 52, 12069-12072 (2013); Burns J. R., Al-Juffali N., Janes S. M., Howorka S. *Angew. Chem. Int. Ed.* 53, 12466-12470 (2014); and Yang Y., Zhao Z., Zhang F., Nangreave J., Liu Y., Yan H. *Nano Lett.* 13, 1862-1866 (2013)). The cross-overs can be simple single-stranded DNA loops that connect two DNA duplexes such as at the termini of the two duplexes. Cross-over also includes structures where two DNA duplexes are interlinked by two strands at the same site. This type of cross-over is called a Holliday junction. A Holliday junction is a branched nucleic acid structure that contains four double-stranded arms joined together. A Holliday junction may be in the form of a cross, however in the case of DNA nanostructures, the four arms of the cross are more parallel whereby each two arms on one side form a duplex. A reference for cross-overs in DNA nanotech structures is Seeman, N. C., Annu. Rev. Biochem. 79, 65-87 (2010).

The nanopore of the present invention may comprise one or more hydrophobic moieties that act as anchors to attach or connect or anchor the hydrophilic DNA nanopore to the generally hydrophobic membrane (lipid bilayer, polymer or solid state). The hydrophobic anchors are attached to the pore. Suitably attachment is via polynucleotides, suitably DNA polynucleotide strands that carry the hydrophobic moiety, suitably a lipid such as cholesterol, at the 5' or 3' terminus. These hydrophobically-modified anchor strands hybridize via 'adaptor' polynucleotide strands to corresponding sections of the polynucleotide sequence forming the scaffold section of the pore. Alternatively, the hydrophobic anchors are assembled with the pore using hydrophobically-modified polynucleotides. The number of hydrophobically-modified anchors on a single pore is not limited and may number 20, 19, 18, 17, 16, 15, 14, 13, 12, 11, 10, 9, 8, 7, 6, 5, 4, 3, 2 or 1. Cholesterol has been found to be a particularly suitable hydrophobic moiety for use as an anchor in the present invention.

The use of other lipids as anchors is contemplated, although it may be expected that there is a particular preference for a particular hydrophobic moiety, and a given number of hydrophobic anchors, for a given membrane.

The membrane in which the nanopore of the present invention may be inserted may be of any suitable type. Depending on the intended use, the membrane may a lipid bilayer or a polymer sheet or film or a solid state substrate. In solid state membranes, the substrate may already comprise apertures in which the nanopore sits thereby adapting the interior dimensions and channel width of the aperture. The membrane is typically hydrophobic to promote anchoring by the hydrophobic anchors.

Lipid bilayers are ubiquitous in biological organisms. It is envisaged that nanopores according to the present invention may be inserted into a lipid membrane of a target cell or vesicle to facilitate translocation of specific folded proteins across the membrane. The specificity of the translocation to certain folded proteins may be controlled through variation of the size of the channel in the nanopore.

Proprietary and non-proprietary synthetic polymer films or sheets are widely used in 'chip-based' nanopore sequencing and analytical applications such as the MinION® system sold by Oxford Nanopore Technologies®; the GS FLX+® and the GS Junior® System sold by Roche®; the HiSeq®, Genome Analyzer IIx®, MiSeq® and the HiScanSQ® systems sold by Illumina®; the Ion PGM® System and the Ion Proton System® sold by Life Technologies; the CEQ® system sold by Beckman Coulter®; and the PacBio RS® and the SMRT® system sold by Pacific Biosciences®. The ability of nanopores to insert into polymer membranes of this type would allow these systems to be adapted for folded protein sensing applications.

The polymer membrane may be formed of any suitable material. Typically, synthetic membranes are composed of amphiphilic synthetic block copolymers. Examples of hydrophilic block copolymers are poly(ethylene glycol) (PEG/PEO) or poly(2-methyloxazoline), while examples of hydrophobic blocks are polydimethylsiloxane (PDMS), poly (caprolactone) (PCL), poly(lactide) (PLA), or poly(methyl methacrylate) (PMMA). In embodiments, the polymer membrane used may be formed from the amphiphilic block copolymer poly 2-(methacryloyloxy)ethyl phosphorylcholine-b-disisopropylamino) ethyl methacrylate (PMPC-b-PDPA). DNA nanopores may be inserted into the walls of such polymersomes through incubation. Without wishing to be bound by theory, it is believed that the process of insertion likely involves a first step of membrane tethering, followed in a second step by vertical re-orientation of the DNA pore to achieve complete insertion. This however requires cholesterol anchors to be comprised within the pores, without which insertion does not take place. One exemplary embodiment is described in Example 2 below.

The ability to adapt the nanopores of the present invention such that they may be inserted into membranes of varying thickness is a significant advantage.

The molecular sensors and devices disclosed herein may be used for the detection or characterization of an analyte. Whilst the channel dimensions of the nanopores disclosed herein are particularly suitable for the detection of larger analytes such as unfolded or globular proteins, the nanopores are also suitable for the detection of other analytes. The nanopores may be modified to reduce the width of the channel making the nanopore suitable for the detection of analytes having a smaller width. However nanopores without the modified channel may also be used to detect analytes having a smaller width. Conversely modified nanopores may be used to determine analytes having a larger width than the width of the channel or constriction.

The analyte may be caused to fully or partially translocate the channel. The analyte may for example be held or lodged within the channel or channel entrance, for example at a constriction. Measurement of a signal, for example the change in ion flow during translocation may be used to detect or characterize the analyte. Alternatively the analyte may be caused to pass across the entrance of the nanopore channel in order to detect or characterize it.

Examples of analytes that may be detected or characterized are folded or unfolded proteins, DNA-protein constructs such as nucleosomes and polynucleotides such as deoxyribonucleic acid (DNA) or ribonucleic acid (RNA), polysaccharides and synthetic polymers. The target polynucleotide can comprise one strand of RNA hybridized to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The polynucleotide can be single or double stranded or have a tertiary or quaternary structure. The proteins or nucleic acids can be labelled with a detectable label. The label may be optically detectable such as a fluorophore. The analyte may be an enzyme and the sensor may be used to determine a conformational change in the enzyme.

The presence or absence of the analyte may be detected. Alternatively the analyte may be characterized, for example in the case of a nucleic acid, the sequence of the nucleotides may be determined from characteristic disruptions in the measured signal over time. In the case of proteins, aspects of the protein structure may be determined. The protein may be unfolded prior to detection using the nanopore. An example of such is disclosed in PCT/US2013/026414.

The invention is further illustrated by the following non-limiting examples.

EXAMPLES

Materials and Methods

Native and cholesterol-labeled DNA polynucleotides with a tri(ethylene glycol)(TEG) linker were purchased from Integrated DNA Technologies (Leuven, Belgium) or ATD-bio (Southampton, United Kingdom) on a 1 μmole scale with desalting or HPLC purification, respectively. 1,2-dioleoyl-sn-glycero-3-phosphoethanolamine (DOPE), 1,2-dioleoyl-sn-glycero-3-phosphocholine (DOPC) and 1,2-diphytanoyl-sn-glycero-3-phosphocholine (DPhPC) was procured from Avanti Polar Lipids (Alabaster, Ala.). M13mp18 DNA was from New England Biolabs (Ipswich, United Kingdom). $PEG^{350}$-FAM was procured form Chem Quest (United Kingdom). All other reagents and solvents were purchased from Sigma-Aldrich unless stated.

Nanopore Design

Figure 2:
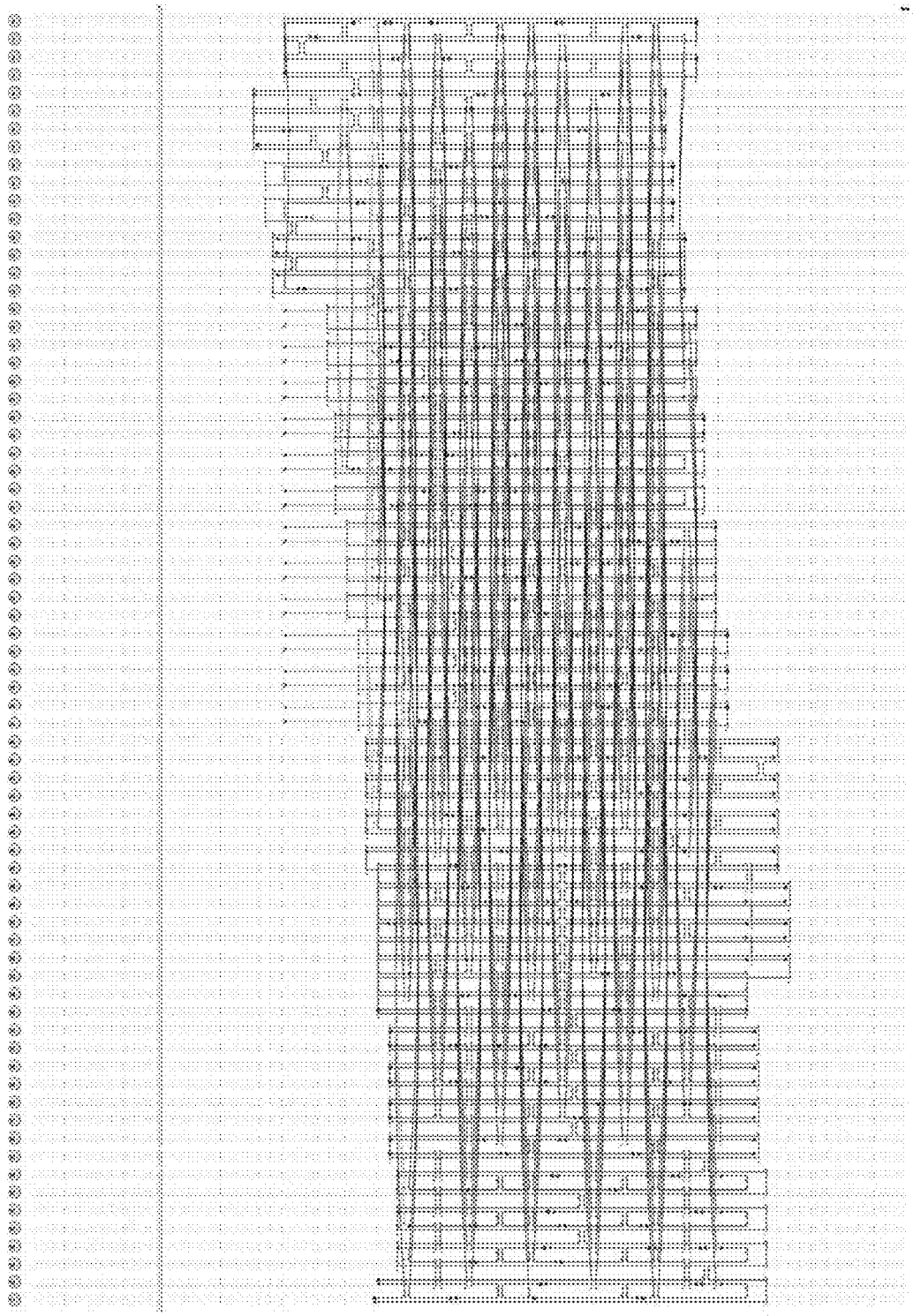
FIG. 2 shows a 2D DNA map of the nanopore $NP^{-C}$. The scaffold strand is shown in medium grey and staple strands are in dark grey. The horizontal strands terminating in a dot on the left hand side indicates adaptor strands which hybridize with a portion of their sequence to the cholesterol-modified anchor polynucleotides. 5' and 3' termini of DNA strands are represented as a squares and triangles, respectively. The duplexes are numbered at the left.

The DNA origami nanopores were designed using the square-lattice version of the CaDNAno software (Douglas S. M., Marblestone A. H., Teerapittayanon S., Vazquez A., Church G. M., Shih W. M. *Nucleic Acids Res.* 37, 5001-5006 (2009)). To assess rigidity in the structural design, several cycles of strand routing with CaDNAno and CanDo (Castro C. E., et al. *Nat. Methods* 8, 221-229 (2011)) modeling were conducted. The 7249 nt-long single stranded M13mp18 DNA was selected as the scaffold strand. The rendering of DNA nanopore and the 2D DNA map highlighting the scaffold in medium grey and staple strands in dark grey as shown in FIGS. 6 and 2, respectively. In the design, lipid anchors are attached to the pore via DNA polynucleotides that carry cholesterol at the 5' or 3' terminus. These cholesterol-modified anchor strands hybridize via adaptor polynucleotides to the pore; the adapter-mediated binding enables limitation of the number of expensive cholesterol-modified polynucleotides to two. The DNA sequences of staple strands, adaptor strands, and cholesterol-modified anchor strands are provided in Table 1.

Assembly

DNA nanopores were formed by first annealing $NP^{-C}$ in a one-pot reaction containing 1×TAE buffer, supplemented with 14 mM $MgCl_2$, and a mixture of M13mp18 scaffold and staples at final concentrations of 4.2 nM and 100 nM, respectively. Assembly was conducted using a 7 day-long protocol involving a first annealing phase from 80° C. to 60° C. at a cooling rate of 1° C. per 5 min, and a second phase from 60° C. to 20° C. at a rate of 1° C. per 300 min. To form nanopore NP with cholesterol lipid anchors, $NP^{-C}$ that underwent purification with size-exclusion chromatography (see below) was mixed with cholesterol-modified anchor polynucleotides (1.1 eq. strand per binding site at the pore, up to 24 sites) and incubated at 30° C. for 12 h.

Agarose Gel Electrophoresis of DNA Nanopores without and with Vesicles

The assembly products were analyzed using 1.5% agarose gel electrophoresis in standard 1×TAE buffer, optionally supplemented with 0.015% SDS. DNA pore samples (10 μL) were mixed with 6× gel loading buffer (2 μL) and then loaded into the wells. Gels were run at 70 V for 1 h at 8° C. A 1000-base-pair marker (New England Biolabs) was used as the reference standard. DNA bands were visualized by staining with ethidium bromide solution and ultraviolet illumination. SDS containing gels were washed with deionized water for 20 min prior to staining.

To analyze the interaction of NPs with membranes, small unilamellar vesicles (SUVs) were formed. Chloroform solutions of DOPE (0.3 mmol, 22.3 μL) and DOPC (0.7 mmol, 110 μL) were mixed, and added to an oven-dried round bottom flask (10 mL), followed by removal of the solvent under vacuum using a rotary evaporator for 20 min. To form vesicles, a solution of 0.3 M KCl, 15 mM Tris, pH 8.0 (1 mL) was added, and the suspension was sonicated for 20 min at RT. SUV preparations were stored at 4° C. and used within one week. Before experimentation, the SUV solution was vortexed for 2 s. For agarose gel electrophoretic analysis of nanopores with SUVs, the same gel conditions described above were used, except that SDS was omitted and gels were run at 40 V. Pores (15 µL, 1 µM, 0.3 M KCl, 15 mM Tris, pH 8.0) were incubated with SUVs (15 µL, 1 mM, 0.3 M KCl, 15 mM Tris, pH 8.0) for 30 min at 37° C. To the mixture, blue loading dye (6×, no SDS, 10 µL) was added and loaded onto the gel (30 µL).

Purification

The assembled nanopores were purified from excess staples via size exclusion chromatography (SEC) using an ÄKTA purifier 100/10 fitted with a Superdex 200 10/300 GL column (GE Healthcare), using a flow rate of 0.5 mL per min at 8° C. Elution was monitored via UV-vis absorption at 260, 280 and 295 nm, and fractions containing the folded DNA pore were pooled.

Atomic Force Microscopy

DNA origami pore $NP^{-C}$ was imaged using tapping mode in liquid, using Multimode VIII AFM equipped with a type E scanner (Veeco Instruments, Santa Barbara, USA) and silicon-tipped nitride cantilevers (Bruker, Camarillo, USA). Freshly cleaved mica was incubated with SEC-purified DNA pore solution (100 µL) for 15 min. Excess liquid was wicked off and replaced with 1×TAE buffer (100 µL) supplemented with 14 mM $MgCl_2$ and 4 mM $NiCl_2$.

Nanopore Current Recordings

For planar lipid bilayer electrophysiological current measurements, an integrated chip-based, parallel bilayer recording setup (Orbit 16, Nanion Technologies, Munich, Germany) with multielectrode-cavity-array (MECA) chips (IONERA, Freiburg, Germany) was used (Burns J. R., Seifert A., Fertig N., Howorka S. A. *Nat. Nanotechnol.* 11, 152-156 (2016); Del Rio Martinez J. M., Zaitseva E., Petersen S., Baaken G., Behrends J. C. *Small* 11, 119-125 (2015)). Bilayers were formed by spreading via a magnetic stirring bar DPhPC dissolved in octane (10 mg $mL^{-1}$). The electrolyte solution was 1 M KCl and 10 mM HEPES, pH 8.0. For pore insertion, a 2:1 mixture of cholesterol-anchored DNA nanopores and 0.5% OPOE (n-octyloligooxyethylene, in 1 M KCl, 10 mM HEPES, pH 8.0) was added to the cis side of the bilayer. A positive voltage of +30 mV was applied to facilitate pore insertion. Successful incorporation was observed by detecting the current steps. The current traces were Bessel-filtered at 2.873 kHz and acquired at 10 kHz with an EPC-10 patch-clamp amplifier (HEKA Elektronik, Lambrecht/Pfalz, Germany) with the PATCHMASTER software (HEKA Elektronik). Single-channel analysis was performed using Clampfit (Molecular Devices, Sunnyvale, Calif., USA).

Release Assays with Fluorophore-Filled Vesicles

Giant unilamellar vesicles (GUVs) were formed by adding a solution of DOPE (0.3 mmol, 50 µL) and DOPC (0.7 mmol, 550 µL) to an oven-dried round bottom flask (10 mL), removing the solvent via vacuum using a rotary evaporator for 20 min, and drying the thin film under ultra-high vacuum for 3 h. A solution of sorbitol (1 M, 1 mL) containing $PEG^{350}$-FAM (10 µM) was added to the flask, and the solution was sonicated for 30 s to form fluorophore-filled vesicles. After 20 min incubation, a portion of the GUV suspension (1 µL) was added to PBS (200 µL) within an 8-well glass chamber (LabTek). After settling the vesicles for 5 min, a mixture of NP/OPOE (12.5 µl 0.5% OPOE, 37.5 µl PBS, 100 µL SEC-purified NP, incubation at 35° C. for 30 min) or OPOE/anchor-cholesterol strand (12.5 µL 0.5% OPOE, 37.5 µL PBS, 100 µL SEC-purified anchor-cholesterol strand, incubation at 35° C. for 30 min) was added. The fluorescence images of GUVs were collected using excitation at 515 nm and the appropriate emission filters.

Figure 1B:
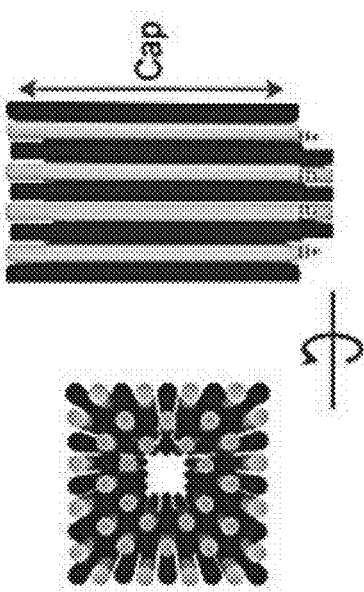
Figure 1C:
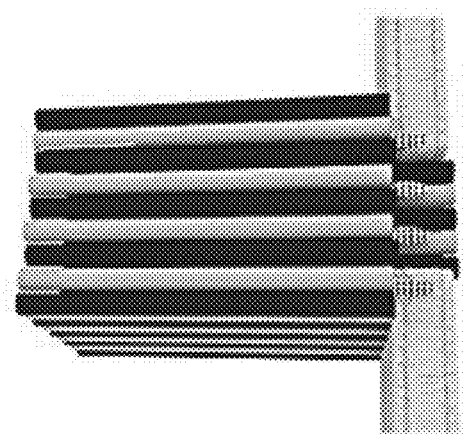

Example 1: Assembly and Characterization of Wide Channel DNA Nanopores According to the Present Invention An embodiment of a membrane-spanning DNA nanopore 10 according to the present invention is shown in FIG. 1. In this embodiment, DNA duplexes are squarely arranged and interlinked to create a wide channel lumen having interior dimensions of approximately 7.5 nm×7.5 nm. As outlined in the "Nanopore current recordings" section above, the wide pore successfully inserts into lipid bilayers and shows considerably less closures at high voltages than prior art smaller diameter DNA nanopores (see, for example, Douglas S. M., Marblestone A. H., Teerapittayanon S., Vazquez A., Church G. M., Shih W. M. *Nucleic Acids Res.* 37, 5001-5006 (2009); Zheng J., et al. *Nature* 461, 74-77 (2009); Rothemund P. W. *Nature* 440, 297-302 (2006); Fu J., et al. *Nat. Nanotechnol.* 9, 531-536 (2014); Burns J. R., et al. *Angew. Chem. Int. Ed.* 52, 12069-12072 (2013); and Seifert A., Göpfrich K., Burns J. R., Fertig N., Keyser U. F., Howorka S. *ACS Nano* 9, 1117-1126 (2015)).

The nanopore 10 was designed with the CaDNAno software (Burns J. R., et al. *Angew. Chem. Int. Ed.* 52, 12069-12072 (2013)) and when assembled comprises squarely arranged DNA duplexes 12, 14. The DNA duplexes 12, 14 are interlinked by cross-overs 16. In this embodiment, the pore 10 has a total height of 46 nm and features and has a square design in cross-sectional profile parallel with the membrane surface. The external side length of the pore 10 is 22.5 nm.

In this embodiment, the cap region 18 is 35 nm in height and comprises a generally-square channel or lumen 19 surrounded by an upstanding pore wall 22. The pore wall 22 is composed of multiple duplex layers to increase structural stability (FIG. 1). In this embodiment the pore wall 22 is composed of three duplex layers, although depending on the requirements of the pore the pore wall 22 may be one; two; three; four; or five or more duplex layers thick.

In the membrane-spanning region 20, the pore wall 22 may comprise fewer duplex layers than that in the cap region 18 to decrease the overall pore size and hence lower the energetic costs of membrane insertion. In the embodiment shown in FIG. 1, the pore wall in the membrane-spanning region is two duplex layers thick.

The membrane-spanning region 20 carries lipid anchors 24. The lipid anchors 24 are composed of cholesterol.

As shown in a cross-section (FIG. 1C), the pore lumen 19 is 7.5 nm×7.5 nm and features at its top a wider opening to help facilitate entrance of molecules. When inserted into a membrane (FIG. 1A), the pore 10 is expected to enable transport of protein cargo 26 from the cis to the trans side of the membrane.

The pores were successfully assembled via the DNA origami 'scaffold-and-staple' approach (Rothemund, P. W., Nature 440, 297-302 (2006). In this important route to DNA nanostructures, staple polynucleotides direct the folding path of a long single stranded DNA scaffold. The 2D-DNA map and DNA sequences of exemplary component strands are shown in FIG. 2 and provided in Table 1, respectively.

The sequence of the DNA scaffold is from M13mp18 DNA (SEQ ID NO. 1)

TABLE 1

Sequences of DNA staple, adaptor, and cholesterol-modified anchor polynucleotides. All DNA sequences are from the 5' to the 3' terminus. The names of staple and adaptor polynucleotides indicate their position within the 2D DNA map of the pore (FIG. 2) described as helix and base pair coordinate where the strands' 3' terminus is positioned within the numbered DNA helix of the nanostructure. The name of two cholesterol-modified anchor strands indicates whether the cholesterol-TEG modification is attached to the 5' or 3' terminus. Adaptor strands have two sequence parts which hybridize either to the DNA staple strands or the cholesterol-modified anchor polynucleotides (highlighted in bold). Adaptors that carry the latter sequence part at the 5'-end hybridize to 3'-cholesterol anchor polynucleotides. Conversely, adaptors with the sequence part at the 3'-terminus hybridize to 5'-cholesterol anchor polynucleotides. Adapter strand 21[64] features both a 5'- and a 3'-terminal hybridization segment.

| SEQ ID No. | Name: Helix [base position] | Sequence |
|---|---|---|
| | | Staple strands |
| 2 | 47[136] | GGAACAAATCATATATCCCACAAGCTTACCGAAGCTTGATTTCGGTCG |
| 3 | 71[156] | AAATGTTACAAAATCGCGCAAAA |
| 4 | 35[125] | TAACACCACCAGAGCCACC |
| 5 | 44[190] | GAAGGGTTAGAACCTTATACTTCTGAATAA |
| 6 | 45[115] | CATTAAGTAAGCATGAGCGCTCCCTGAACTCTGG |
| 7 | 0[102] | CCAAGCGTTGAGCCAAGGTGAATGTCA |
| 8 | 33[109] | GTGCATTAATTAGCTCGAATTCGTAATC |
| 9 | 52[111] | AAAATTCGAACCAATACTCCCGACAAAGCACTC |
| 10 | 62[135] | ACGGCCAGTAGCTGTTTCCTGTGTGAATTGTTAT |
| 11 | 65[149] | CTCAAGTGTAAGAATCATAACCGAGTAAAAGAACG |
| 12 | 22[90] | TAAGAAGAAAATCTACAAAGCCGGAGACAGTCAAATCAC |
| 13 | 4[94] | GGCTCCATTAATTGTCGAAC |
| 14 | 34[164] | TATTTCAGAGCGGATGGTTGCTTTGACGAACGCT |
| 15 | 32[122] | GGCTGAATTTAGCCTTGAGT |
| 16 | 44[106] | AAAGTTACCAGATAAAAGAGGACTAAAGCGATTATA |
| 17 | 48[156] | TGAGTCAGAAGGAGCGGAATTATCATCATATATAATCAGC |
| 18 | 57[131] | CGCACTTCCAAGAAGATAAGTGTATAGCCGGATTAGGA |
| 19 | 31[125] | AACAACATGTTCAAGAGAACGGAATAGG |
| 20 | 25[133] | GATAATTTGCCTTGCTAAAGCGAATAAT |
| 21 | 0[82] | AACTAGCAACGGCTACAGAGTC |
| 22 | 10[118] | AACAGTGAGACTCCTCAGCTAATGCAGATAAGGCT |
| 23 | 56[166] | AGAACCCCCAGTCACACCAATCAATCCT |
| 24 | 70[130] | AGAACGTGGACATCAAGTTTTCAATTATTGCTCCTGCT |
| 25 | 13[128] | ACCGGAACCAGTAGCGTAATT |
| 26 | 31[112] | ATTTAACAAGCTGGCGAACTGTTGGGAAGGGCCGG |
| 27 | 20[94] | AGAACTGATAAAGCTAAAGGGTGAGA |
| 28 | 2[170] | AACCATCGCCCCACTACGACTTATTACACCAGCGC |
| 29 | 43[141] | TTTATTTCGCAATCAATAGGAGGGAGGGCACC |
| 30 | 27[113] | ATCGAGAAGATGGGCGGAACAAACGGCGGATTGAC |
| 31 | 10[83] | TATTTCGGATAATCTTGACAATTATAT |
| 32 | 62[114] | TGCGGGTTTTCCCAGTCACATTACGCCACGCC |
| 33 | 12[167] | CCACCCTCAAGACAAAGAGTC |
| 34 | 24[122] | CAAATAAGAAAATCGTAAAAAACAAGAGAATC |
| 35 | 25[157] | CTAAAGCATCACAATATCTGGTCAGTTGCACTAACGCAGCCTTTACAG |
| 36 | 19[141] | GAACGTAGAAATTAAACGGGAATACACT |
| 37 | 52[193] | CCACGCTGAGAAAGGAATTG |
| 38 | 28[175] | ATGTAGAAACGACCAGAATACCTACATTTTGATTA |
| 39 | 1[120] | CATGAGGATGCAGGGACGAGG |
| 40 | 66[132] | AACGCGCGGGGAGGCAACAGCCTACCTTTGTCGC |
| 41 | 26[114] | AACGGAACGCCGCCAGCTTT |
| 42 | 56[185] | CATTCTGGCCTCTTTAAT |
| 43 | 20[111] | GATAGCCGATCAGCTTCCGCTT |
| 44 | 35[157] | CGCAGAGCCACGCCACCCTCAGAACCGACCAA |
| 45 | 13[141] | CCCTCATAGGTAAATGCTGAACAATCGGCC |
| 46 | 52[143] | AACCTCAACCACCAGCGTATTCTATATTTTCACCT |
| 47 | 32[90] | TGCCTCATTAAATGCCCCCTGCC |
| 48 | 19[125] | AAATTAAGAAATGACCCTGTAATA |
| 49 | 41[115] | GTAGCGGAAATTAACGGAATAGACCCCCAGACTTTTT |
| 50 | 64[164] | AGCCGGAAGCATAGTTAGAATTAGTTAATCCAAT |
| 51 | 57[108] | GACAGCCGGAAACCAGGCAAAGCGC |
| 52 | 39[125] | GCAATATTGACTCAACATGTTTTAAATATGCA |
| 53 | 53[164] | GGCGGTCAGTATTAACACCGGCGCGAA |
| 54 | 31[88] | GAATCGTCGACTGGATAAACATGATAGTAC |
| 55 | 4[146] | CTAGTCAAAAACGTCTTTCCCCTCAATCCTTGCTG |
| 56 | 7[57] | ATGAACGGTGTACAGACTTTGA |
| 57 | 37[133] | AATTCAATATAAAATCGG |
| 58 | 1[155] | AATGCACGCATAAAGAACTGGAAATAGCATATTTCAAAAA |
| 59 | 22[122] | ACAAATATCAGTAATGCCGATTCAACCGTTCTAGC |
| 60 | 30[138] | CGACGGCTGGTAATATCCAGAACAATACGCTCAATAAT |
| 61 | 54[110] | CATCAACTCTCCGTGGCATCGTAACCGTGCATCTGC |
| 62 | 14[162] | TGATAGCGATAAATTACCTTAGCCCGAAGTGTTGTTCCAGTTTCACT |
| 63 | 46[120] | TGAGTAATGAATATGATGAGAGGGTA |

TABLE 1-continued

Sequences of DNA staple, adaptor, and cholesterol-modified anchor polynucleotides. All DNA sequences are from the 5' to the 3' terminus. The names of staple and adaptor polynucleotides indicate their position within the 2D DNA map of the pore (FIG. 2) described as helix and base pair coordinate where the strands' 3' terminus is positioned within the numbered DNA helix of the nanostructure. The name of two cholesterol-modified anchor strands indicates whether the cholesterol-TEG modification is attached to the 5' or 3' terminus. Adaptor strands have two sequence parts which hybridize either to the DNA staple strands or the cholesterol-modified anchor polynucleotides (highlighted in bold). Adaptors that carry the latter sequence part at the 5'-end hybridize to 3'-cholesterol anchor polynucleotides. Conversely, adaptors with the sequence part at the 3'-terminus hybridize to 5'-cholesterol anchor polynucleotides. Adapter strand 21[64] features both a 5'- and a 3'-terminal hybridization segment.

| SEQ ID No. | Name: Helix [base position] | Sequence |
| --- | --- | --- |
| 64 | 2[135] | CTGAGGCTAGTTTCCAATACATACTTGTCACAAAT |
| 65 | 9[104] | AGAGGCTGCCCGTATATCAGCCAT |
| 66 | 45[133] | CTTTTGCGGGAAATAAAGATAACG |
| 67 | 8[89] | CGCCACCCTCAGAACAGGCGCATAGGTTCATCAAGAGACCTATTATT |
| 68 | 53[96] | CATTTTTTCATTAAATAAAGGAATGAGAT |
| 69 | 4[114] | TTGCAATCCAAAATAAACAGAAGATTGATTTTGTT |
| 70 | 54[167] | CTAAAACACGCGCCCAAATCAGAT |
| 71 | 42[190] | GAGACCCAATTCTGCAGTACCTTTTACATC |
| 72 | 61[91] | CGATTAAGTTGGGAATCCCCCTGACCATAAATCA |
| 73 | 47[108] | CATCTGTAGGTAAGGGTAAT |
| 74 | 0[170] | CACCAACCTAAGAAACGTC |
| 75 | 32[170] | ATGAGCAATACAGTGTTTTATAATCACACAATTCACG |
| 76 | 50[132] | CGGTACGATTTTTGAGAATTATCTTAAACAGCCC |
| 77 | 12[110] | CCAGCATTGGAAAGCCGTAAAATCAGGTCTTGCCCGCTTGGGCGCCAGGG |
| 78 | 38[178] | AATTTCATTTGGCTTAGATGAAA |
| 79 | 37[109] | TTCCGGTCCACTTCACCAGT |
| 80 | 10[164] | CAGGAGTGTACTGGTAATAAGGGTTTTGCTCTGT |
| 81 | 8[107] | ACTCTAGACGCGCCTGTTTACTTCTGGTGTATCGG |
| 82 | 15[141] | ATTTACATAAATTTCCCTTCAACCGCCTGGC |
| 83 | 68[171] | GCGACCACACCCGCCGCGCTCTACAGGG |
| 84 | 24[106] | ATTTTGCGGGACTCATAGTCCACCACCCCGT |
| 85 | 37[89] | AAATATCTAGCGCGTTCACCGACCGAAA |
| 86 | 29[155] | ATCCCATAATCGGCCGTAACAATAGAAGGCCCAG |
| 87 | 16[170] | AGACAAAAGGGAAAATTAAAATAC |
| 88 | 64[133] | GCCTAATGAGTGAGGTCGTGCCGGTTTGAATTATA |
| 89 | 24[98] | TTAGACGTTAGCAAAAAAAA |
| 90 | 60[167] | GAGTAGAAACCGTTGTCGTTATACAAAAAGCCATA |
| 91 | 13[109] | CACCGGCAAAAAGATTAAG |
| 92 | 17[125] | ATTATAAAGGTACATCCAATAAATTGCGTAGA |
| 93 | 15[69] | TGCTCATTCAGTGAATAAGTTTCATCGGCATTTTCGGTCACAACG |
| 94 | 48[193] | TAAATCCTTTTTATCAGA |
| 95 | 6[129] | AGCATTCCACATGGGATTAGTTA |
| 96 | 18[148] | GCAAATACCCAAACCGATATAACCGATAGAACAA |
| 97 | 67[113] | GAGACGGAGGCGGTTAGGTTGGGATACCGACGCAG |
| 98 | 48[110] | GCTATTTCCTGAGAGAAAGTCAGATTTA |
| 99 | 49[139] | TAATATTAGACGGTGTTTAACAAGGAATTCAACTTTC |
| 100 | 12[82] | CAGACGATTGGCCTTGCATTA |
| 101 | 0[134] | AAAACACCACCAGTAGAAGGTAAAAAGAAGATTATTCAT |
| 102 | 6[94] | GATCTAATCTTTCCAGGAATACCGAAAGATTCCGG |
| 103 | 59[91] | CATTCGCCATTCAAATGTTTAATAAATATAACAGTTAAGCCAGAATGAC |
| 104 | 50[183] | TAAAATATCTTTAGGAGGCAAATCAACAGTTG |
| 105 | 71[87] | GGGCGATGGTTTTGCGGATG |
| 106 | 4[162] | GAATAGAAAGGTTGCGCCGAAAACAGGTAAGCCCAGTT |
| 107 | 18[90] | TGGTGGCATCATAAAGCCTCAG |
| 108 | 40[190] | AACGGATTCGCCTGAAACAGTTGATTAACA |
| 109 | 37[149] | CCTTATCAAAATCAGAGCCCACCCTCAG |
| 110 | 69[135] | CAAAATCCCTTATAAATGGCGCTGGAGAAT |
| 111 | 52[183] | AGCCAGCAGCAAATGAAAAATCTACAATTTTATACCAACG |
| 112 | 43[157] | CAGTTGCACGTAAAACAGAGAAGCCTTATAGC |
| 113 | 50[143] | CCGTCAATATATCAAACAGAGCCTTAGTTGCTACT |
| 114 | 29[165] | AATTTACGAGCAGTACCGAAGCCATTGACTTGCCT |
| 115 | 31[157] | CAGAAAGTAATTCAGTACCAGGCG |
| 116 | 59[108] | GCGCAAAGGGGGATGTGCTGCAAGG |
| 117 | 13[62] | CAAATTAGCCCCCTTATTAGCGTTTGCAGGT |
| 118 | 55[150] | AGACAATATTTTGAATG |
| 119 | 39[100] | GGATGAGGTCATCCCACTACGTGA |
| 120 | 20[130] | TTTCGCAATAAAATCATACAGGCAAGGCAAAGAATAAA |
| 121 | 50[91] | TTGAGGCTATCAGGTCATTGTTGAGAGAATCTA |
| 122 | 29[88] | TTGCCAGACGAGAGGCACCGCCACATAGTAAGTAA |
| 123 | 68[158] | GCGCTAGCAAAAGAATTTTTAATAAGAAAACCGAC |
| 124 | 26[100] | GAGGCCCTCAGAGTAGCGTAAC |
| 125 | 41[147] | GTACGAACCGATTAAAATTCAAGGCAAAGTAAAATACGT |
| 126 | 46[156] | ATTTTTTAGAACCCGAAACCACAACATTATCATTTTGCAGA |
| 127 | 23[157] | ATAAACTAATAGATTTAGAAGTATTAGTTTTAAAAATAATAAG |

TABLE 1-continued

Sequences of DNA staple, adaptor, and cholesterol-modified anchor polynucleotides. All DNA sequences are from the 5' to the 3' terminus. The names of staple and adaptor polynucleotides indicate their position within the 2D DNA map of the pore (FIG. 2) described as helix and base pair coordinate where the strands' 3' terminus is positioned within the numbered DNA helix of the nanostructure. The name of two cholesterol-modified anchor strands indicates whether the cholesterol-TEG modification is attached to the 5' or 3' terminus. Adaptor strands have two sequence parts which hybridize either to the DNA staple strands or the cholesterol-modified anchor polynucleotides (highlighted in bold). Adaptors that carry the latter sequence part at the 5'-end hybridize to 3'-cholesterol anchor polynucleotides. Conversely, adaptors with the sequence part at the 3'-terminus hybridize to 5'-cholesterol anchor polynucleotides. Adapter strand 21[64]features both a 5'- and a 3'-terminal hybridization segment.

| SEQ ID No. | Name: Helix [base position] | Sequence |
| --- | --- | --- |
| 128 | 30[146] | CCAAGAAAAATCGTCTGAAATGGAAGCCAGCTTTCGAT |
| 129 | 33[131] | AGAATAATTTAATAGCTGCATTAATGGTGCTTTC |
| 130 | 19[93] | CTTATGCGAAATTAAGCAAATTCTACTA |
| 131 | 48[175] | GTTATTAAACTTTACAAACAATTC |
| 132 | 34[138] | CTAAAACACCGAGCCTGGGGT |
| 133 | 36[178] | GACGCTGAGAAGAACGCGACGCGT |
| 134 | 29[101] | TAAAGGAGGTTAAGTATTA |
| 135 | 49[133] | GATTGATAAATAGAGATAATTTAAATGCAATGCC |
| 136 | 70[170] | TTGGATAGCCGGCGAACGTGAAGGGAA |
| 137 | 42[132] | GGTCAATAACCTGTTTAGCTATAGCATTAGGCAA |
| 138 | 67[157] | GCGAGTGAATTTGAAAACAAACCATCGCAAGG |
| 139 | 11[116] | TCTCTTAATTGAGAATCTTGTAACGCCACTGCAGGTCGACTCTAGAGGA |
| 140 | 23[109] | TCCAAAATCTCTAAATGAA |
| 141 | 12[99] | AGGAAAGCGGATTGCATCTTTGCGTATTTCCAGTC |
| 142 | 3[64] | TTGTGTCGAAATCCGCAAAGACAGCATATAAAGCCTGCGG |
| 143 | 36[162] | AATCGTAACCAAAGGAGCGG |
| 144 | 58[124] | CACCGTCAACAATACGGGTATCAGGGATAAGGCG |
| 145 | 63[121] | ATGGTCATGCCAAGCGGCGTTAAAGTAG |
| 146 | 2[92] | ACCCTCAGCAGCGGACAGCCTAAAGG |
| 147 | 71[108] | ACCATCACCCAATCCAACGTACCTTTAAAATAA |
| 148 | 67[96] | TTTTTCTTGCTGGTTTGCC |
| 149 | 43[105] | ATAGTAGTATTTTCAAAGACACCTTCATTAATTTG |
| 150 | 8[164] | GATAAGTGCCGTCGAGAGGGTCCCATGTACTGTC |
| 151 | 57[91] | CAGTTTGAGGGGACAAAATAGGGGGG |
| 152 | 16[155] | ATTCGTGTCTGGTTTGACCATTAGATACTCAGGTTTTTA |
| 153 | 44[167] | AAAATTATATGAATATACAGTAACGAACGAGTCAA |
| 154 | 46[190] | GATGGCAATTCATCAATTCCTGAGCCCGAAC |
| 155 | 1[72] | AACGAGGGGAGATTTGTATCATCAAAGC |
| 156 | 18[114] | CATAAGGAAACGTTAAAGGGCTTTCGATCACG |
| 157 | 42[167] | AGATTTAGAAGTTTCATTCC |
| 158 | 11[133] | CCAACCAGAACCTATATGTCTGAGAGATGATTGCC |
| 159 | 40[162] | CAACGGAACCCTAAAGGGAGCCCCCGAGACGGGGA |
| 160 | 54[122] | GTAATCAAAAATAATTCGCAATTGTAAATCAA |
| 161 | 0[90] | CAACGAGTAGTAAATTGCATTTGGGGCAATTGCTG |
| 162 | 8[118] | TGTATCACTCATTTTTAAACCAAGTACCAACCGAC |
| 163 | 50[193] | GAAGGTTATCGACAACTCGT |
| 164 | 6[140] | ACAACAATAGGAATGATATAACCTGAACAGACGA |
| 165 | 68[131] | CCTGAGAGAGTTTGGTTCCGTGTGAGTGCCTGA |
| 166 | 15[108] | GGAATGCAGCTTCAAAGCGAGCAGGCGAGAAAAACCGTCTATCA |
| 167 | 4[126] | AATTTTTGGTGAATTACTGA |
| 168 | 5[112] | TTTTCTGTAGACAGCCGGTTTTGATAGCG |
| 169 | 15[157] | CCGAACGAAAGTATGGTTTGCAGTATGAACGT |
| 170 | 55[132] | CGTAGTCTGGCCGCCGTTTTAGAACGCGGCAAGCCCGCCTGT |
| 171 | 63[155] | CCGCTGTGAGGCCATTACTAGAAATTCTTGCTTTTGATGATA |
| 172 | 41[172] | ATATTTGCTTTGTTACATTTAAGGG |
| 173 | 21[101] | CGTAAGATTCAAAATCGGTTGTACCAATAGCA |
| 174 | 71[128] | TTTTGGGGTCGAGGTGCCGTAAAGGGAACAAGCAAACATCGGAAA |
| 175 | 5[144] | AACAGTTTCAGTACAAATTTTGCACTTATCCGAGA |
| 176 | 57[119] | CCTCAGGAAGTTGGTGTACAAGCAATTCCT |
| 177 | 59[163] | CCGCCCAAAAGGTTAATAAGAGAATATAAATCAT |
| 178 | 20[146] | TATAATTGAGTGAAGCGCACATTTGAGGATTAGAG |
| 179 | 46[167] | CTGGGATACGCAAATTGTTTGGATACCATATCAGA |
| 180 | 60[185] | TAATAACATCCAACAGGAAA |
| 181 | 56[154] | ACCATCATTACTCGCCATTAAACAGAGGTGA |
| 182 | 22[172] | AGAGAATAACATAACAATGACAAACAATGCATGATTA |
| 183 | 61[140] | TCTGTCCATCACGCAAATTAGAACTCAACGAGC |
| 184 | 37[125] | TATACAGAATCAGCAAAATTCATCTTTAGTTT |
| 185 | 41[104] | AATATAATTTTGATAATAGAGAGTCAAAGGGCAAATCCTGT |
| 186 | 62[185] | AATCCTGAGATTCTTTGATT |
| 187 | 34[148] | ATCTTCATACATGACCAGTATGGCATTTTACTATC |
| 188 | 67[136] | CTTCAGTGTAGCGGTCGCACGTATATGCAAATTTC |
| 189 | 34[178] | AACTTTTTCAATGTTTAGTACAAACATCACACGGAACGGTACGCC |
| 190 | 60[145] | GGCCTTGGCCTCTTCGCTGACGTTGTCGCTCAACATA |
| 191 | 66[170] | ACTGAGCTAAACAGGAGGCGATTTTAG |

TABLE 1-continued

Sequences of DNA staple, adaptor, and cholesterol-modified anchor polynucleotides. All DNA sequences are from the 5' to the 3' terminus. The names of staple and adaptor polynucleotides indicate their position within the 2D DNA map of the pore (FIG. 2) described as helix and base pair coordinate where the strands' 3' terminus is positioned within the numbered DNA helix of the nanostructure. The name of two cholesterol-modified anchor strands indicates whether the cholesterol-TEG modification is attached to the 5' or 3' terminus. Adaptor strands have two sequence parts which hybridize either to the DNA staple strands or the cholesterol-modified anchor polynucleotides (highlighted in bold). Adaptors that carry the latter sequence part at the 5'-end hybridize to 3'-cholesterol anchor polynucleotides. Conversely, adaptors with the sequence part at the 3'-terminus hybridize to 5'-cholesterol anchor polynucleotides. Adapter strand 21[64] features both a 5'- and a 3'-terminal hybridization segment.

| SEQ ID No. | Name: Helix [base position] | Sequence |
| --- | --- | --- |
| 192 | 53[147] | AGATAAAAAATACCGAACGAAATGATACGTGGCAC |
| 193 | 63[91] | TCCCCGGGTACCGGCGTTGCGCTC |
| 194 | 38[114] | CCTTTAGAGCCAAGTTTGCCTTTAGCGAAAAT |
| 195 | 28[146] | TTTTCGTAGGATGAAAGCGTAAGAGGATAGGTCACGAT |
| 196 | 27[93] | CAGTGAGCGAGAATCAGCT |
| 197 | 28[140] | TATCATCCTTATTTACATTGGCAGATTCATTCTG |
| 198 | 54[176] | CTGATAGCCGCTATTAGAACAGAGAT |
| 199 | 65[111] | GGGAAACCTCTAACTCAATAAATAATTGCA |
| 200 | 50[98] | ACCCATCAGTTTAATAAAAATCGGTTTAACATTTTA |
| 201 | 6[162] | AGTTTCGTCACCAGCGGAGCTAACGAGTGAAA |
| 202 | 13[96] | TCATAATCTCAGACTGGCGTTTTAATTCG |
| 203 | 26[122] | TTTAGCCTTAAACGTTAATTATAAGCAAATATTTAGAA |
| 204 | 41[141] | ACTGAGGCGAATGATGAAAAGTCCACTATTAA |
| 205 | 6[64] | AAGAGGACAGGCGCAGACGGTCAATTACTTAGCCGGAACGA |
| 206 | 12[142] | AGCCGCCGTAAGCGTCTGAC |
| 207 | 55[88] | TAACAACCCGTCGGATATTAAATGACGACGATTAC |
| 208 | 5[80] | AACTGTCGAGTTTCGACAG |
| 209 | 49[117] | AGCACTAGCATGTCAATCAAAAAACAGGCCAT |
| 210 | 58[185] | CGCTCATGGATAATAAAAGG |
| 211 | 59[131] | CGGTGCAATAAACATGTAATTGGGTCAGTCCGTT |
| 212 | 16[90] | CCGTAGAGCTTGCGAGCTGAAA |
| 213 | 9[137] | TTAGCGGTTTTAACGTAGGCAGAAAAGCCAAAAAG |
| 214 | 69[113] | TTGATGGGCAGCAAGTGTAAATCTTAAC |
| 215 | 38[146] | CAGACCATTAGATAGCAGCACCGTAATCGCCT |
| 216 | 25[91] | CGCCATTTTGTTATAATCAGAAAAGCCCCTATGT |
| 217 | 2[105] | TTGCGGGATCGGCTTTGAAACGGGCTTGAGA |
| 218 | 36[114] | CTCCGGAACCAGAGCCGCCG |

| | Adaptor strands | |
| --- | --- | --- |
| 219 | 33[64] | CTCCGTCTATCTTTTTGTTCAGAAAACGAGAATCAAA |
| 220 | 39[64] | CTCCGTCTATCTTTTTTTTCAAACTCCAACAGTATCA |
| 221 | 25[64] | CTCCGTCTATCTTATGACTGACCAACCCGCCA |
| 222 | 27[64] | CTCCGTCTATCTTCATAACCCTCGTTTAC |
| 223 | 31[64] | CTCCGTCTATCTTTTTATACTGCG |
| 224 | 17[64] | CTCCGTCTATCAGAAACACCAGAAAGTAC |
| 225 | 19[64] | CTCCGTCTATCTTAATCATTGTGAATTAC |
| 226 | 29[64] | CTCCGTCTATCTTTTTAAGAAGTT |
| 227 | 37[64] | CTCCGTCTATCTTTTTTTTGACTTC |
| 228 | 35[64] | CTCCGTCTATCTTTTTTTATAGTCAGAAGCAGGTTGAGGCCATCTTT |
| 229 | 23[64] | CTCCGTCTATCTTTATCTCCATGTCATAAGGG |
| 230 | 21[64] | CTCCGTCTATCGTCAGGACGTTGGCGGAACAACATTTGCTACGTCAGC |
| 231 | 65[93] | ACTTACCCTGACTATTTTTTTTTGCTACGTCAGC |
| 232 | 4[82] | CTGTACAGGTAACATTCAACTATTGCTACGTCAGC |
| 233 | 43[85] | AGGTTTAATTTCAACTGCTACGTCAGC |
| 234 | 45[85] | AGCGCTCATTATACCAGCTACGTCAGC |
| 235 | 41[85] | GCTGCTTGCCCTGACGGCTACGTCAGC |
| 236 | 9[85] | CTGAGCGTCCATTTTTGCTACGTCAGC |
| 237 | 7[80] | CCCTCAGATTTTGCAATTTTTGCTACGTCAGC |
| 238 | 11[71] | TCACAAACAAATAAATCTTTAAACATTTTTGCTACGTCAGC |
| 239 | 25[83] | ATACAAGCAACACTATTTGCTACGTCAGC |
| 240 | 67[93] | TGGAGGAAGCCCGAAATTTTTTTGCTACGTCAGC |
| 241 | 69[93] | CCAACCAGACCGGAAGTTTTTTTTGCTACGTCAGC |

| | Anchor strands | |
| --- | --- | --- |
| 242 | Cholesterol 3' | GATAGACGGAG-TEG-Chol |
| 243 | Cholesterol 5' | Chol-TEG-GCTGACGTAGC |

Lipid anchor-free variants of the nanopore ($NP^{-C}$) may be assembled first and then converted into a lipid-modified pore (NP) by hybridizing to sticky ends within the transmembrane region polynucleotides carrying the cholesterol anchors. Assembly of $NP^{-C}$ followed an optimized annealing protocol (see "Assembly" section below). The fabrication outcome was analyzed by gel electrophoresis to yield a single defined band as shown for cholesterol-free $NP^{-C}$ (FIG. 3A, panel −SDS), implying a homogenous population of folded products. The pore band migrated at a different height than the scaffold strand (ss) (FIG. 3A) suggesting complete assembly. Pore NP with cholesterol anchors also led to a defined band when analyzed in detergent SDS (FIG. 3A, panel +SDS) to suppress the known streaking likely caused by hydrophobic interactions with the gel matrix (FIG. 3A, panel −SDS) (Langecker M., et al. *Science* 338, 932-936 (2012); Burns J. R., Al-Juffali N., Janes S. M., Howorka S. *Angew. Chem. Int. Ed.* 53, 12466-12470 (2014)).

Figure 4:
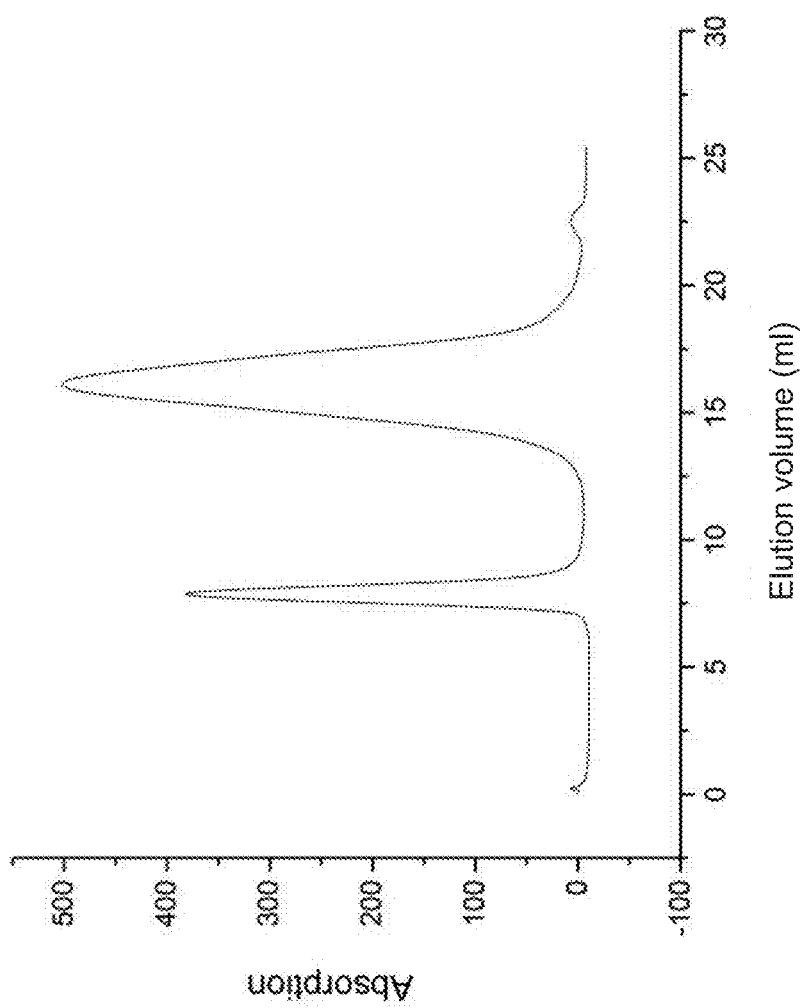
FIG. 4 shows a size exclusion chromatography trace of an assembly mixture containing the folded DNA nanopore (elution volume of 7.88 mL) and excess staple strands (elution volume of 16.13 mL). Absorption was determined at 260 nm.

DNA pores with a molar mass of 4.87 MD were purified via size exclusion chromatography (SEC) (FIG. 4) from excess staple polynucleotides and used for the biophysical characterization.

Figure 5:
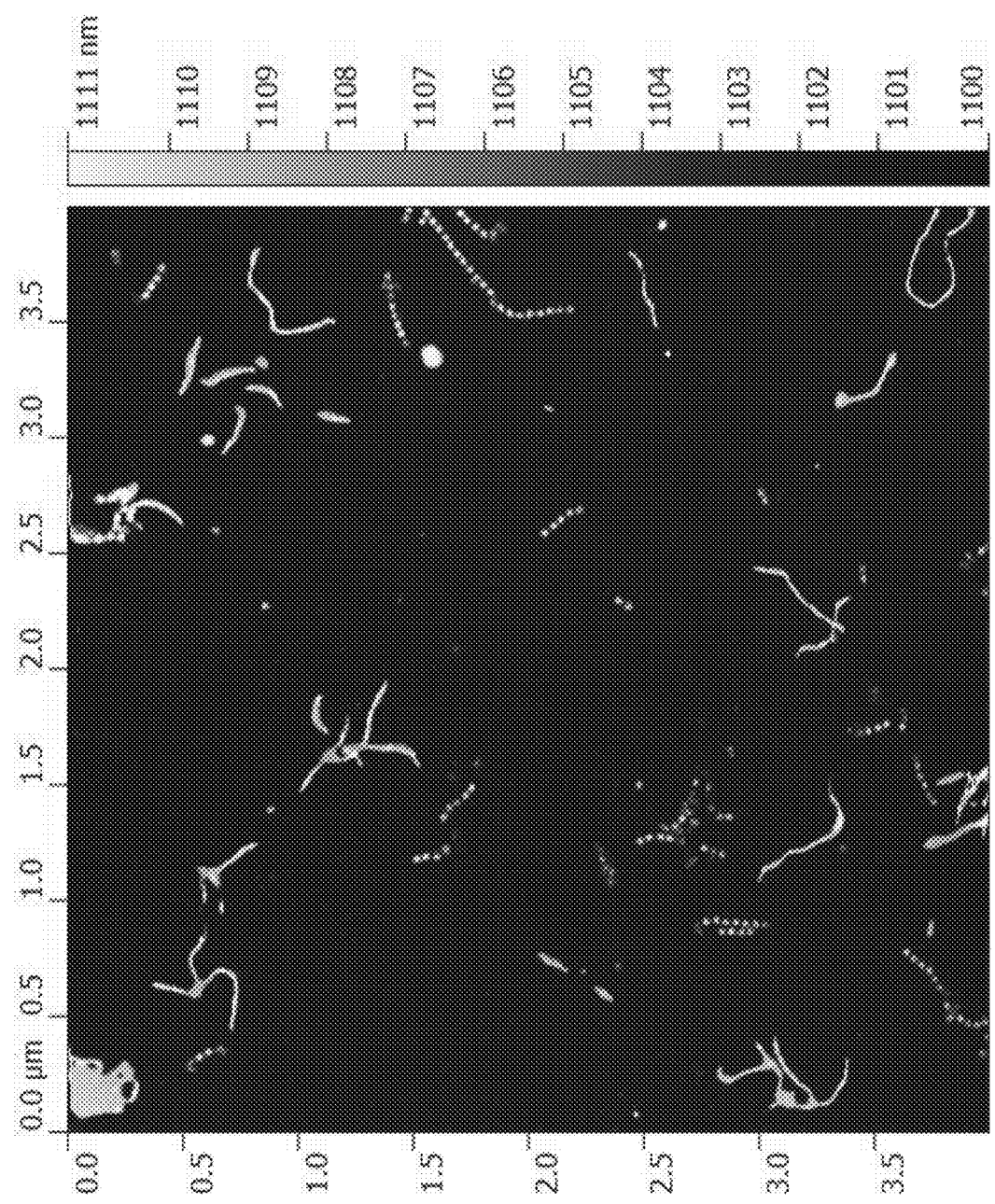
FIG. 5 shows and AFM micrograph of cholesterol-free $NP^{-C}$ deposited at a concentration of 2 nM on mica. The DNA nanopores assemble as chains of square-like structures. The square appearance is likely caused by the compression of the hollow nanostructures by the AFM cantilever. The other snake-like objects lacking separate squares are most likely chains of DNA pores but aggregated and altered in conformation by the $Ni^{2+}$ and $Mg^{2+}$ cations used to anchor the DNA to the mica substrate.
Figure 6A:
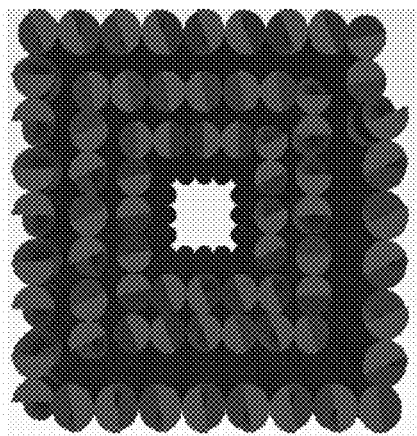
FIG. 6 shows rendering images of DNA nanopore NP designed using CaDNAno software and seen from the top (A), bottom (B), side (C), and angular side view (D). The cylinders represent DNA duplexes which are composed of scaffold strand (medium grey) and the staple polynucleotides (dark grey). Light grey strands are adaptor polynucleotides which hybridize with the unpaired single-stranded portion to cholesterol-modified anchor polynucleotides (not shown).
Figure 6B:
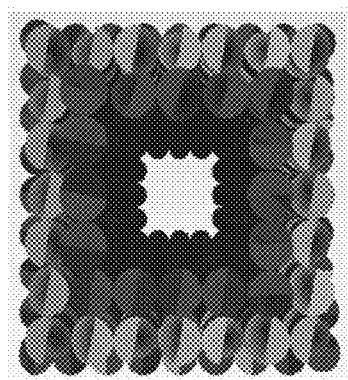
Figure 6C:
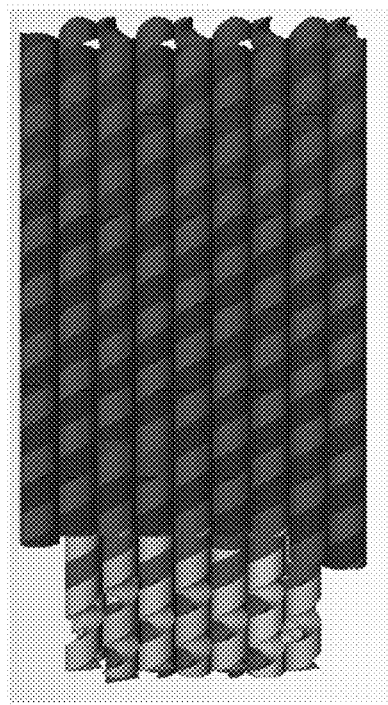
Figure 6D:
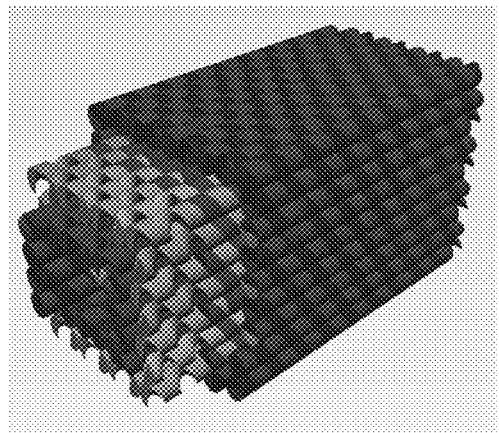

Atomic force microscopy (AFM) was applied to determine the dimensions of the synthesized DNA nanopores. The samples were incubated with $Mg^{2+}$ and $Ni^{2+}$ to adsorb the negatively charged nanostructures onto negatively polarized and atomically flat mica substrates. AFM micrographs of pore $NP^{-C}$ featured chain-like structures composed of multiple pores (FIG. 3B, top panel; FIG. 5). Related higher-order assemblies have been observed for other surface-adsorbed DNA nanostructures that are held together by counter-ions or blunt-end stacking (Burns J. R., Seifert A., Fertig N., Howorka S. *Nat. Nanotechnol.* 11, 152-156 (2016); Aghebat Rafat A., Pirzer T., Scheible M. B., Kostina A., Simmel F. C. *Angew. Chem. Int. Ed.* 53, 7665-7668 (2014)). It is certain that the multi-component chains solely formed due to substrate effects since SEC (FIG. 4) and gel electrophoresis (FIG. 3A) confirmed the monomeric nature of pores in solution. As shown by AFM analysis, the DNA nanopores of high aspect ratio adsorbed in lying orientation onto mica to maximize cation-mediated interaction with the negative substrate surface. Indeed, AFM profiles of separate DNA pores (FIG. 3B, middle and bottom panels) yielded an average elevation of 10.2±1.1 nm (n=19) in agreement with a lying pore that is compressed by the AFM cantilever tip (Burns J. R., Seifert A., Fertig N., Howorka S. A *Nat. Nanotechnol.* 11, 152-156 (2016)). The value of 10.2 nm is within the range obtained for other DNA structures also six duplexes thick (Schmied J. J., et al. *Nat. Protoc.* 9, 1367-1391 (2014)). Compression of the pore accounted for its square appearance (FIG. 3B) since DNA duplexes flanking the pore lumen are squeezed out. The squares had a side length of 36.0±10.5 nm (FWHM, n=19, FIG. 3B, bottom panel) which comprises both the broadened nominal width of 22.5 nm and the height of 35 nm of the pore's cap region. The majority of the transmembrane region of $NP^{-C}$ without cholesterol-containing strands is only 2 duplexes thick (FIGS. 6C and D) and hence less clearly imaged in AFM.

Figure 7:
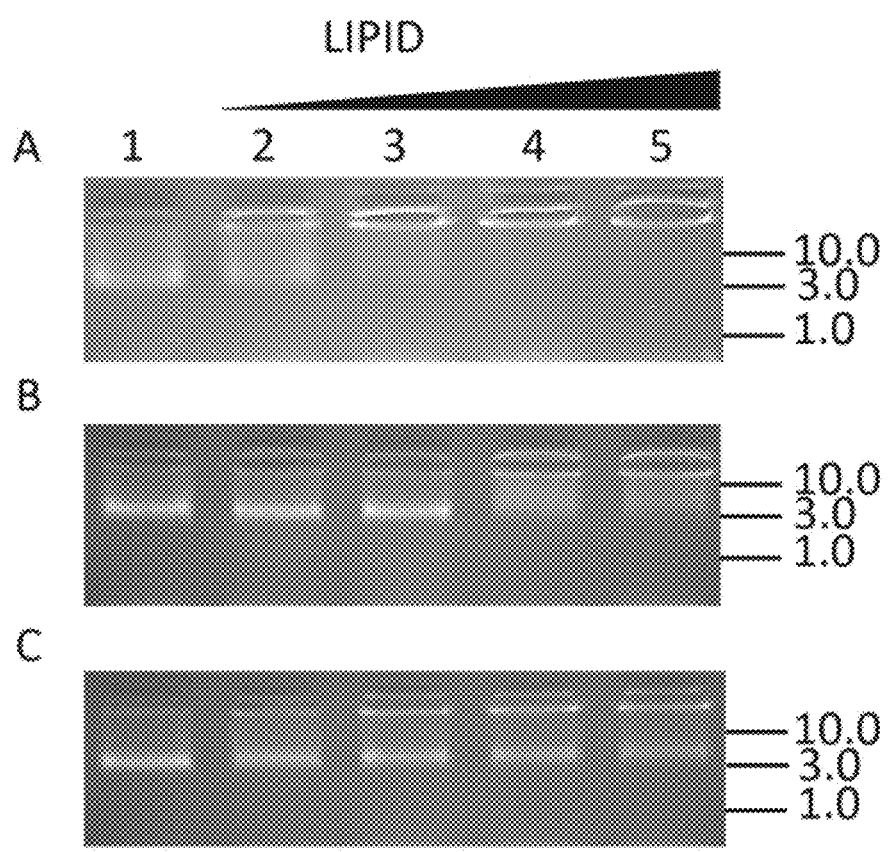
FIG. 7 shows gel electrophoretic analysis of the interaction between cholesterol-tagged DNA nanopores and lipid vesicles. (A) The DNA nanopores carried the lipid anchor at all 24 possible membrane-spanning duplexes. This corresponds to 12 DNA polynucleotides with the cholesterol TEG modification attached at the 5' terminus and 12 at the 3' terminus. (B, C) Gels for pores with (B) 12 lipid anchors at 5'-termini, and (C) 12 lipid anchors at 3'-termini. The lipid concentrations are 0.42 mM (lane 2), 0.58 mM (lane 3), 0.67 mM (lane 4), 0.75 mM (lane 5). The position and bp length of the dsDNA markers are given at the right of the gels.
Figure 8:
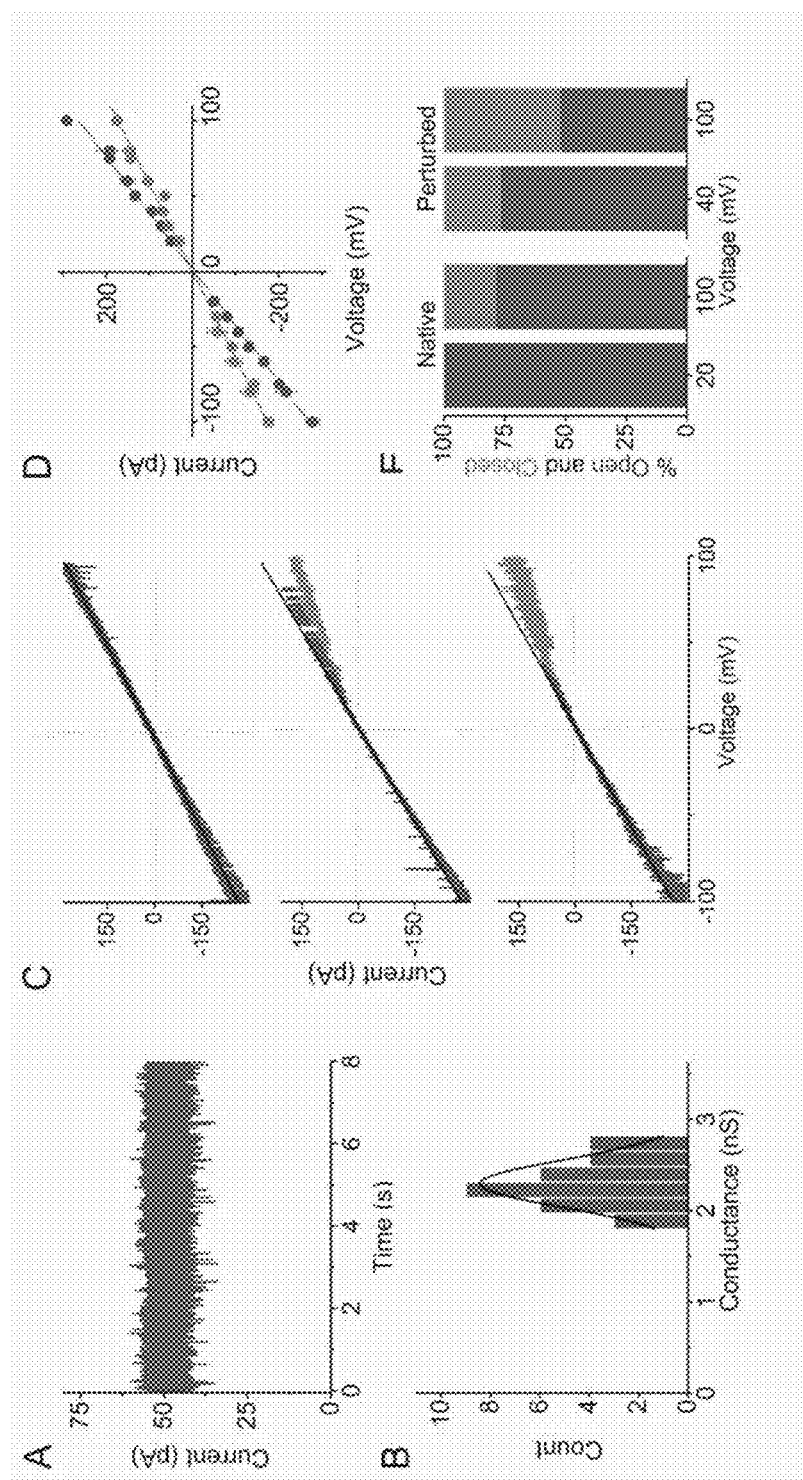
FIG. 8 shows an analysis via single-channel current recordings establishes that NP DNA nanopores span the lipid bilayer. (A) Representative ionic current trace of a single NP pore in 1 M KCl, 10 mM HEPES pH 8.0 and at +20 mV relative to the cis side of the membrane (FIG. 1A). (B) Histogram of channel conductances obtained from 32 independent single-channel recordings at +20 mV to +50 mV. (C) Traces of single DNA pores recorded at voltage ramps running from −100 to +100 mV. The high conductance state is color-coded in dark grey; the lower conductance state is coded in light grey. The traces were selected to show the lower conductance state and hence over-represent its actual frequency of occurrence. (D) IV curve displaying the averages and standard deviation from 10 single-channel current traces. (E) Probabilities for the higher and lower conductance state as a function of the magnitude of positive voltage. Native indicates that the pores were not exposed for at least 10 s to voltages switches while perturbed pores experienced in 1 s intervals at least 8 manually induced voltage switches from +/−40V to +/−100V in 20 mV steps. The probabilities were obtained from the cumulative all-point histogram analysis of multiple traces as described in FIG. 9.
Figure 9:
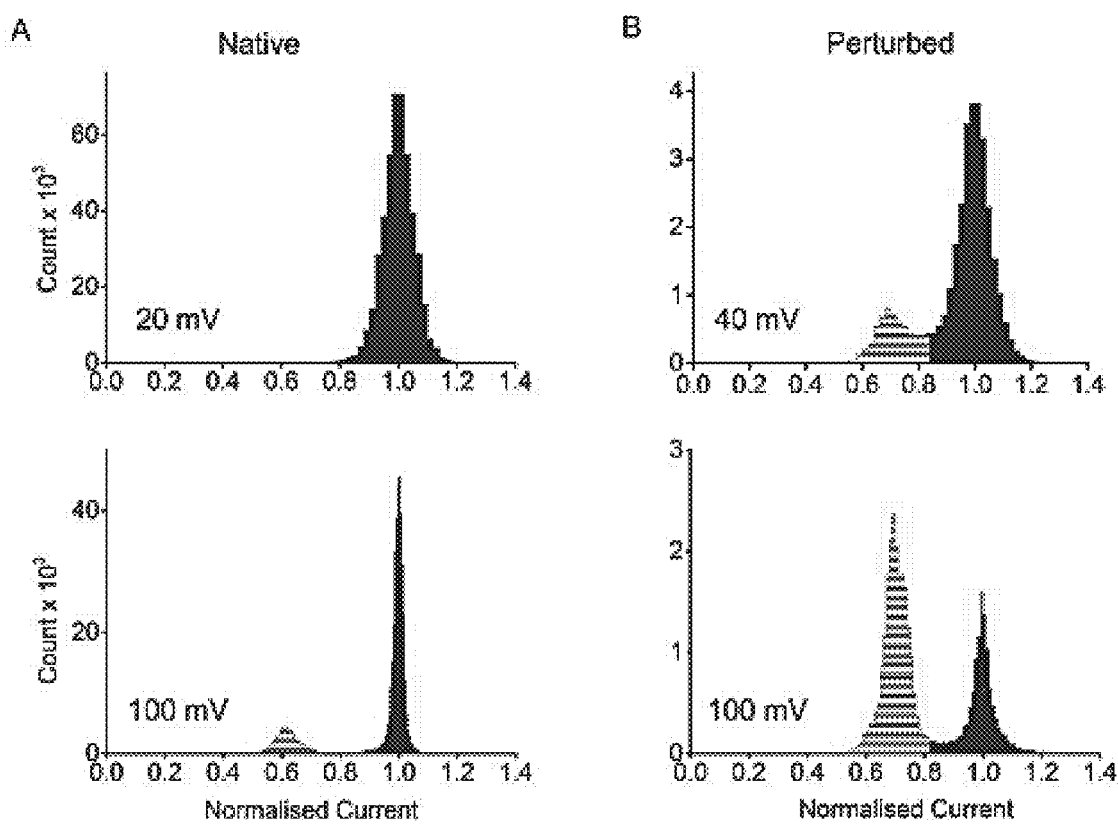
FIG. 9 shows all point histograms showing the current distributions of NP pores for the open, high conductance state (solid) and the party-closed lower conductance state (hatched). The current distributions were normalized to the open channel current. The distributions are for (A) native pores held at the recording potential for at least 10 s and (B) perturbed pores that had been exposed to multiple voltage switches at 1 s intervals. The recording potentials are indicated. Histograms for A were obtained by summing up three 15 s segments of independent traces for each voltage while histograms for B were from the sum of each seven 1s segments of independent traces.

The anchoring of cholesterol-tagged NP into lipid bilayers was established using a gel shift assay. In line with anchoring, the band for NP was upshifted and co-migrated with small unilamellar vesicles (SUVs) that were unable to enter the gel to remain in the loading slots (FIG. 8C). Increasing amounts of SUVs led to a complete conversion to the upshifted DNA band (FIG. 8C) implying that all pores interacted with the bilayer. By contrast, $NP^{-C}$ without anchors did not produce any gel shift (FIG. 8C), in agreement with the need of cholesterol for membrane insertion. Pores with half the number of cholesterol anchors led to an incomplete gel shift (FIG. 7).

The membrane-spanning nature of nanopore NP was confirmed with single-channel current recordings. Individual pores were inserted into a planar lipid bilayer (Del Rio Martinez J. M., Zaitseva E., Petersen S., Baaken G., Behrends J. C. *Small* 11, 119-125 (2015); Goyal P., et al. *Nature* 516, 250-253 (2014)) and a potential was applied across the membrane to induce flow of electrolyte ions (Burns J. R., Seifert A., Fertig N., Howorka S. *Nat. Nanotechnol.* 11, 152-156 (2016)). Under standard electrolyte conditions, a constant current of 49.5 pA was observed (FIG. 3A) at a potential of +20 mV relative to the cis side of the pore. The corresponding conductance distribution of 32 pores had a maximum of 2.29±0.26 nS (FIG. 3B). In agreement with the wide pore lumen, the conductance is 2.6-fold higher than the reference DNA pore of 2 nm diameter (Langecker M., et al. Synthetic lipid membrane channels formed by designed DNA nanostructures. *Science* 338, 932-936 (2012)). Calculating the theoretical conductance based on the geometry of NP yielded a value of 6.7 nS. But this is too high because the basic assumption of the model—a constant mobility of electrolyte ions as in bulk solution—is not valid for ionic transport in nanoscale confined pores with negatively charged walls (Ho C., Qiao R., Heng J. B., Chatterjee A., Timp R. J. Electrolytic transport through a synthetic nanometer-diameter pore. *Proc. Natl. Acad. Sci. USA* 102, 10455-10450 (2005)). Given the lower experimental conductance, it seems unlikely that ionic leakiness across the 3 duplex-thick pore wall plays a major role. Leakiness has previously been found in simulations for a single duplex pore wall (Maingi V., Lelimousin M., Howorka S., Sansom M. S. *ACS Nano* 9, 11209-11217 (2015)) and for ionic transport across a layered duplex structure that was oriented perpendicular to the electric field (Yoo J., Aksimentiev A. *Proc. Natl. Acad. Sci. USA* 110, 20099-20104 (2013); Plesa C., et al. *ACS Nano* 8, 35-43 (2014)) rather than parallel as in the case of NP. Voltage ramps established that NP was of ohmic behavior (FIG. 3C) as expected for a symmetrical pore. Above 30-40 mV, the pore could switch to a lower conductance state. The magnitude of the conductance drop at 30% (FIG. 3D) is considerably smaller than the value of 80% for previous DNA nanopores (Seifert A., Göpfrich K., Burns J. R., Fertig N., Keyser U. F., Howorka S. *ACS Nano* 9, 1117-1126 (2015); Burns J. R., Seifert A., Fertig N., Howorka S. A biomimetic *Nat. Nanotechnol.* 11, 152-156 (2016)). Furthermore, the probability of switching the conductance state is much lower for the new pores. Quantified as probability for the higher conductance state, the new large pores were open 100% at 20 mV and 75% at 100 mV (FIG. 3E, two left bars, "native") compared to 80% and 20%, respectively, for small DNA nanopores. The native and open state of large DNA pores could, however, be perturbed by repeated voltage switching to achieve a memory effect that results in a lower open probability (FIG. 3E, two right bars, "perturbed").

Pore NP was able to channel molecular cargo across the membrane as shown by the release of a fluorescent probe from lipid vesicles. Giant unilamellar vesicles (GUVs) were filled with poly(ethylene glycol) $PEG^{350}$ that was coupled to fluorescent dye fluoresceine amidite (FAM). Unlike fluorescence-tagged protein, $FAM-PEG^{350}$ of 2.4 nm diameter (Merzlyak P. G., Yuldasheva L. N., Rodrigues C. G., Carneiro C. M. M., Krasilnikov O. V., Bezrukov S. M. *Biophys. J.* 77, 3023-3033 (1999); Krasilnikov O. V., Rodrigues C.

Figure 10:
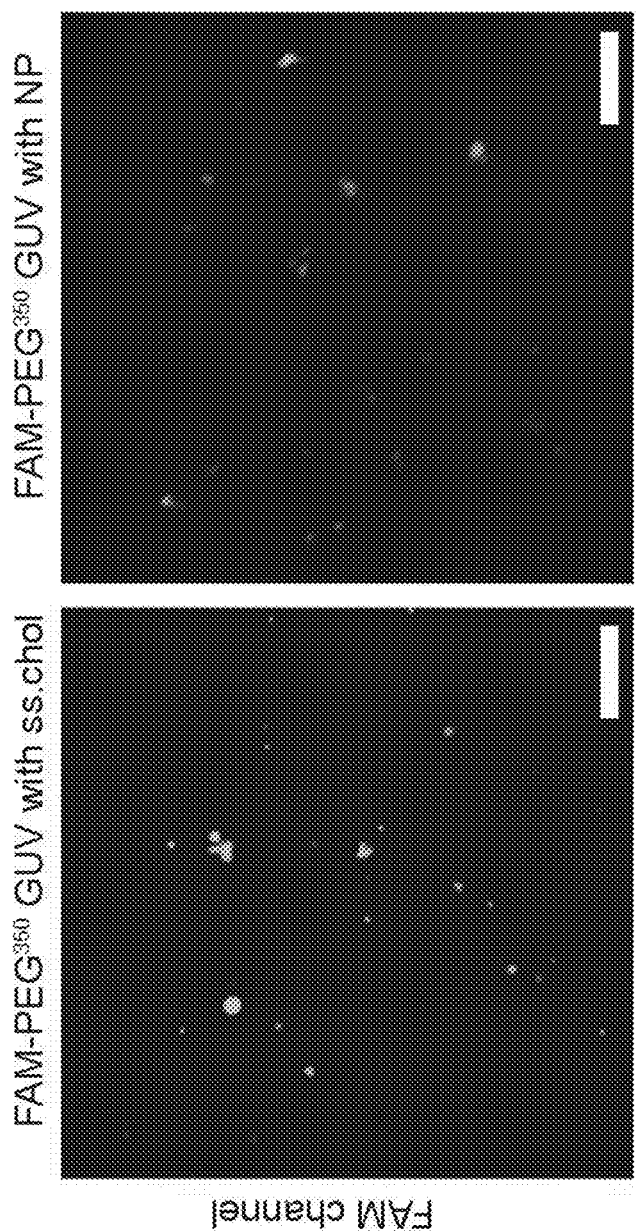
FIG. 10 shows Nanopore NP releasing fluorescent probe FAM-PEG$^{350}$ from giant unilamellar vesicles. Fluorescence images of PEG$^{350}$-FAM filled vesicles incubated with cholesterol-modified DNA polynucleotides (left) and NP (right).

G., Bezrukov S. M. *Phys. Rev. Lett.* 97, 018301 (018301-018304) (2006)) could be packed at high density into GUVs giving rise to a strong visual signal in fluorescence microscopic images (FIG. 10, left panel); the size distribution of GUVs was within the norm (Moscho A., Orwar O., Chiu D. T., Modi B. P., Zare R. N. *Proc. Natl. Acad. Sci. USA* 93, 11443-11447 (1996)). Addition of cholesterol-tagged NP led to a stark decrease in fluorescence while leaving the SUV shape unaffected (FIG. 10, right) strongly suggesting that the pore punctured holes into the membrane without rupturing it. In support of this interpretation, a negative control featuring cholesterol-modified DNA polynucleotides did not change the vesicle fluorescence (FIG. 104A, left) implying that membrane anchoring without pore activity does not lead to membrane puncturing.

Figure 11A:
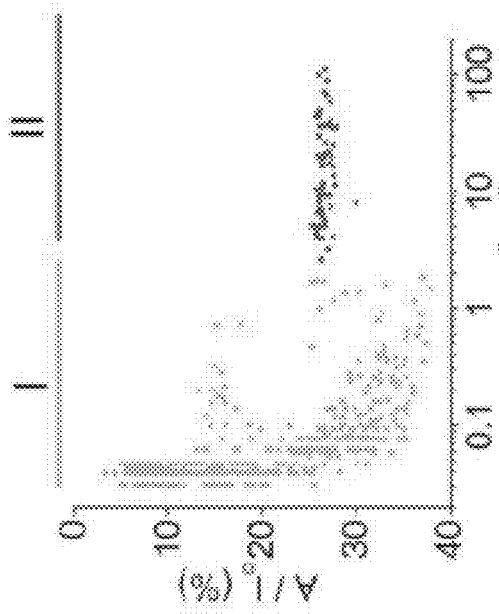
FIG. 11 shows transport of the protein trypsin through the NP pore. (A) Scheme of the DNA nanopore and its interaction with protein molecules leading to a short encounter without pore translocation (type I) or successful transport (type II). (B) Single-channel current trace recorded in the presence of 1.26 µM trypsin at the cis side leading to blockade of type I and II. Open channel current, $I_o$, blockade amplitude, A, and dwell time, $T_{off}$, are defined. (C) Scatter plot showing $T_{off}$ and A for a single-channel current recording with 1.26 µM trypsin in the cis chamber. Each point in the diagram represents an individual encounter event of protein with the DNA nanopore. The scatter plot comprises 568 data points.
Figure 11C:
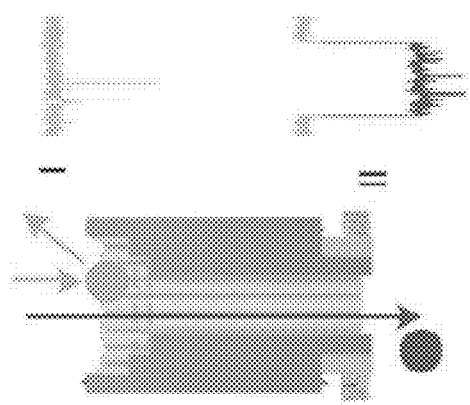
Figure 11B:
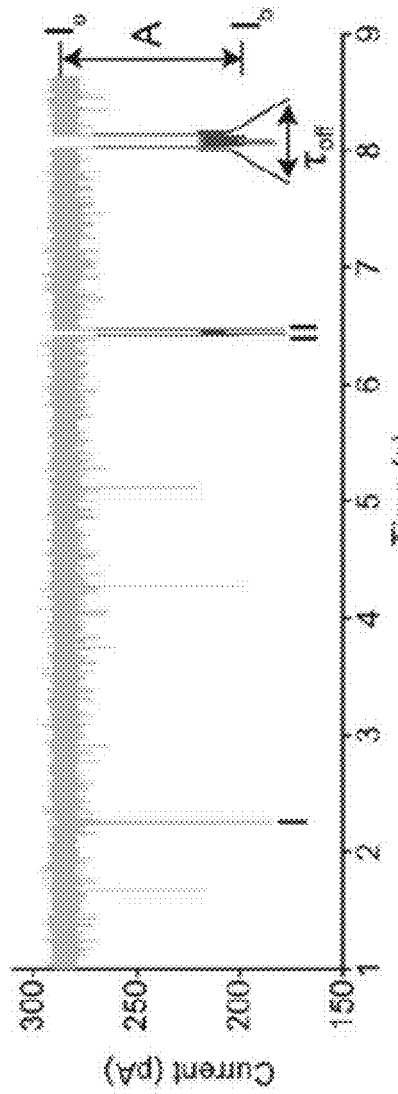

The transport of protein along the lumen of the DNA channel (FIG. 11) was examined with single-channel current recordings. Trypsin with a molecular size of 4.3×3.8×2.3 nm (pI 10.1) was selected as test protein. Upon its addition to the cis side, two types of current blockades occurred that differed in their duration, $\tau_{off}$. Shorter type I and longer type II events (FIG. 5B). The blockades also had different levels of amplitude A (FIG. 11B). When each event was plotted with its $\tau_{off}$ and A as separate point in a scatter diagram, the two blockade types clustered into two different regions (FIG. 11C). Type I had $\tau_{off}$ of less than 1 ms while type II featured $\tau_{off}$ values between 2-200 ms with an average of 17.5±5.5 ms (N=3) obtained from the fit to the single exponential decay distributions. As other distinguishing characteristic, only type II had a defined amplitude A of 26.2±0.7% (N=3) when normalized to the open channel current $I_0$ (FIG. 11C) while A of type I ranged from 5 to 35%.

In line with related current signatures through inorganic pores (Wei R. S., Gatterdam V., Wieneke R., Tampe R., Rant U. *Nat. Nanotechnol.* 7, 257-263 (2012); Yusko E. C., et al. *Nat. Nanotechnol.* 6, 253-260 (2011); Oukhaled A., et al. *ACS Nano* 5, 3628-3638 (2011)) type I events are interpreted as short transient contacts of protein with the pore (FIG. 11A, bright green) while type II are seen to represent the movement of trypsin through the DNA channel (FIG. 11B, dark green). This interpretation is supported by (i) the agreement between the longer duration of type II events and the expected long transport process through the pore. A further support is (ii) the match between the experimental amplitude of type II events and the calculated blockade level of 30%. The latter value was derived from the ratio of the cross-sectional areas of trypsin and the pore lumen. Finally, the narrow distribution of the current blockade is in line with the homogenous nature of current blockades caused by proteins that migrate through a channel of largely constant width.

Figure 12:
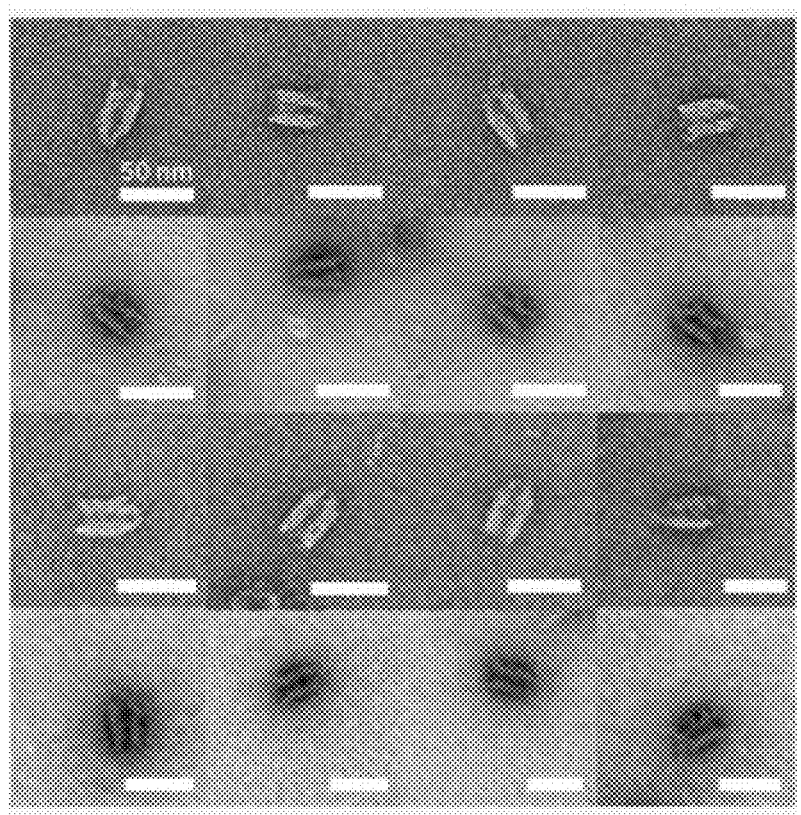
FIG. 12 shows representative tunnelling electron microscope (TEM) images for the DNA nanostructures according to the present invention. Scalebar=50 nm.
Figure 13:
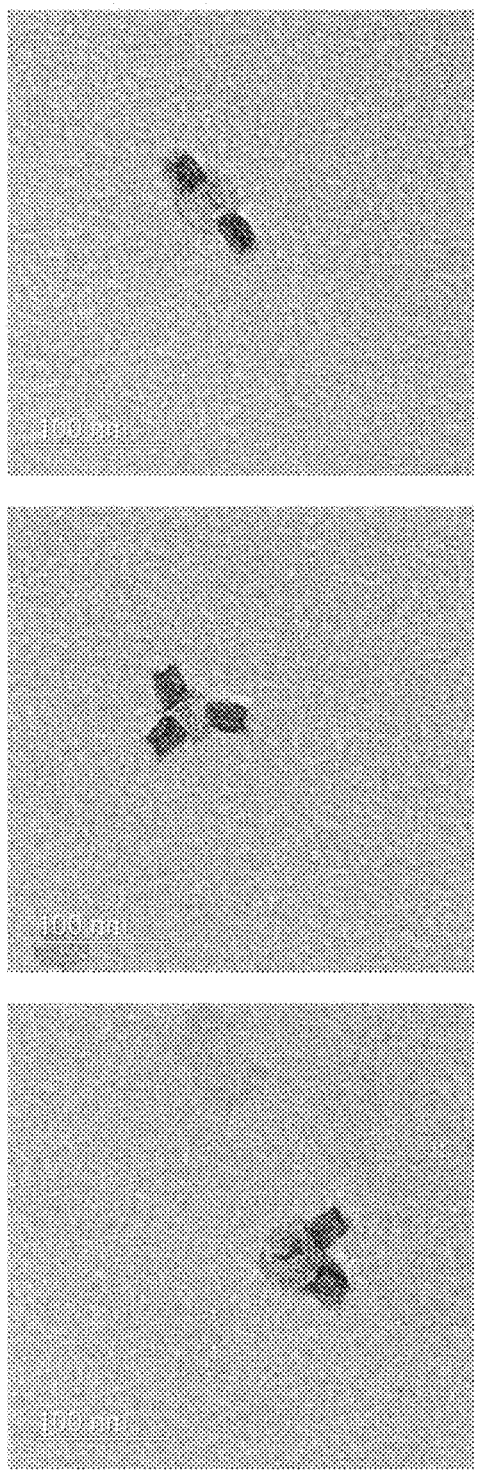
FIGS. 13 and 14 show representative tunnelling electron microscope (TEM) images for the DNA nanostructures according to the present invention attached on Single Unicellular Vesicles (SUVs). Scalebar=50 nm.
Figure 14:
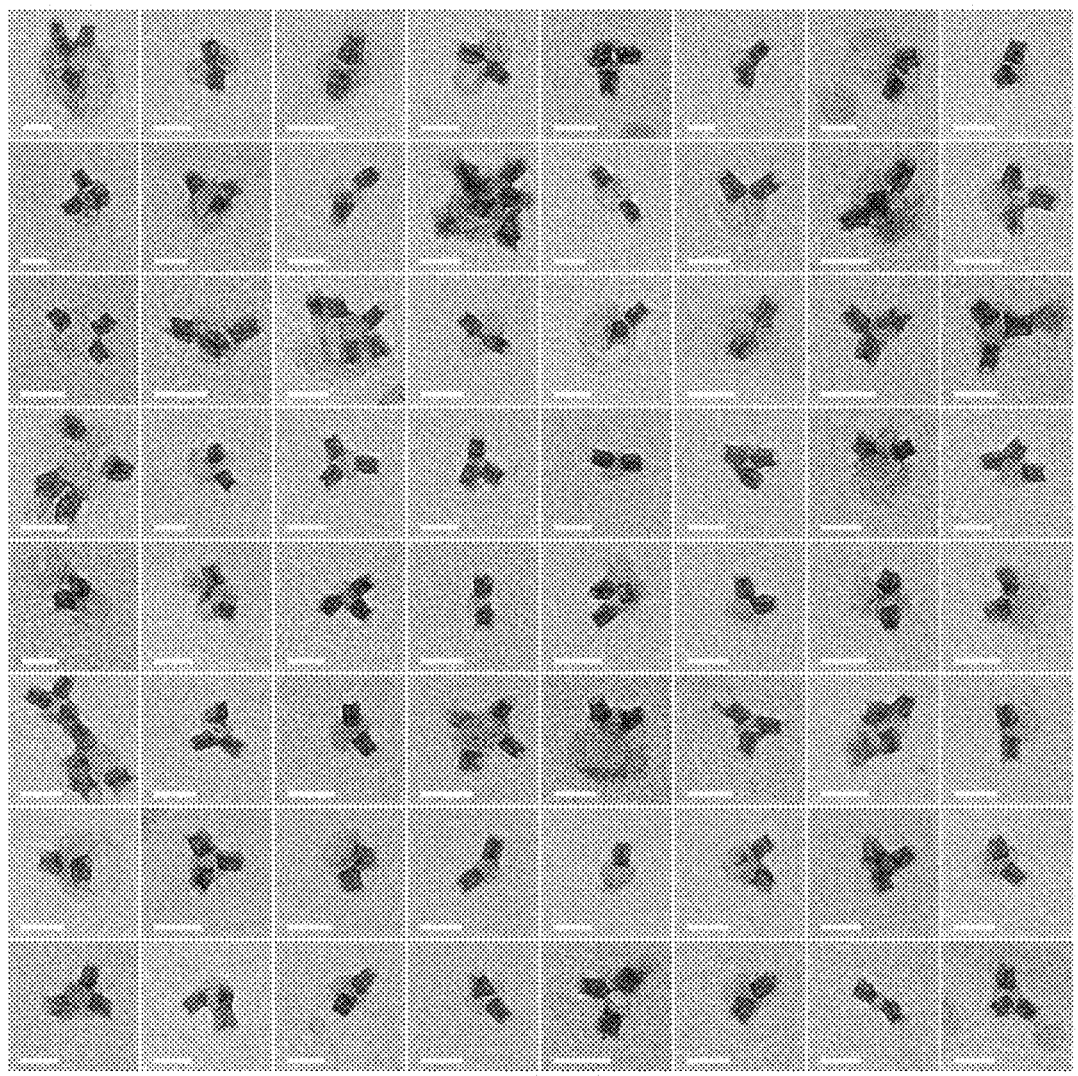

Transmission electron microscopy (TEM) images of the nanopores according to the present invention are shown in FIGS. 12 to 14. FIG. 12 shows TEM images of the DNA nanopores of the present invention. FIGS. 13 and 14 show TEM images for representative DNA nanopore structures attached on SUVs. The consistency of the pore structure is clearly shown in the images.

Example 2: Preparation and Insertion of DNA Nanopores into Synthetic Polymer Membranes Synthesis of PMPC-b-PDPA Membrane Polymersomes 2-(Methacryloyloxy)ethyl phosphorylcholine monomer (MPC, 99.9% purity) (ex. Biocompatibles U.K.); 2-(diisopropylamino)ethyl methacrylate (DPA) and remaining chemicals were bought from Sigma Aldrich. Block copolymer PMPC-PDPA was synthesized by atom-transfer radical-polymerization (ATRP) following a published protocol. [L. Ruiz-Perez, J. Madsen, E. Themistou, J. Gaitzsch, L. Messager, S. P. Armes, G. Battaglia, *Polym. Chem.* 2015, 6, 2065-2068] Briefly, a solution in morpholinoethylbromoisobutyric acid ester (ME-Br, synthesis described previously) [H. Lomas, I. Canton, S. MacNeil, J. Du, S. P. Armes, A. J. Ryan, A. L. Lewis, G. Battaglia, *Adv. Mater.* 2007, 19, 4238-4243.] (0.190 g, 0.68 mmol, 1 eq.) in EtOH (5 mL) was placed in a round-bottom flask before addition of MPC (5.000 g, 1.70 mmol, 25 eq.). The mixture was stirred and further purged with nitrogen for 30 min and heated to 30° C. Then, a mixture of 2,2'-bipyridine (bpy) (0.223 g, 1.42 mmol, 2 eq.) and copper(I) bromide (Cu(I)Br) (0.097 g, 0.68 mmol, 1 eq.) was added under a constant nitrogen flow. The mixture was stirred for 60 min to yield a highly viscous brown substance and sampled with NMR to estimate the extent of conversion. Meanwhile, a solution of DPA (12.27 g, 57.6 mmol, 85 eq.) in EtOH (13 mL) was prepared and purged with nitrogen for 60 min in a separate flask. DPA solution was added to the polymerization mixture, and the reaction solution was purged for another 10 min and left overnight at 30° C. After 18 h, $^1$H NMR analysis confirmed that the conversion was >99%. Upon diluting the reaction mixture in EtOH (30 mL), the solution gradually turned green, indicating oxidation of the copper-based catalyst. The mixture was passed through silica and the solvent was partially evaporated to give an opaque solution which was then dialyzed (MWCO 1,000 Da) against $CH_2Cl_2$, MeOH, and water (2 times each) for 8-14 h for each dialysis cycle. The polymer was freeze-dried and dried at 120° C. for 2 h under vacuum resulting in a yield of 13.3 g (77%). $^1$H NMR analysis in mixture of $CDCl_3$/MeOD (3:1) determined the composition of the polymer to be $PMPC_{25}$-$PDPA_{72}$. Size-exclusion chromatography (SEC) established that the polydispersity index (PDI) had a value of 1.22. All polymersome dispersions were prepared by thin film hydration (J. Gaitzsch, D. Appelhans, L. Wang, G. Battaglia, B. Voit, *Angew. Chem. Int. Ed.* 2012, 51, 4448-4451). Typically, block copolymer $PMPC_{25}$-$PDPA_{72}$ was dissolved in a mixture of $CHCl_3$ and MeOH (2:1, 5 mL) and then dried under vacuum at 30° C. overnight. The resulting dried polymer film was hydrated in PBS (5 mL) and stirred vigorously. After 7 weeks under stirring, the polymeric vesicle suspension was purified through centrifugation cycles. Briefly, an aliquot (500 μL) was centrifuged for 10 min at 1000 RCF. The supernatant was further centrifuged for 20 min at 23 000 RCF, and the resulting pellet was re-suspended in PBS (450 μL) and sonicated for 20 min, yielding a monodisperse suspension of polymeric vesicles. The concentration of $PMPC_{25}$-$PDPA_{72}$ within polymersome suspension was measured by UV-vis spectroscopy. Typically, a polymersome suspension (20 μL) was diluted 1:10 in PBS, pH 2.0, and the absorbance was recorded at A=220 nm. The concentration of $PMPC_{25}$-$PDPA_{72}$ was calculated using a calibration curve of the polymer. The polymersome size and its distribution were determined by dynamic light scattering as described in section 1.8. To calculate the number of polymersomes in a unit volume of suspension, the concentration of $PMPC_{25}$-$PDPA_{72}$ and the polymersome size were used as input variables for a Matlab® script which is based on several equations. Following equation (1), the number of polymersomes, $N_p$, is given by the experimentally determined total number of polymer chains, $N_c$, divided by the number of polymer chains per polymersome, $N_{agg}$.

$$N_p = \frac{N_c}{N_{agg}} \quad (1)$$

Nagg is defined in equation (2) as the ratio between the volume of the polymersome hydrophobic membrane, $V_p$, divided by the product of molecular volume of the PDPA block of the polymer, VPDPA, assuming a vesicle packing parameter p=1.

$$N_{agg} = \frac{V_p}{V_{PDPA}} \quad (2)$$

The molecular volume, $V_{PDPA}$, is defined as:

$$V_{PDPA} = \frac{M_{PDPA}}{\rho_{PDPA} N_A} \quad (3)$$

where $M_{PDPA}$ is the molar mass of the PDPA block, $\rho_{PDPA}$ is the bulk density of the hydrophobic chain and is 1.02 g/ml, and $N_A$ is the Avogadro number.

Insertion of DNA Nanopores into PMPC-b-PDPA Membrane

A solution of nanopores (0.005 µM, 25 µL, in 10 mM Tris, 10 mM NiCl$_2$ pH 7.4) was added to freshly cleaved mica and incubated for 5 min. at room temperature. The supernatant was then removed followed by the addition of buffer solution (25 µL, 10 mM Tris, pH 7.4) reducing the NiCl$_2$ concentration to ~1 mM.

Encapsulation of Trypsin into Polymersomes, their Purification by Size Exclusion Chromatography and Characterization by UV-Vis Spectroscopy Porcine trypsin (1000-2000 U/mg) may be encapsulated into polymersomes by electroporation following a published procedure (L. Wang, L. Chierico, D. Little, N. Patikarnmonthon, Z. Yang, M. Azzouz, J. Madsen, S. P. Armes, G. Battaglia, *Angew. Chem. Int. Ed.* 2012, 51, 11122-11125).

Briefly, a suspension of PMPC$_{25}$-PDPA$_{72}$ polymersomes (5 mg mL-1, 200 µL) and a solution of trypsin (25 mg mL-1, 200 µL) were gently mixed and placed into an electroporation cell. This mixture was subsequently transferred in the electroporator (Eppendorf 2510) and electroporated using 5 pulses of an AC electric field at a voltage of 2500 V with an interval of 30 s between each pulse. Polymersomes with encapsulated trypsin were purified from excess free trypsin by SEC using Sepharose 4B. The gel filtration medium (20% slurry in EtOH) was first washed multiple times with PBS and centrifuged (5000 RCF, 5 min). Sepharose was then packed into the chromatographic column and washed 5 times with PBS. The sample (400 µL) was applied to the column, and purified material was eluted by collecting 500 µL fractions. Isolated trypsin and polymersomes that was not exposed to trypsin were also purified to obtain the corresponding reference elution volumes (10-15 mL and 5-6 mL, respectively). The protein content in the SEC-purified polymersome fraction containing encapsulated trypsin was analyzed by UV-vis spectroscopy to obtain absorbance readings at 280 nm using a Carry Eclipse Varian spectrophotometer. To determine the PMPC$_{25}$-PDPA$_{72}$ polymer content, protein-free polymersomes that had been subjected to the same purification procedure as polymersomes with encapsulated trypsin were analyzed by UV-spectroscopy at 220 nm. The polymersome solution (20 µL) was diluted 10-fold in PBS at pH 2.0. The concentration of trypsin was PMPC$_{25}$-PDPA$_{72}$ was calculated from absorbance readings and calibration curves for PMPC$_{25}$-PDPA$_{72}$ polymer and trypsin in PBS at pH 2.0.

Enzymatic Assays of Polymersomes with Encapsulated Trypsin

Nanoreactor assays were carried out with SEC-purified polymersomes containing encapsulated trypsin. A suspension of polymersomes (14 µM trypsin, 0.62 mg mL-1 polymer, 50 µL) and solutions of DNA nanopores NP-3C or NP-0C (1 µM, 25 µL) and B-NAR-AMC peptide (1 mM, 25 µL) were added to PBS, pH 7.4 (100 µL). For the negative control, the DNA nanopore solution was replaced with PBS, pH 7.4 (25 µL). For the positive control without polymersomes and DNA nanopores, B-NAR-AMC peptide (1 mM, 25 µL) and trypsin solution (25 µM, 50 µL) were mixed with PBS, pH 7.4 (125 µL). To avoid immediate reaction in the positive control, a lower concentration of trypsin (500 nM, 50 µL) was used to lower the conversion rate. All measurements were recorded on a Carry Eclipse fluorescence spectrophotometer. The fluorescence emission of each mixture was monitored between 400 and 600 nm with λexc=380 nm.

In summary, described herein are rationally designed and structurally defined, unprecedented wide membrane pores. These pores provide a significant advantage compared to existing biogenic and synthetic channels and may have many potential applications including biosensing, synthetic biology, and DNA nanotechnology.

Unlike existing protein pores, the nanopores described herein meet the criteria of structural definition, a wide lumen of approximately 50 nm$^2$ cross-section, and a modular design for tunable size. The new DNA nanopore exceeds current DNA pores by a 10-times larger lumen and the higher structural stability, that is, a less extensive and less frequent lower conductance state. Since the lower conductance is likely caused by loose DNA termini that are normal in DNA nano-architectures, improved pores could be formed in future by ligating DNA termini to achieve a covalently closed structure. As a further advantage, the pore design is highly modular and takes advantage of tested structural principles in nanotechnology. It is realistic that the approach can be extended to build even wider or shorter DNA pores.

DNA pores that are wide enough to channel protein across a membrane open up many applications, for example use in sensors for protein detection. In other, equally exciting applications the pores could be adapted to create a molecular valve with a closable lid in order to regulate the flow of proteins across membranes (Burns J. R., Seifert A., Fertig N., Howorka S. A biomimetic *Nat. Nanotechnol.* 11, 152-156 (2016); Andersen E. S., et al. *Nature* 459, 73-76 (2009)). Valves may be used for drug delivery nanodevices (Mura S., Nicolas J., Couvreur P. *Nat. Mater.* 12, 991-1003 (2013)) that could be composed of stable vesicles with biocompatible polymer walls (Messager L., et al. *Angew. Chem. Int Ed.* in press (2016); Howse J. R., Jones R. A., Battaglia G., Ducker R. E., Leggett G. J., Ryan A. J. *Nat. Mater.* 8, 507-511 (2009)). DNA nanopores may also help generate molecular machines that selectively transport cargo across the membrane (Franceschini L., Soskine M., Biesemans A., Maglia G. *Nat. Commun.* 4, 2415 (2013)). Finally, the new insight into how to anchor large negatively charged DNA channels into hydrophobic bilayers will strongly benefit the development of other membrane-tethered DNA nanostructures. Indeed, only recently have lipid-anchored DNA materials (Edwardson T. G., Carneiro K. M., McLaughlin C. K., Serpell C. J., Sleiman H. F. *Nat. Chem.* 5, 868-875 (2013)) been built to mimic functions of membrane proteins such as to control access of molecules to a cell's interior or to determine membrane morphology (Kocabey S., et al. Membrane-assisted growth of DNA origami nanostructure arrays. *ACS Nano* 9, 3530-3539 (2015); Czogalla A., et al. *Angew. Chem. Int. Ed.* 54, 6501-6505 (2015); Johnson-Buck A., Jiang S., Yan H., Walter N. G. *ACS Nano* 8, 5641-5649 (2014); Yang Y., et al. *Nat. Chemistry* 8, 476-483 (2016); Xu W., et al. *J. Am. Chem. Soc.* 138, 4439-4447 (2016); Perrault S. D., Shih W. M. *ACS Nano* 8, 5132-5140 (2014). These biomimetic structures are of interest in basic research, biotechnology and biomedicine (Howorka S. Nanotechnology. Changing of the guard. *Science* 352, 890-891 (2016); Chen Y. J., Groves B., Muscat R. A., Seelig G. *Nat. Nanotechnol.* 10, 748-760 (2015))).

Although particular embodiments of the invention have been disclosed herein in detail, this has been done by way of example and for the purposes of illustration only. The aforementioned embodiments are not intended to be limiting with respect to the scope of the appended claims, which follow. The choice of nucleic acid starting material is believed to be a routine matter for the person of skill in the art with knowledge of the presently described embodiments. It is contemplated by the inventors that various substitutions, alterations, and modifications may be made to the invention without departing from the spirit and scope of the invention as defined by the claims.

| SEQUENCE LISTINGS | |
|---|---|
| SEQ ID No. 1 | AATGCTACTA CTATTAGTAG AATTGATGCC ACCTTTTCAG CTCGCGCCCC<br>AAATGAAAAT ATAGCTAAAC AGGTTATTGA CCATTTGCGA AATGTATCTA<br>ATGGTCAAAC TAAATCTACT CGTTCGCAGA ATTGGGAATC AACTGTTACA<br>TGGAATGAAA CTTCCAGACA CCGTACTTTA GTTGCATATT TAAAACATGT<br>TGAGCTACAG CACCAGATTC AGCAATTAAG CTCTAAGCCA TCCGCAAAAA<br>TGACCTCTTA TCAAAAGGAG CAATTAAAGG TACTCTCTAA TCCTGACCTG<br>TTGGAGTTTG CTTCCGGTCT GGTTCGCTTT GAAGCTCGAA TTAAAACGCG<br>ATATTTGAAG TCTTTCGGGC TTCCTCTTAA TCTTTTTGAT GCAATCCGCT<br>TTGCTTCTGA CTATAATAGT CAGGGTAAAG ACCTGATTTT TGATTTATGG<br>TCATTCTCGT TTTCTGAACT GTTTAAAGCA TTTGAGGGGG ATTCAATGAA<br>TATTTATGAC GATTCCGCAG TATTGGACGC TATCCAGTCT AAACATTTTA<br>CTATTACCCC CTCTGGCAAA ACTTCTTTTG CAAAAGCCTC TCGCTATTTT<br>GGTTTTTATC GTCGTCTGGT AAACGAGGGT TATGATAGTG TTGCTCTTAC<br>TATGCCTCGT AATTCCTTTT GGCGTTATGT ATCTGCATTA GTTGAATGTG<br>GTATTCCTAA ATCTCAACTG ATGAATCTTT CTACCTGTAA TAATGTTGTT<br>CCGTTAGTTC GTTTTATTAA CGTAGATTTT TCTTCCCAAC GTCCTGACTG<br>GTATAATGAG CCAGTTCTTA AAATCGCATA AGGTAATTCA CAATGATTAA<br>AGTTGAAATT AAACCATCTC AAGCCCAATT TACTACTCGT TCTGGTGTTC<br>TCGTCAGGGC AAGCCTTATT CACTGAATGA GCAGCTTTGT TACGTTGATT<br>TGGGTAATGA ATATCCGGTT CTTGTCAAGA TTACTCTTGA TGAAGGTCAG<br>CCAGCCTATG CGCCTGGTCT GTACACCGTT CATCTGTCCT CTTTCAAAGT<br>TGGTCAGTTC GGTTCCCTTA TGATTGACCG TCTGCGCCTC GTTCCGGCTA<br>AGTAACATGG AGCAGGTCGC GGATTTCGAC ACAATTTATC AGGCGATGAT<br>ACAAATCTCC GTTGTACTTT GTTTCGCGCT TGGTATAATC GCTGGGGGTC<br>AAAGATGAGT GTTTTAGTGT ATTCTTTCGC CTCTTTCGTT TTAGGTTGGT<br>GCCTTCGTAG TGGCATTACG TATTTTACCC GTTTAATGGA AACTTCCTCA<br>TGAAAAAGTC TTTAGTCCTC AAAGCCTCTG TAGCCGTTGC TACCCTCGTT<br>CCGATGCTGT CTTTCGCTGC TGAGGGTGAC GATCCCGCAA AAGCGGCTT<br>TAACTCCCTG CAAGCCTCAG CGACCGAATA TATCGGTTAT GCGTGGGCGA<br>TGGTTGTTGT CATTGTCGGC GCAACTATCG GTATCAAGCT GTTTAAGAAA<br>TTCACCTCGA AAGCAAGCTG ATAAACCGAT ACAATTAAAG GCTCCTTTTG<br>GAGCCTTTTT TTTTGGAGAT TTTCAACGTG AAAAAATTAT TATTCGCAAT<br>TCCTTTAGTT GTTCCTTTCT ATTCTCACTC CGCTGAAACT GTTGAAAGTT<br>GTTTAGCAAA ACCCCATACA GAAAATTCAT TTACTAACGT CTGGAAAGAC<br>GACAAAACTT TAGATCGTTA CGCTAACTAT GAGGGTTGTC TGTGGAATGC<br>TACAGGCGTT GTAGTTTGTA CTGGTGACGA AACTCAGTGT TACGGTACAT<br>GGGTTCCTAT TGGGCTTGCT ATCCCTGAAA ATGAGGGTGG TGGCTCTGAG<br>GGTGGCGGTT CTGAGGGTGG CGGTTCTGAG GGTGGCGGTA CTAAACCTCC<br>TGAGTACGGT GATACACCTA TTCCGGGCTA TACTTATATC AACCCTCTCG<br>ACGGCACTTA TCCGCCTGGT ACTGAGCAAA ACCCCGCTAA TCCTAATCCT<br>TCTCTTGAGG AGTCTCAGCC TCTTAATACT TTCATGTTTC AGAATAATAG<br>GTTCCGAAAT AGGCAGGGGG CATTAACTGT TTATACGGGC ACTGTTACTC<br>AAGGCACTGA CCCCGTTAAA ACTTATTACC AGTACACTCC TGTATCATCA<br>AAAGCCATGT ATGACGCTTA CTGGAACGGT AAATTCAGAG ACTGCGCTTT<br>CCATTCTGGC TTTAATGAAG ATCCATTCGT TTGTGAATAT CAAGGCCAAT<br>CGTCTGACCT GCCTCAACCT CCTGTCAATG CTGGCGGCGG CTCTGGTGGT<br>GGTTCTGGTG GCGGCTCTGA GGGTGGTGGC TCTGAGGGTG GCGGTTCTGA<br>GGGTGGCGGC TCTGAGGGAG GCGGTTCCGG TGGTGGCTCT GGTTCCGGTG<br>ATTTTGATTA TGAAAGATG GCAAACGCTA ATAAGGGGGC TATGACCGAA<br>AATGCCGATG AAAACGCGCT ACAGTCTGAC GCTAAAGGCA AACTTGATTC<br>TGTCGCTACT GATTACGGTG CTGCTATCGA TGGTTTCATT GGTGACGTTT<br>CCGGCCTTGC TAATGGTAAT GGTGCTACTG GTGATTTTGC TGGCTCTAAT<br>TCCCAAATGG CTCAAGTCGG TGACGGTGAT AATTCACCTT TAATGAATAA<br>TTTCCGTCAA TATTTACCTT CCCTCCCTCA ATCGGTTGAA TGTCGCCCTT<br>TTGTCTTTAG CGCTGGTAAA CCATATGAAT TTTCTATTGA TTGTGACAAA<br>ATAAACTTAT TCCGTGGTGT CTTTGCGTTT CTTTTATATG TTGCCACCTT<br>TATGTATGTA TTTTCTACGT TTGCTAACAT ACTGCGTAAT AAGGAGTCTT<br>AATCATGCCA GTTCTTTTGG GTATTCCGTT ATTATTGCGT TTCCTCGGTT<br>TCCTTCTGGT AACTTTGTTC GGCTATCTGC TTACTTTTCT TAAAAGGGC<br>TTCGGTAAGA TAGCTATTGC TATTTCATTG TTTCTTGCTC TTATTATTGG<br>GCTTAACTCA ATTCTTGTGG GTTATCTCTC TGATATTAGC GCTCAATTAC |

SEQUENCE LISTINGS

```
CCTCTGACTT TGTTCAGGGT GTTCAGTTAA TTCTCCCGTC TAATGCGCTT
CCCTGTTTTT ATGTTATTCT CTCTGTAAAG GCTGCTATTT TCATTTTTGA
CGTTAAACAA AAAATCGTTT CTTATTTGGA TTGGGATAAA TAATATGGCT
GTTTATTTTG TAACTGGCAA ATTAGGCTCT GGAAAGACGC TCGTTAGCGT
TGGTAAGATT CAGGATAAAA TTGTAGCTGG GTGCAAAATA GCAACTAATC
TTGATTTAAG GCTTCAAAAC CTCCCGCAAG TCGGGAGGTT CGCTAAAACG
CCTCGCGTTC TTAGAATACC GGATAAGCCT TCTATATCTG ATTTGCTTGC
TATTGGGCGC GGTAATGATT CCTACGATGA AAATAAAAAC GGCTTGCTTG
TTCTCGATGA GTGCGGTACT TGGTTTAATA CCCGTTCTTG GAATGATAAG
GAAAGACAGC CGATTATTGA TTGGTTTCTA CATGCTCGTA AATTAGGATG
GGATATTATT TTTCTTGTTC AGGACTTATC TATTGTTGAT AAACAGGCGC
GTTCTGCATT AGCTGAACAT GTTGTTTATT GTCGTCGTCT GGACAGAATT
ACTTTACCTT TTGTCGGTAC TTTATATTCT CTTATTACTG GCTCGAAAAT
GCCTCTGCCT AAATTACATG TTGGCGTTGT TAAATATGGC GATTCTCAAT
TAAGCCCTAC TGTTGAGCGT TGGCTTTATA CTGGTAAGAA TTTGTATAAC
GCATATGATA CTAAACAGGC TTTTTCTAGT AATTATGATT CCGGTGTTTA
TTCTTATTTA ACGCCTTATT TATCACACGG TCGGTATTTC AAACCATTAA
ATTTAGGTCA GAAGATGAAA TTAACTAAAA TATATTTGAA AAAGTTTTCT
CGCGTTCTTT GTCTTGCGAT TGGATTTGCA TCAGCATTTA CATATAGTTA
TATAACCCAA CCTAAGCCGG AGGTTAAAAA GGTAGTCTCT CAGACCTATG
ATTTTGATAA ATTCACTATT GACTCTTCTC AGCGTCTTAA TCTAAGCTAT
CGCTATGTTT TCAAGGATTC TAAGGGAAAA TTAATTAATA GCGACGATTT
ACAGAAGCAA GGTTATTCAC TCACATATAT TGATTTATGT ACTGTTTCCA
TTAAAAAAGG TAATTCAAAT GAAATTGTTA AATGTAATTA ATTTTGTTTT
CTTGATGTTT GTTTCATCAT CTTCTTTTGC TCAGGTAATT GAAATGAATA
ATTCGCCTCT GCGCGATTTT GTAACTTGGT ATTCAAAGCA ATCAGGCGAA
TCCGTTATTG TTTCTCCCGA TGTAAAAGGT ACTGTTACTG TATATTCATC
TGACGTTAAA CCTGAAAATC TACGCAATTT CTTTATTTCT GTTTTACGTG
CTAATAATTT TGATATGGTT GGTTCAATTC CTTCCATAAT TCAGAAGTAT
AATCCAAACA ATCAGGATTA TATTGATGAA TTGCCATCAT CTGATAATCA
GGAATATGAT GATAATTCCG CTCCTTCTGG TGGTTTCTTT GTTCCGCAAA
ATGATAATGT TACTCAAACT TTTAAAATTA ATAACGTTCG GGCAAAGGAT
TTAATACGAG TTGTCGAATT GTTTGTAAAG TCTAATACTT CTAAATCCTC
AAATGTATTA TCTATTGACG GCTCTAATCT ATTAGTTGTT AGTGCACCTA
AAGATATTTT AGATAACCTT CCTCAATTCC TTTCTACTGT TGATTTGCCA
ACTGACCAGA TATTGATTGA GGGTTTGATA TTTGAGGTTC AGCAAGGTGA
TGCTTTAGAT TTTTCATTTG CTGCTGGCTC TCAGCGTGGC ACTGTTGCAG
GCGGTGTTAA TACTGACCGC CTCACCTCTG TTTTATCTTC TGCTGGTGGT
TCGTTCGGTA TTTTTAATGG CGATGTTTTA GGGCTATCAG TTCGCGCATT
AAAGACTAAT AGCCATTCAA AAATATTGTC TGTGCCACGT ATTCTTACGC
TTTCAGGTCA GAAGGGTTCT ATCTCTGTTG GCCAGAATGT CCCTTTTATT
ACTGGTCGTG TGACTGGTGA ATCTGCCAAT GTAAATAATC CATTTCAGAC
GATTGAGCGT CAAAATGTAG GTATTTCCAT GAGCGTTTTT CCTGTTGCAA
TGGCTGGCGG TAATATTGTT CTGGATATTA CCAGCAAGGC CGATAGTTTG
AGTTCTTCTA CTCAGGCAAG TGATGTTATT ACTAATCAAA GAAGTATTGC
TACAACGGTT AATTTGCGTG ATGGACAGAC TCTTTTACTC GGTGGCCTCA
CTGATTATAA AAACACTTCT CAAGATTCTG GCGTACCGTT CCTGTCTAAA
ATCCCTTTAA TCGGCCTCCT GTTTAGCTCC CGCTCTGATT CCAACGAGGA
AAGCACGTTA TACGTGCTCG TCAAAGCAAC CATAGTACGC GCCCTGTAGC
GGCGCATTAA GCGCGGCGGG TGTGGTGGTT ACGCGCAGCG TGACCGCTAC
ACTTGCCAGC GCCCTAGCGC CCGCTCCTTT CGCTTTCTTC CCTTCCTTTC
TCGCCACGTT CGCCGGCTTT CCCCGTCAAG CTCTAAATCG GGGGCTCCCT
TTAGGGTTCC GATTTAGTGC TTTACGGCAC CTCGACCCCA AAAAACTTGA
TTTGGGTGAT GGTTCACGTA GTGGGCCATC GCCCTGATAG ACGGTTTTTC
GCCCTTTGAC GTTGGAGTCC ACGTTCTTTA ATAGTGGACT CTTGTTCCAA
ACTGGAACAA CACTCAACCC TATCTCGGGC TATTCTTTTG ATTTATAAGG
GATTTTGCCG ATTTCGGAAC CACCATCAAA CAGGATTTTC GCCTGCTGGG
GCAAACCAGC GTGGACCGCT TGCTGCAACT CTCTCAGGGC CAGGCGGTGA
AGGGCAATCA GCTGTTGCCC GTCTCGCTGG TGAAAAGAAA AACCACCCTG
GCGCCCAATA CGCAAACCGC CTCTCCCCGC GCGTTGGCCG ATTCATTAAT
GCAGCTGGCA CGACAGGTTT CCCGACTGGA AAGCGGGCAG TGAGCGCAAC
GCAATTAATG TGAGTTAGCT CACTCATTAG GCACCCCAGG CTTTACACTT
TATGCTTCCG GCTCGTATGT TGTGTGGAAT TGTGAGCGGA TAACAATTTC
ACACAGGAAA CAGCTATGAC CATGATTACG AATTCGAGCT CGGTACCCGG
GGATCCTCTA GAGTCGACCT GCAGGCATGC AAGCTTGGCA CTGGCCGTCG
TTTTACAACG TCGTGACTGG GAAAACCCTG GCGTTACCCA ACTTAATCGC
CTTGCAGCAC ATCCCCCTTT CGCCAGCTGG CGTAATAGCG AAGAGGCCCG
CACCGATCGC CCTTCCCAAC AGTTGCGCAG CCTGAATGGC GAATGGCGCT
TTGCCTGGTT TCCGGCACCA GAAGCGGTGC CGGAAAGCTG GCTGGAGTGC
GATCTTCCTG AGGCCGATAC GGTCGTCGTC CCCTCAAACT GGCAGATGCA
CGGTTACGAT GCGCCCATCT ACACCAACGT AACCTATCCC ATTACGGTCA
ATCCGCCGTT TGTTCCCACG GAGAATCCGA CGGGTTGTTA CTCGCTCACA
TTTAATGTTG ATGAAAGCTG GCTACAGGAA GGCCAGACGC GAATTATTTT
TGATGGCGTT CCTATTGGTT AAAAAATGAG CTGATTTAAC AAAAATTTAA
CGCGAATTTT AACAAAATAT TAACGTTTAC AATTTAAATA TTTGCTTATA
CAATCTTCCT GTTTTTGGGG CTTTTCTGAT TATCAACCGG GGTACATATG
ATTGACATGC TAGTTTTACG ATTACCGTTC ATCGATTCTC TTGTTTGCTC
```

| | SEQUENCE LISTINGS |
|---|---|
| | CAGACTCTCA GGCAATGACC TGATAGCCTT TGTAGATCTC TCAAAAATAG<br>CTACCCTCTC CGGCATTAAT TTATCAGCTA GAACGGTTGA ATATCATATT<br>GATGGTGATT TGACTGTCTC CGGCCTTTCT CACCCTTTTG AATCTTTACC<br>TACACATTAC TCAGGCATTG CATTTAAAAT ATATGAGGGT TCTAAAAATT<br>TTTATCCTTG CGTTGAAATA AAGGCTTCTC CCGCAAAAGT ATTACAGGGT<br>CATAATGTTT TTGGTACAAC CGATTTAGCT TTATGCTCTG AGGCTTTATT<br>GCTTAATTTT GCTAATTCTT TGCCTTGCCT GTATGATTTA TTGGATGTT |
| SEQ ID No. 2 | GGAACAAATCATATATCCCACAAGCTTACCGAAGCTTGATTTCGGTCG |
| SEQ ID No. 3 | AAATGTTACAAAATCGCGCAAAA |
| SEQ ID No. 4 | TAACACCACCAGAGCCACC |
| SEQ ID No. 5 | GAAGGGTTAGAACCTTATACTTCTGAATAA |
| SEQ ID No. 6 | CATTAAGTAAGCATGAGCGCTCCCTGAACTCTGG |
| SEQ ID No. 7 | CCAAGCGTTGAGCCAAGGTGAATGTCA |
| SEQ ID No. 8 | GTGCATTAATTAGCTCGAATTCGTAATC |
| SEQ ID No. 9 | AAAATTCGAACCAATACTCCCGACAAAGCACTC |
| SEQ ID No. 10 | ACGGCCAGTAGCTGTTTCCTGTGTGAAATTGTTAT |
| SEQ ID No. 11 | CTCAAGTGTAAGAATCATAACCGAGTAAAAGAACG |
| SEQ ID No. 12 | TAAGAAGAAAATCTACAAAGCCGGAGACAGTCAAATCAC |
| SEQ ID No. 13 | GGCTCCATTAATTGTCGAAC |
| SEQ ID No. 14 | TATTTCAGAGCGGATGGTTGCTTTGACGAACGCT |
| SEQ ID No. 15 | GGCTGAATTTAGCCTTGAGT |
| SEQ ID No. 16 | AAAGTTACCAGATAAAGAGGACTAAAGCGATTATA |
| SEQ ID No. 17 | TGAGTCAGAAGGAGCGGAATTATCATCATATATAATCAGC |
| SEQ ID No. 18 | CGCACTTCCAAGAAGATAAGTGTATAGCCGGATTAGGA |
| SEQ ID No. 19 | AACAACATGTTCAAGAGAACGGAATAGG |
| SEQ ID No. 20 | GATAATTTGCCTTGCTAAAGCGAATAAT |
| SEQ ID No. 21 | AACTAGCAACGGCTACAGAGTC |
| SEQ ID No. 22 | AACAGTGAGACTCCTCAGCTAATGCAGATAAGGCT |
| SEQ ID No. 23 | AGAACCCCAGTCACACCAATCAATCCT |
| SEQ ID No. 24 | AGAACGTGGACATCAAGTTTTCAATTATTGCTCCTGCT |
| SEQ ID No. 25 | ACCGGAACCAGTAGCGTAATT |
| SEQ ID No. 26 | ATTTAACAAGCTGGCGAACTGTTGGGAAGGGCCGG |
| SEQ ID No. 27 | AGAACTGATAAAGCTAAAGGGTGAGA |
| SEQ ID No. 28 | AACCATCGCCCCACTACGACTTATTACACCAGCGC |
| SEQ ID No. 29 | TTTATTTCGCAATCAATAGGAGGGAGGGCACC |
| SEQ ID No. 30 | ATCGAGAAGATGGGCGGAACAAACGGCGGATTGAC |
| SEQ ID No. 31 | TATTTCGGATAATCTTGACAATTATAT |
| SEQ ID No. 32 | TGCGGGTTTTCCCAGTCACATTACGCCACGCC |
| SEQ ID No. 33 | CCACCCTCAAGACAAAGAGTC |
| SEQ ID No. 34 | CAAATAAGAAAATCGTAAAAAACAAGAGAATC |
| SEQ ID No. 35 | CTAAAGCATCACAATATCTGGTCAGTTGCACTAACGCAGCCTTTACAG |
| SEQ ID No. 36 | GAACGTAGAAATTAAACGGGAATACACT |

-continued

| SEQUENCE LISTINGS | |
|---|---|
| SEQ ID No. 37 | CCACGCTGAGAAAGGAATTG |
| SEQ ID No. 38 | ATGTAGAAACGACCAGAATACCTACATTTTGATTA |
| SEQ ID No. 39 | CATGAGGATGCAGGGACGAGG |
| SEQ ID No. 40 | AACGCGCGGGGAGGCAACAGCCTACCTTTGTCGC |
| SEQ ID No. 41 | AACGGAACGCCGCCAGCTTT |
| SEQ ID No. 42 | CATTCTGGCCTCTTTAAT |
| SEQ ID No. 43 | GATAGCCGATCAGCTTCCGCTT |
| SEQ ID No. 44 | CGCAGAGCCACGCCACCCTCAGAACCGACCAA |
| SEQ ID No. 45 | CCCTCATAGGTAAATGCTGAACAATCGGCC |
| SEQ ID No. 46 | AACCTCAACCACCAGCGTATTCTATATTTTCACCT |
| SEQ ID No. 47 | TGCCTCATTAAATGCCCCCTGCC |
| SEQ ID No. 48 | AAATTAAGAAATGACCCTGTAATA |
| SEQ ID No. 49 | GTAGCGGAAATTAACGGAATAGACCCCCAGCTTTTT |
| SEQ ID No. 50 | AGCCGGAAGCATAGTTAGAATTAGTTAATCCAAT |
| SEQ ID No. 51 | GACAGCCGGAAACCAGGCAAAGCGC |
| SEQ ID No. 52 | GCAATATTGACTCAACATGTTTTAAATATGCA |
| SEQ ID No. 53 | GGCGGTCAGTATTAACACCGGCGCGAA |
| SEQ ID No. 54 | GAATCGTCGACTGGATAAACATGATAGTAC |
| SEQ ID No. 55 | CTAGTCAAAAACGTCTTTCCCCTCAATCCTTGCTG |
| SEQ ID No. 56 | ATGAACGGTGTACAGACTTTGA |
| SEQ ID No. 57 | AATTCAATATAAAATCGG |
| SEQ ID No. 58 | AATGCACGCATAAAGAACTGGAAATAGCATATTTCAAAAA |
| SEQ ID No. 59 | ACAAATATCAGTAATGCCGATTCAACCGTTCTAGC |
| SEQ ID No. 60 | CGACGGCTGGTAATATCCAGAACAATACGCTCAATAAT |
| SEQ ID No. 61 | CATCAACTCTCCGTGGCATCGTAACCGTGCATCTGC |
| SEQ ID No. 62 | TGATAGCGATAAATTACCTTAGCCCGAAGTGTTGTTCCAGTTTCACT |
| SEQ ID No. 63 | TGAGTAATGAATATGATGAGAGGGTA |
| SEQ ID No. 64 | CTGAGGCTAGTTTCCAATACATACTTGTCACAAAT |
| SEQ ID No. 65 | AGAGGCTGCCCGTATATCAGCCAT |
| SEQ ID No. 66 | CTTTTGCGGGAAATAAAGATAACG |
| SEQ ID No. 67 | CGCCACCCTCAGAACAGGCGCATAGGTTCATCAAGAGACCTATTATT |
| SEQ ID No. 68 | CATTTTTTCATTAAATAAAGGAATGAGAT |
| SEQ ID No. 69 | TTGCAATCCAAAATAAACAGAAGATTGATTTTGTT |
| SEQ ID No. 70 | CTAAAACACGCGCCCAAATCAGAT |
| SEQ ID No. 71 | GAGACCCAATTCTGCAGTACCTTTTACATC |
| SEQ ID No. 72 | CGATTAAGTTGGGAATCCCCCTGACCATAAATCA |
| SEQ ID No. 73 | CATCTGTAGGTAAGGGTAAT |
| SEQ ID No. 74 | CACCAACCTAAGAAACGTC |

| SEQUENCE LISTINGS |
| --- |
| SEQ ID No. 75   ATGAGCAATACAGTGTTTTTATAATCACACAATTCACG |
| SEQ ID No. 76   CGGTACGATTTTGAGAATTATCTTAAACAGCCC |
| SEQ ID No. 77   CCAGCATTGGAAAGCCGTAAAATCAGGTCTTGCCCGCTTGGGCGCCAGGG |
| SEQ ID No. 78   AATTTCATTTGGCTTAGATGAAA |
| SEQ ID No. 79   TTCCGGTCCACTTCACCAGT |
| SEQ ID No. 80   CAGGAGTGTACTGGTAATAAGGGTTTTGCTCTGT |
| SEQ ID No. 81   ACTCTAGACGCGCCTGTTTACTTCTGGTGTATCGG |
| SEQ ID No. 82   ATTTACATAAATTTCCCTTCAACCGCCTGGC |
| SEQ ID No. 83   GCGACCACACCCGCCGCGCTCTACAGGG |
| SEQ ID No. 84   ATTTTGCGGGACTCATAGTCCACCACCCCGT |
| SEQ ID No. 85   AAATATCTAGCGCGTTCACCGACCGAAA |
| SEQ ID No. 86   ATCCCATAATCGGCCGTAACAATAGAAGGCCCAG |
| SEQ ID No. 87   AGACAAAAGGGAAAATTAAAATAC |
| SEQ ID No. 88   GCCTAATGAGTGAGGTCGTGCCGGTTTGAATTATA |
| SEQ ID No. 89   TTAGACGTTAGCAAAAAAAA |
| SEQ ID No. 90   GAGTAGAAACCGTTGTCGTTATACAAAAAGCCATA |
| SEQ ID No. 91   CACCGGCAAAAGATTAAG |
| SEQ ID No. 92   ATTATAAAGGTACATCCAATAAATTGCGTAGA |
| SEQ ID No. 93   TGCTCATTCAGTGAATAAGTTTCATCGGCATTTTCGGTCACAACG |
| SEQ ID No. 94   TAAATCCTTTTTATCAGA |
| SEQ ID No. 95   AGCATTCCACATGGGATTAGTTA |
| SEQ ID No. 96   GCAAATACCCAAACCGATATAACCGATAGAACAA |
| SEQ ID No. 97   GAGACGGAGGCGGTTAGGTTGGGATACCGACGCAG |
| SEQ ID No. 98   GCTATTTCCTGAGAGAAAGTCAGATTTA |
| SEQ ID No. 99   TAATATTAGACGGTGTTTAACAAGGAATTCAACTTTC |
| SEQ ID No. 100  CAGACGATTGGCCTTGCATTA |
| SEQ ID No. 101  AAAACACCACCAGTAGAAGGTAAAAAGAAGATTATTCAT |
| SEQ ID No. 102  GATCTAATCTTTCCAGGAATACCGAAAGATTCCGG |
| SEQ ID No. 103  CATTCGCCATTCAAATGTTTAATAAATATAACAGTTAAGCCAGAATGAC |
| SEQ ID No. 104  TAAAATATCTTTAGGAGGCAAATCAACAGTTG |
| SEQ ID No. 105  GGGCGATGGTTTTGCGGATG |
| SEQ ID No. 106  GAATAGAAAGGTTGCGCCGAAAACAGGTAAGCCCAGTT |
| SEQ ID No. 107  TGGTGGCATCATAAAGCCTCAG |
| SEQ ID No. 108  AACGGATTCGCCTGAAACAGTTGATTAACA |
| SEQ ID No. 109  CCTTATCAAAATCAGAGCCCACCCTCAG |
| SEQ ID No. 110  CAAAATCCCTTATAAATGGCGCTGGAGAAT |
| SEQ ID No. 111  AGCCAGCAGCAAATGAAAAATCTACAATTTTATACCAACG |
| SEQ ID No. 112  CAGTTGCACGTAAAACAGAGAAGCCTTATAGC |
| SEQ ID No. 113  CCGTCAATATATCAAACAGAGCCTTAGTTGCTACT |

-continued

| SEQUENCE LISTINGS |
|---|

SEQ ID No. 114 AATTTACGAGCAGTACCGAAGCCATTGACTTGCCT

SEQ ID No. 115 CAGAAAGTAATTCAGTACCAGGCG

SEQ ID No. 116 GCGCAAAGGGGATGTGCTGCAAGG

SEQ ID No. 117 CAAATTAGCCCCCTTATTAGCGTTTGCAGGT

SEQ ID No. 118 AGACAATATTTTTGAATG

SEQ ID No. 119 GGATGAGGTCATCCCACTACGTGA

SEQ ID No. 120 TTTCGCAATAAAATCATACAGGCAAGGCAAAGAATAAA

SEQ ID No. 121 TTGAGGCTATCAGGTCATTGTTGAGAGAATCTA

SEQ ID No. 122 TTGCCAGACGAGAGGCACCGCCACATAGTAAGTAA

SEQ ID No. 123 GCGCTAGCAAAAGAATTTTTAATAAGAAAACCGAC

SEQ ID No. 124 GAGGCCCTCAGAGTAGCGTAAC

SEQ ID No. 125 GTACGAACCGATTAAAATTCAAGGCAAAAGTAAAATACGT

SEQ ID No. 126 ATTTTTAGAACCCGAAACCACAACATTATCATTTTGCAGA

SEQ ID No. 127 ATAAACTAATAGATTTAGAAGTATTAGTTTTAAAAATAATAAG

SEQ ID No. 128 CCAAGAAAAATCGTCTGAAATGGAAGCCAGCTTTCGAT

SEQ ID No. 129 AGAATAATTTAATAGCTGCATTAATGGTGCTTTC

SEQ ID No. 130 CTTATGCGAAATTAAGCAAATTCTACTA

SEQ ID No. 131 GTTATTAAACTTTACAAACAATTC

SEQ ID No. 132 CTAAAACACCGAGCCTGGGGT

SEQ ID No. 133 GACGCTGAGAAGAACGCGACGCGT

SEQ ID No. 134 TAAAGGAGGTTAAGTATTA

SEQ ID No. 135 GATTGATAAATAGAGATAATTTAAATGCAATGCC

SEQ ID No. 136 TTGGATAGCCGGCGAACGTGAAGGGAA

SEQ ID No. 137 GGTCAATAACCTGTTTAGCTATAGCATTAGGCAA

SEQ ID No. 138 GCGAGTGAATTTGAAAACAAACCATCGCAAGG

SEQ ID No. 139 TCTCTTAATTGAGAATCTTGTAACGCCACTGCAGGTCGACTCTAGAGGA

SEQ ID No. 140 TCCAAAATCTCTAAATGAA

SEQ ID No. 141 AGGAAAGCGGATTGCATCTTTGCGTATTTCCAGTC

SEQ ID No. 142 TTGTGTCGAAATCCGCAAAGACAGCATATAAAGCCTGCGG

SEQ ID No. 143 AATCGTAACCAAAGGAGCGG

SEQ ID No. 144 CACCGTCAACAATACGGGTATCAGGGATAAGGCG

SEQ ID No. 145 ATGGTCATGCCAAGCGGCGTTAAAGTAG

SEQ ID No. 146 ACCCTCAGCAGCGGACAGCCTAAAGG

SEQ ID No. 147 ACCATCACCCAATCCAACGTACCTTTAAAATAA

SEQ ID No. 148 TTTTTCTTGCTGGTTTGCC

SEQ ID No. 149 ATAGTAGTATTTTCAAAGACACCTTCATTAATTTG

SEQ ID No. 150 GATAAGTGCCGTCGAGAGGGTCCCATGTACTGTC

SEQ ID No. 151 CAGTTTGAGGGGACAAAATAGGGGGG

| SEQUENCE LISTINGS |
| --- |
| SEQ ID No. 152 ATTCGTGTCTGGTTTGACCATTAGATACTCAGGTTTTTA |
| SEQ ID No. 153 AAAATTATATGAATATACAGTAACGAACGAGTCAA |
| SEQ ID No. 154 GATGGCAATTCATCAATTCCTGAGCCCGAAC |
| SEQ ID No. 155 AACGAGGGGAGATTTGTATCATCAAAGC |
| SEQ ID No. 156 CATAAGGAAACGTTAAAGGGCTTTCGATCACG |
| SEQ ID No. 157 AGATTTAGAAGTTTCATTCC |
| SEQ ID No. 158 CCAACCAGAACCTATATGTCTGAGAGATGATTGCC |
| SEQ ID No. 159 CAACGGAACCCTAAAGGGAGCCCCCGAGACGGGGA |
| SEQ ID No. 160 GTAATCAAAAATAATTCGCAATTGTAAATCAA |
| SEQ ID No. 161 CAACGAGTAGTAAATTGCATTTGGGGCAATTGCTG |
| SEQ ID No. 162 TGTATCACTCATTTTTAAACCAAGTACCAACCGAC |
| SEQ ID No. 163 GAAGGTTATCGACAACTCGT |
| SEQ ID No. 164 ACAACAATAGGAATGATATAACCTGAACAGACGA |
| SEQ ID No. 165 CCTGAGAGAGTTTGGTTCCGTGTGAGTGCCTGA |
| SEQ ID No. 166 GGAATGCAGCTTCAAAGCGAGCAGGCGAGAAAAACCGTCTATCA |
| SEQ ID No. 167 AATTTTTGGTGAATTACTGA |
| SEQ ID No. 168 TTTTCTGTAGACAGCCGGTTTTGATAGCG |
| SEQ ID No. 169 CCGAACGAAAGTATGGTTTGCAGTATGAACGT |
| SEQ ID No. 170 CGTAGTCTGGCCGCCGTTTTAGAACGCGGCAAGCCCGCCTGT |
| SEQ ID No. 171 CCGCTGTGAGGCCATTACTAGAAATTCTTGCTTTTGATGATA |
| SEQ ID No. 172 ATATTTGCTTTGTTACATTTAAGGG |
| SEQ ID No. 173 CGTAAGATTCAAAATCGGTTGTACCAATAGCA |
| SEQ ID No. 174 TTTTGGGGTCGAGGTGCCGTAAAGGGAACAAGCAAACATCGGAAA |
| SEQ ID No. 175 AACAGTTTCAGTACAAATTTTGCACTTATCCGAGA |
| SEQ ID No. 176 CCTCAGGAAGTTGGTGTACAAGCAATTCCT |
| SEQ ID No. 177 CCGCCCAAAAGGTTAATAAGAGAATATAAATCAT |
| SEQ ID No. 178 TATAATTGAGTGAAGCGCACATTTGAGGATTAGAG |
| SEQ ID No. 179 CTGGGATACGCAAATTGTTTGGATACCATATCAGA |
| SEQ ID No. 180 TAATAACATCCAACAGGAAA |
| SEQ ID No. 181 ACCATCATTACTCGCCATTAAACAGAGGTGA |
| SEQ ID No. 182 AGAGAATAACATAACAATGACAAACAATGCATGATTA |
| SEQ ID No. 183 TCTGTCCATCACGCAAATTAGAACTCAACGAGC |
| SEQ ID No. 184 TATACAGAATCAGCAAAATTCATCTTTAGTTT |
| SEQ ID No. 185 AATATAATTTTGATAATAGAGAGTCAAAGGGCAAATCCTGT |
| SEQ ID No. 186 AATCCTGAGATTCTTTGATT |
| SEQ ID No. 187 ATCTTCATACATGACCAGTATGGCATTTTACTATC |
| SEQ ID No. 188 CTTCAGTGTAGCGGTCGCACGTATATGCAAATTTC |
| SEQ ID No. 189 AACTTTTTCAATGTTTAGTACAAACATCACACGGAACGGTACGCC |
| SEQ ID No. 190 GGCCTTGGCCTCTTCGCTGACGTTGTCGCTCAACATA |

-continued

| SEQUENCE LISTINGS |
|---|

SEQ ID No. 191  ACTGAGCTAAACAGGAGGCGATTTTAG

SEQ ID No. 192  AGATAAAAAATACCGAACGAAATGATACGTGGCAC

SEQ ID No. 193  TCCCCGGGTACCGGCGTTGCGCTC

SEQ ID No. 194  CCTTTAGAGCCAAGTTTGCCTTTAGCGAAAAT

SEQ ID No. 195  TTTTCGTAGGATGAAAGCGTAAGAGGATAGGTCACGAT

SEQ ID No. 196  CAGTGAGCGAGAATCAGCT

SEQ ID No. 197  TATCATCCTTATTTACATTGGCAGATTCATTCTG

SEQ ID No. 198  CTGATAGCCGCTATTAGAACAGAGAT

SEQ ID No. 199  GGGAAACCTCTAACTCAATAAATAATTGCA

SEQ ID No. 200  ACCCATCAGTTTAATAAAAATCGGTTTAACATTTTA

SEQ ID No. 201  AGTTTCGTCACCAGCGGAGCTAACGAGTGAAA

SEQ ID No. 202  TCATAATCTCAGACTGGCGTTTTAATTCG

SEQ ID No. 203  TTTAGCCTTAAACGTTAATTATAAGCAAATATTTAGAA

SEQ ID No. 204  ACTGAGGCGAATGATGAAAAGTCCACTATTAA

SEQ ID No. 205  AAGAGGACAGGCGCAGACGGTCAATTACTTAGCCGGAACGA

SEQ ID No. 206  AGCCGCCGTAAGCGTCTGAC

SEQ ID No. 207  TAACAACCCGTCGGATATTAAATGACGACGATTAC

SEQ ID No. 208  AACTGTCGAGTTTCGACAG

SEQ ID No. 209  AGCACTAGCATGTCAATCAAAAAACAGGCCAT

SEQ ID No. 210  CGCTCATGGATAATAAAAGG

SEQ ID No. 211  CGGTGCAATAAACATGTAATTGGGTCAGTCCGTT

SEQ ID No. 212  CCGTAGAGCTTGCGAGCTGAAA

SEQ ID No. 213  TTAGCGGTTTTAACGTAGGCAGAAAAGCCAAAAG

SEQ ID No. 214  TTGATGGGCAGCAAGTGTAAATCTTAAC

SEQ ID No. 215  CAGACCATTAGATAGCAGCACCGTAATCGCCT

SEQ ID No. 216  CGCCATTTTGTTATAATCAGAAAAGCCCCTATGT

SEQ ID No. 217  TTGCGGGATCGGCTTTGAAACGGGCTTGAGA

SEQ ID No. 218  CTCCGGAACCAGAGCCGCCG

SEQ ID No. 219  CTCCGTCTATCTTTTGTTCAGAAAACGAGAATCAAA

SEQ ID No. 220  CTCCGTCTATCTTTTTTTCAAACTCCAACAGTATCA

SEQ ID No. 221  CTCCGTCTATCTTATGACTGACCAACCCGCCA

SEQ ID No. 222  CTCCGTCTATCTTCATAACCCTCGTTTAC

SEQ ID No. 223  CTCCGTCTATCTTTTTATACTGCG

SEQ ID No. 224  CTCCGTCTATCAGAAACACCAGAAAGTAC

SEQ ID No. 225  CTCCGTCTATCTTAATCATTGTGAATTAC

SEQ ID No. 226  CTCCGTCTATCTTTTTAAGAAGTT

SEQ ID No. 227  CTCCGTCTATCTTTTTTTGACTTC

SEQ ID No. 228  CTCCGTCTATCTTTTTTTTATAGTCAGAAGCAGGTTGAGGCCATCTTT

| SEQUENCE LISTINGS |
|---|
| SEQ ID No. 229 CTCCGTCTATCTTTATCTCCATGTCATAAGGG |
| SEQ ID No. 230 CTCCGTCTATCGTCAGGACGTTGGCGGAACAACATTTGCTACGTCAGC |
| SEQ ID No. 231 ACTTACCCTGACTATTTTTTTTTGCTACGTCAGC |
| SEQ ID No. 232 CTGTACAGGTAACATTCAACTATTGCTACGTCAGC |
| SEQ ID No. 233 AGGTTTAATTTCAACTGCTACGTCAGC |
| SEQ ID No. 234 AGCGCTCATTATACCAGCTACGTCAGC |
| SEQ ID No. 235 GCTGCTTGCCCTGACGGCTACGTCAGC |
| SEQ ID No. 236 CTGAGCGTCCATTTTTGCTACGTCAGC |
| SEQ ID No. 237 CCCTCAGATTTTGCAATTTTTGCTACGTCAGC |
| SEQ ID No. 238 TCACAAACAAATAAATCTTTAAACATTTTTGCTACGTCAGC |
| SEQ ID No. 239 ATACAAGCAACACTATTTGCTACGTCAGC |
| SEQ ID No. 240 TGGAGGAAGCCCGAAATTTTTTTGCTACGTCAGC |
| SEQ ID No. 241 CCAACCAGACCGGAAGTTTTTTTGCTACGTCAGC |
| SEQ ID No. 242 GATAGACGGAG-TEG-Chol |
| SEQ ID No. 243 Chol-TEG-GCTGACGTAGC |

The invention claimed is:

1. A membrane-spanning nanopore, comprising:
   i. at least one scaffold polynucleotide strand;
   ii. a plurality of staple polynucleotide strands; and
   iii. at least one hydrophobically-modified polynucleotide strand, wherein the at least one hydrophobically-modified polynucleotide strand comprises a polynucleotide strand and a hydrophobic moiety;

wherein each of the plurality of staple polynucleotide strands hybridises to the at least one scaffold polynucleotide strand to form the three-dimensional structure of the membrane-spanning nanopore, and wherein the at least one hydrophobically-modified polynucleotide strand hybridises to a portion of the at least one scaffold polynucleotide strand, the membrane-spanning nanopore comprising a membrane spanning region, wherein the membrane spanning region has a wall thickness of more than one DNA duplex, and wherein the membrane spanning region defines a central channel with a minimum internal width of at least about 5 nm.

2. The membrane-spanning nanopore of claim 1, wherein the or each scaffold polynucleotide strand, each of the plurality of staple polynucleotide strands, and the or each hydrophobically-modified polynucleotide strand comprises DNA.

3. The membrane-spanning nanopore of claim 1, wherein the nanopore is assembled via DNA origami techniques.

4. The membrane-spanning nanopore of claim 1, wherein the minimum internal width of the central channel of the nanopore is from about 5 nm to about 20 nm.

5. The membrane-spanning nanopore of claim 1, wherein the nanopore comprises at least one cap region,
   wherein the membrane-spanning region is arranged to abut the at least one cap region, and
   wherein one cap region is present and the membrane-spanning region is located at one end of the nanopore.

6. The membrane-spanning nanopore of claim 5, wherein the membrane-spanning region has a dimension co-axial with the channel of about 1 nm to about 7 nm.

7. The membrane-spanning nanopore of claim 5, wherein the cap region has a dimension co-axial with the channel of about 20 nm to about 70 nm.

8. The membrane-spanning nanopore of claim 1, wherein the nanopore further comprises one or more adaptor polynucleotide strands,
   wherein the at least one hydrophobically-modified polynucleotide strand is hybridised to the nanopore via the one or more adaptor polynucleotide strands, the one of more adaptor polynucleotide strands each having a first end and a second end,
   wherein the first end of the adaptor polynucleotide strand hybridises with the at least one scaffold polynucleotide strand and the second end of the adaptor polynucleotide strand hybridises with the at least one hydrophobically-modified polynucleotide strand.

9. The membrane-spanning nanopore of claim 8, wherein the polynucleotide in the adaptor polynucleotide strands comprises DNA.

10. The membrane-spanning nanopore of claim 1, wherein the at least one hydrophobic moiety comprises a lipid, wherein the lipid is selected from the group consisting of: sterols; alkylated phenols; flavones; saturated and unsaturated fatty acids; and synthetic lipid molecules including dodecyl-beta-D-glucoside.

11. The membrane-spanning nanopore of claim 10, wherein:
the sterols are selected from the group consisting of: cholesterol; derivatives of cholesterol; phytosterol; ergosterol; and bile acid;
the alkylated phenols are selected from the group consisting of: methylated phenols; and
tocopherols;
the flavones are selected from the group consisting of: flavanone containing compounds;
and 6-hydroxyflavone;
the saturated and unsaturated fatty acids are selected from the group consisting of:
derivatives of lauric acid; oleic acid; linoleic acid; and palmitic acids; and
the synthetic lipid molecule is dodecyl-beta-D-glucoside.

12. The membrane-spanning nanopore of claim 1, wherein the nanopore comprises at least one polynucleotide sequence selected from the group consisting of:
a scaffold strand polynucleotide sequence comprising the DNA sequence of m13mp18 DNA (SEQ ID NO. 1); and
one or more staple strand polynucleotide sequences selected from the group comprising SEQ ID Nos. 2 to 218.

13. The membrane-spanning nanopore of claim 8, wherein the nanopore comprises at least one polynucleotide sequence selected from the group consisting of:
an adaptor strand polynucleotide sequence selected from the group comprising SEQ ID Nos. 219 to 241; and
a hydrophobically-modified polynucleotide sequence selected from the group comprising SEQ ID No. 242 or 243.

14. The membrane-spanning nanopore of claim 1, wherein the nanopore has a cross-section perpendicular to a longitudinal axis of the channel that is quadrilateral in shape.

15. The membrane-spanning nanopore of claim 14, wherein the quadrilateral is a square.

16. The membrane-spanning nanopore of claim 1, wherein the membrane-spanning nanopore is modified, wherein the central channel comprises one or more constrictions.

17. A biological sensor, wherein the biological sensor comprises a membrane comprising a nanopore of claim 1 and an apparatus for measuring an ion flow through one or more membrane-spanning nanopores.

* * * * *